(12) United States Patent
Tanaka et al.

(10) Patent No.: US 8,475,389 B2
(45) Date of Patent: Jul. 2, 2013

(54) METHODS AND DEVICES FOR ASSESSMENT OF PNEUMOSTOMA FUNCTION

(75) Inventors: Don Tanaka, Saratoga, CA (US);
Joshua P. Wiesman, Boston, MA (US);
David C. Plough, Portola Valley, CA (US)

(73) Assignee: Portaero, Inc., Cupertino, CA (US)

( * ) Notice: Subject to any disclaimer, the term of this patent is extended or adjusted under 35 U.S.C. 154(b) by 424 days.

(21) Appl. No.: 12/796,409

(22) Filed: Jun. 8, 2010

(65) Prior Publication Data

US 2010/0286544 A1    Nov. 11, 2010

Related U.S. Application Data

(63) Continuation-in-part of application No. 12/388,459, filed on Feb. 18, 2009, now abandoned.

(60) Provisional application No. 61/029,830, filed on Feb. 19, 2008, provisional application No. 61/032,877, filed on Feb. 29, 2008, provisional application No. 61/038,371, filed on Mar. 20, 2008, provisional application No. 61/082,892, filed on Jul. 23, 2008, provisional application No. 61/083,573, filed on Jul. 25, 2008, provisional application No. 61/084,559, filed on Jul. 29, 2008, provisional application No. 61/088,118, filed on Aug. 12, 2008, provisional application No. 61/143,298, filed on Jan. 8, 2009, provisional application No. 61/151,581, filed on Feb. 11, 2009.

(51) Int. Cl.
*A61B 5/08*    (2006.01)
(52) U.S. Cl.
USPC .......................................................... 600/538

(58) Field of Classification Search
USPC ............ 128/200.24, 200.26, 207.14, 207.15, 128/207.16; 600/538
See application file for complete search history.

(56) References Cited

U.S. PATENT DOCUMENTS 733,152 A    7/1903    Chisholm
953,922 A    4/1910    Rogers
(Continued)

FOREIGN PATENT DOCUMENTS

EP    0260543 A1    3/1988
EP    1358904        5/2003
(Continued)

OTHER PUBLICATIONS

EP1808194A2, Chang et al., publication date: Jul. 18 2007.*

(Continued)

*Primary Examiner* — Manuel Mendez
(74) *Attorney, Agent, or Firm* — Fliesler Meyer LLP

(57) ABSTRACT

A pneumostoma assessment and treatment system includes methods and devices for aftercare of a pneumostoma. In particular, methods and devices are provided for standardized monitoring and assessment of pneumostoma patency thereby facilitating the establishment of standards-based protocols for pneumostoma management. Methods of standardized pneumostoma patency assessment includes the use of devices for raising alveolar pressure to a controlled repeatable pressure above ambient while analyzing gas flow through the pneumostoma. In response to an assessment the functionality of the pneumostoma, the tissues of the pneumostoma may be treated with a treatment device utilizing one or more different modalities to preserve or enhance the health and function of the pneumostoma.

20 Claims, 25 Drawing Sheets

U.S. PATENT DOCUMENTS

| | | |
|---|---|---|
| 2,206,687 A | 7/1940 | Bloomheart |
| 2,867,213 A | 1/1959 | Thomas, Jr. |
| 2,873,742 A | 2/1959 | Shelden |
| 2,991,787 A | 7/1961 | Shelden et al. |
| 3,253,594 A | 5/1966 | Matthews et al. |
| 3,384,087 A | 5/1968 | Brummelkamp |
| 3,463,159 A | 8/1969 | Heimlich |
| 3,511,243 A | 5/1970 | Toy |
| 3,556,103 A | 1/1971 | Calhoun et al. |
| 3,638,649 A | 2/1972 | Ersek |
| 3,682,166 A | 8/1972 | Jacobs |
| 3,688,773 A | 9/1972 | Weiss |
| 3,707,146 A | 12/1972 | Cook et al. |
| 3,766,920 A | 10/1973 | Greene |
| 3,777,757 A | 12/1973 | Gray et al. |
| 3,788,326 A | 1/1974 | Jacobs |
| 3,817,250 A | 6/1974 | Weiss et al. |
| 3,908,704 A | 9/1975 | Clement et al. |
| 3,916,903 A | 11/1975 | Pozzi |
| 4,153,058 A | 5/1979 | Nehme |
| 4,291,694 A | 9/1981 | Chai |
| 4,439,189 A | 3/1984 | Sargeant et al. |
| 4,465,062 A | 8/1984 | Versaggi et al. |
| 4,502,482 A | 3/1985 | DeLuccia et al. |
| 4,583,977 A | 4/1986 | Shishov et al. |
| 4,664,660 A | 5/1987 | Goldberg et al. |
| 4,799,494 A | 1/1989 | Wang |
| 4,813,929 A | 3/1989 | Semrad |
| 4,826,495 A | 5/1989 | Petersen |
| 4,828,553 A | 5/1989 | Nielsen |
| 4,869,717 A | 9/1989 | Adair |
| 4,872,869 A | 10/1989 | Johns |
| 4,889,534 A | 12/1989 | Mohiuddin et al. |
| 4,931,045 A | 6/1990 | Steer |
| 4,944,724 A | 7/1990 | Goldberg et al. |
| 4,959,054 A | 9/1990 | Heimke et al. |
| 4,976,688 A | 12/1990 | Rosenblum |
| 5,004,456 A | 4/1991 | Botterbusch et al. |
| 5,060,645 A | 10/1991 | Russell |
| 5,078,689 A | 1/1992 | Keller |
| 5,137,509 A | 8/1992 | Freitas |
| 5,139,485 A | 8/1992 | Smith et al. |
| 5,218,957 A | 6/1993 | Strickland |
| 5,230,332 A | 7/1993 | Strickland |
| 5,230,350 A | 7/1993 | Fentress |
| 5,245,995 A | 9/1993 | Sullivan et al. |
| 5,261,708 A | 11/1993 | Steer |
| 5,263,939 A | 11/1993 | Wortrich |
| 5,312,331 A | 5/1994 | Knoepfler |
| 5,315,992 A | 5/1994 | Dalton |
| 5,318,523 A | 6/1994 | Lu |
| 5,336,206 A | 8/1994 | Shichman |
| 5,354,283 A | 10/1994 | Bark et al. |
| 5,356,386 A | 10/1994 | Goldberg et al. |
| 5,366,478 A | 11/1994 | Brinkerhoff et al. |
| 5,370,625 A | 12/1994 | Shichman |
| 5,376,376 A | 12/1994 | Li |
| 5,389,077 A | 2/1995 | Melinyshyn et al. |
| 5,401,262 A | 3/1995 | Karwoski et al. |
| 5,403,264 A | 4/1995 | Wohlers et al. |
| 5,431,633 A | 7/1995 | Fury |
| 5,478,333 A | 12/1995 | Asherman, Jr. |
| 5,484,401 A | 1/1996 | Rodriguez et al. |
| 5,496,297 A | 3/1996 | Olsen |
| 5,501,677 A | 3/1996 | Jensen |
| 5,501,678 A | 3/1996 | Olsen |
| 5,588,424 A | 12/1996 | Insler et al. |
| 5,616,131 A | 4/1997 | Sauer et al. |
| 5,660,175 A | 8/1997 | Dayal |
| 5,662,629 A | 9/1997 | Steer et al. |
| 5,728,066 A | 3/1998 | Daneshvar |
| 5,730,735 A | 3/1998 | Holmberg et al. |
| 5,738,661 A | 4/1998 | Larice |
| 5,807,341 A | 9/1998 | Heim |
| 5,830,200 A | 11/1998 | Steer et al. |
| 5,843,053 A | 12/1998 | Steer |
| 5,897,531 A | 4/1999 | Amirana |
| 5,931,821 A | 8/1999 | Weilbacher et al. |
| 5,954,636 A | 9/1999 | Schwartz et al. |
| 5,971,962 A | 10/1999 | Kojima et al. |
| 5,972,026 A | 10/1999 | Laufer et al. |
| 6,056,744 A | 5/2000 | Edwards |
| 6,059,816 A | 5/2000 | Moenning |
| 6,083,255 A | 7/2000 | Laufer et al. |
| 6,174,323 B1 | 1/2001 | Biggs et al. |
| 6,179,784 B1 * | 1/2001 | Daniels et al. ............... 600/538 |
| 6,197,010 B1 | 3/2001 | Leise, Jr. et al. |
| 6,200,333 B1 | 3/2001 | Laufer |
| 6,258,100 B1 | 7/2001 | Alferness et al. |
| 6,273,907 B1 | 8/2001 | Laufer |
| 6,283,988 B1 | 9/2001 | Laufer et al. |
| 6,283,989 B1 | 9/2001 | Laufer et al. |
| 6,287,290 B1 | 9/2001 | Perkins et al. |
| 6,293,930 B1 | 9/2001 | Brunsgaard et al. |
| 6,293,951 B1 | 9/2001 | Alferness et al. |
| 6,299,633 B1 | 10/2001 | Laufer |
| 6,322,536 B1 | 11/2001 | Rosengart et al. |
| 6,328,689 B1 | 12/2001 | Gonzalez et al. |
| 6,330,882 B1 | 12/2001 | French |
| 6,334,441 B1 | 1/2002 | Zowtiak et al. |
| 6,358,269 B1 | 3/2002 | Aye |
| 6,398,775 B1 | 6/2002 | Perkins et al. |
| 6,402,754 B1 | 6/2002 | Gonzalez |
| 6,411,852 B1 | 6/2002 | Danek et al. |
| 6,416,554 B1 | 7/2002 | Alferness et al. |
| 6,432,100 B1 | 8/2002 | Affeld |
| 6,443,156 B1 | 9/2002 | Niklason et al. |
| 6,468,292 B1 | 10/2002 | Mollenauer et al. |
| 6,485,407 B2 | 11/2002 | Alferness et al. |
| 6,488,673 B1 | 12/2002 | Laufer et al. |
| 6,491,706 B1 | 12/2002 | Alferness et al. |
| 6,514,290 B1 | 2/2003 | Loomas |
| 6,517,519 B1 | 2/2003 | Rosen et al. |
| 6,520,183 B2 | 2/2003 | Amar |
| 6,527,761 B1 | 3/2003 | Soltesz et al. |
| 6,550,475 B1 | 4/2003 | Oldfield |
| 6,569,121 B1 | 5/2003 | Purow et al. |
| 6,569,166 B2 | 5/2003 | Gonzalez |
| 6,585,639 B1 | 7/2003 | Kotmel et al. |
| 6,589,161 B2 | 7/2003 | Corcoran |
| 6,592,594 B2 | 7/2003 | Rimbaugh et al. |
| 6,599,311 B1 | 7/2003 | Biggs et al. |
| 6,609,521 B1 | 8/2003 | Belani et al. |
| 6,629,951 B2 | 10/2003 | Laufer et al. |
| 6,632,239 B2 | 10/2003 | Snyder et al. |
| 6,632,243 B1 | 10/2003 | Zadno-Azizi et al. |
| 6,634,360 B1 | 10/2003 | Flodin |
| 6,634,363 B1 | 10/2003 | Danek et al. |
| 6,638,253 B2 | 10/2003 | Breznock |
| 6,653,525 B2 | 11/2003 | Ingenito et al. |
| 6,659,961 B2 | 12/2003 | Robinson |
| 6,679,264 B1 | 1/2004 | Deem et al. |
| 6,682,506 B1 | 1/2004 | Navarro |
| 6,692,494 B1 | 2/2004 | Cooper et al. |
| 6,694,979 B2 | 2/2004 | Deem et al. |
| 6,695,791 B2 | 2/2004 | Gonzalez |
| 6,709,401 B2 | 3/2004 | Perkins et al. |
| 6,712,812 B2 | 3/2004 | Roschak et al. |
| 6,723,055 B2 * | 4/2004 | Hoffman ............... 600/538 |
| 6,726,598 B1 | 4/2004 | Jarvis et al. |
| 6,736,797 B1 | 5/2004 | Larsen et al. |
| 6,749,606 B2 | 6/2004 | Keast et al. |
| 6,770,063 B2 | 8/2004 | Goldberg et al. |
| 6,770,070 B1 | 8/2004 | Balbierz |
| 6,790,172 B2 | 9/2004 | Alferness et al. |
| 6,827,086 B2 | 12/2004 | Shuman |
| 6,837,906 B2 | 1/2005 | Ginn |
| 6,840,243 B2 | 1/2005 | Deem et al. |
| 6,843,767 B2 | 1/2005 | Corcoran et al. |
| 6,846,292 B2 | 1/2005 | Bakry |
| 6,849,061 B2 | 2/2005 | Wagner |
| 6,852,108 B2 | 2/2005 | Barry et al. |
| 6,860,847 B2 | 3/2005 | Alferness et al. |
| 6,878,141 B1 | 4/2005 | Perkins et al. |
| 6,886,558 B2 | 5/2005 | Tanaka |
| 6,901,927 B2 | 6/2005 | Deem et al. |
| 6,904,909 B2 | 6/2005 | Andreas et al. |

| | | |
|---|---|---|
| 6,905,518 B2 | 6/2005 | Ginn |
| 6,916,310 B2 | 7/2005 | Sommerich |
| 6,929,637 B2 | 8/2005 | Gonzalez et al. |
| 6,941,950 B2 | 9/2005 | Wilson et al. |
| 6,997,189 B2 | 2/2006 | Biggs et al. |
| 6,997,918 B2 | 2/2006 | Soltesz et al. |
| 7,011,094 B2 | 3/2006 | Rapacki et al. |
| 7,014,628 B2 | 3/2006 | Bousquet |
| 7,022,088 B2 | 4/2006 | Keast et al. |
| 7,033,387 B2 | 4/2006 | Zadno-Azizi et al. |
| 7,036,509 B2 | 5/2006 | Rapacki et al. |
| 7,086,398 B2 | 8/2006 | Tanaka |
| 7,100,616 B2 | 9/2006 | Springmeyer |
| 7,135,010 B2 | 11/2006 | Buckman et al. |
| 7,141,046 B2 | 11/2006 | Perkins et al. |
| 7,165,548 B2 | 1/2007 | Deem et al. |
| 7,172,581 B2 | 2/2007 | Ciok et al. |
| 7,175,644 B2 | 2/2007 | Cooper et al. |
| 7,182,772 B2 | 2/2007 | Alferness et al. |
| 7,186,259 B2 | 3/2007 | Perkins et al. |
| 7,192,420 B2 | 3/2007 | Whiteford |
| 7,195,016 B2 | 3/2007 | Loyd et al. |
| 7,195,017 B2 | 3/2007 | Tanaka |
| 7,207,946 B2 | 4/2007 | Sirokman |
| 7,232,414 B2 | 6/2007 | Gonzalez |
| 7,244,245 B2 | 7/2007 | Purow et al. |
| 7,252,086 B2 | 8/2007 | Tanaka |
| 7,377,278 B2 | 5/2008 | Tanaka |
| 7,383,740 B2 | 6/2008 | Krasilchikov et al. |
| 7,398,782 B2 | 7/2008 | Tanaka |
| 7,406,963 B2 | 8/2008 | Chang et al. |
| 7,426,929 B2 | 9/2008 | Tanaka |
| 7,533,667 B2 | 5/2009 | Tanaka |
| 2001/0025132 A1 | 9/2001 | Alferness et al. |
| 2001/0041906 A1 | 11/2001 | Gonzalez |
| 2001/0041932 A1 | 11/2001 | Scholz et al. |
| 2002/0042564 A1 | 4/2002 | Cooper et al. |
| 2002/0062120 A1 | 5/2002 | Perkins et al. |
| 2002/0077593 A1 | 6/2002 | Perkins et al. |
| 2002/0087153 A1 | 7/2002 | Roschak et al. |
| 2002/0111619 A1 | 8/2002 | Keast et al. |
| 2002/0111620 A1 | 8/2002 | Cooper et al. |
| 2002/0112729 A1 | 8/2002 | DeVore et al. |
| 2002/0120177 A1 | 8/2002 | Borst et al. |
| 2002/0165618 A1 | 11/2002 | Ingenito et al. |
| 2002/0188171 A1 | 12/2002 | Alferness et al. |
| 2003/0013935 A1 | 1/2003 | Alferness et al. |
| 2003/0018344 A1 | 1/2003 | Kaji et al. |
| 2003/0050648 A1 | 3/2003 | Alferness et al. |
| 2003/0051733 A1 | 3/2003 | Kotmel et al. |
| 2003/0055331 A1 | 3/2003 | Kotmel et al. |
| 2003/0065339 A1 | 4/2003 | Snyder et al. |
| 2003/0069488 A1 | 4/2003 | Alferness et al. |
| 2003/0078469 A1 | 4/2003 | Corcoran |
| 2003/0083542 A1 | 5/2003 | Alferness et al. |
| 2003/0083671 A1 | 5/2003 | Rimbaugh et al. |
| 2003/0127090 A1 | 7/2003 | Gifford et al. |
| 2003/0130593 A1 | 7/2003 | Gonzalez |
| 2003/0149446 A1 | 8/2003 | Shuman |
| 2003/0154988 A1 | 8/2003 | DeVore et al. |
| 2003/0158515 A1 | 8/2003 | Gonzalez et al. |
| 2003/0163024 A1 | 8/2003 | Corcoran |
| 2003/0181356 A1 | 9/2003 | Ingenito |
| 2003/0181922 A1 | 9/2003 | Alferness |
| 2003/0183235 A1 | 10/2003 | Rimbaugh et al. |
| 2003/0186904 A1 | 10/2003 | Ruben et al. |
| 2003/0195385 A1 | 10/2003 | DeVore |
| 2003/0195511 A1 | 10/2003 | Barry |
| 2003/0212337 A1 | 11/2003 | Sirokman |
| 2003/0212412 A1 | 11/2003 | Dillard et al. |
| 2003/0216730 A1 | 11/2003 | Barry et al. |
| 2003/0216769 A1 | 11/2003 | Dillard et al. |
| 2003/0228344 A1 | 12/2003 | Fields et al. |
| 2003/0233099 A1 | 12/2003 | Danaek et al. |
| 2004/0010209 A1 | 1/2004 | Sirokman |
| 2004/0010289 A1 | 1/2004 | Biggs et al. |
| 2004/0016435 A1 | 1/2004 | Deem et al. |
| 2004/0024356 A1 | 2/2004 | Tanaka |
| 2004/0031494 A1 | 2/2004 | Danek et al. |
| 2004/0040555 A1 | 3/2004 | Tanaka |
| 2004/0047855 A1 | 3/2004 | Ingenito |
| 2004/0055606 A1 | 3/2004 | Hendricksen et al. |
| 2004/0059263 A1 | 3/2004 | DeVore et al. |
| 2004/0073155 A1 | 4/2004 | Laufer et al. |
| 2004/0073191 A1 | 4/2004 | Soltesz et al. |
| 2004/0073201 A1 | 4/2004 | Cooper et al. |
| 2004/0073241 A1 | 4/2004 | Barry et al. |
| 2004/0078026 A1 | 4/2004 | Wagner |
| 2004/0078054 A1 | 4/2004 | Biggs et al. |
| 2004/0087831 A1 | 5/2004 | Michels et al. |
| 2004/0097983 A1 | 5/2004 | Snyder et al. |
| 2004/0143282 A1 | 7/2004 | Dillard et al. |
| 2004/0144387 A1 | 7/2004 | Amar |
| 2004/0158228 A1 | 8/2004 | Perkins et al. |
| 2004/0167636 A1 | 8/2004 | Dillard et al. |
| 2004/0173218 A1 | 9/2004 | Yamada et al. |
| 2004/0199128 A1 | 10/2004 | Morris et al. |
| 2004/0200484 A1 | 10/2004 | Springmeyer |
| 2004/0206349 A1 | 10/2004 | Alferness et al. |
| 2004/0210248 A1 | 10/2004 | Gordon et al. |
| 2004/0211412 A1 | 10/2004 | Alferness et al. |
| 2004/0211434 A1 | 10/2004 | Loomas et al. |
| 2004/0220446 A1 | 11/2004 | Corcoran et al. |
| 2004/0220556 A1 | 11/2004 | Cooper et al. |
| 2004/0225254 A1 | 11/2004 | Tanaka et al. |
| 2004/0231674 A1 | 11/2004 | Tanaka |
| 2004/0237966 A1 | 12/2004 | Tanaka |
| 2004/0243140 A1 | 12/2004 | Alferness et al. |
| 2004/0244802 A1 | 12/2004 | Tanaka |
| 2004/0244803 A1 | 12/2004 | Tanaka |
| 2005/0005936 A1 | 1/2005 | Wondka |
| 2005/0015106 A1 | 1/2005 | Perkins et al. |
| 2005/0022809 A1 | 2/2005 | Wondka |
| 2005/0025816 A1 | 2/2005 | Tanaka |
| 2005/0033310 A1 | 2/2005 | Alferness et al. |
| 2005/0033344 A1 | 2/2005 | Dillard et al. |
| 2005/0043745 A1 | 2/2005 | Alferness et al. |
| 2005/0043751 A1 | 2/2005 | Phan et al. |
| 2005/0043752 A1 | 2/2005 | Phan et al. |
| 2005/0049615 A1 | 3/2005 | Cooper et al. |
| 2005/0056292 A1 | 3/2005 | Cooper |
| 2005/0060041 A1 | 3/2005 | Phan et al. |
| 2005/0060042 A1 | 3/2005 | Phan et al. |
| 2005/0060044 A1 | 3/2005 | Roschak et al. |
| 2005/0061322 A1 | 3/2005 | Freitag |
| 2005/0066976 A1 | 3/2005 | Wondka |
| 2005/0085801 A1 | 4/2005 | Cooper et al. |
| 2005/0096529 A1 | 5/2005 | Cooper et al. |
| 2005/0103340 A1 | 5/2005 | Wondka |
| 2005/0107783 A1 | 5/2005 | Tom et al. |
| 2005/0131276 A1 | 6/2005 | Alferness et al. |
| 2005/0137518 A1 | 6/2005 | Biggs et al. |
| 2005/0137611 A1 | 6/2005 | Escudero et al. |
| 2005/0137712 A1 | 6/2005 | Biggs et al. |
| 2005/0137715 A1 | 6/2005 | Phan et al. |
| 2005/0145253 A1 | 7/2005 | Wilson et al. |
| 2005/0161040 A1 | 7/2005 | Tanaka |
| 2005/0166925 A1 | 8/2005 | Wilson et al. |
| 2005/0171396 A1 | 8/2005 | Pankratov et al. |
| 2005/0177144 A1 | 8/2005 | Phan et al. |
| 2005/0178385 A1 | 8/2005 | Dellaca' et al. |
| 2005/0178389 A1 | 8/2005 | Shaw et al. |
| 2005/0192526 A1 | 9/2005 | Biggs et al. |
| 2005/0203483 A1 | 9/2005 | Perkins et al. |
| 2005/0205097 A1 | 9/2005 | Kyle |
| 2005/0244401 A1 | 11/2005 | Ingenito |
| 2005/0281797 A1 | 12/2005 | Gong et al. |
| 2005/0281801 A1 | 12/2005 | Gong et al. |
| 2005/0281802 A1 | 12/2005 | Gong et al. |
| 2005/0282748 A1 | 12/2005 | Gong et al. |
| 2005/0288549 A1 | 12/2005 | Mathis |
| 2005/0288550 A1 | 12/2005 | Mathis |
| 2005/0288684 A1 | 12/2005 | Aronson et al. |
| 2005/0288702 A1 | 12/2005 | McGurk et al. |
| 2006/0004400 A1 | 1/2006 | McGurk et al. |
| 2006/0009748 A1 | 1/2006 | Mathis |
| 2006/0025815 A1 | 2/2006 | McGurk et al. |
| 2006/0047291 A1 | 3/2006 | Barry |

| | | |
|---|---|---|
| 2006/0076023 A1 | 4/2006 | Rapacki et al. |
| 2006/0079838 A1 | 4/2006 | Walker et al. |
| 2006/0095002 A1 | 5/2006 | Soltesz et al. |
| 2006/0107961 A1 | 5/2006 | Tanaka |
| 2006/0116749 A1 | 6/2006 | Willink et al. |
| 2006/0118125 A1 | 6/2006 | Tanaka |
| 2006/0118126 A1 | 6/2006 | Tanaka |
| 2006/0124126 A1 | 6/2006 | Tanaka |
| 2006/0130830 A1 | 6/2006 | Barry |
| 2006/0135947 A1 | 6/2006 | Soltesz et al. |
| 2006/0135984 A1 | 6/2006 | Kramer et al. |
| 2006/0142672 A1 | 6/2006 | Keast et al. |
| 2006/0161233 A1 | 7/2006 | Barry et al. |
| 2006/0162731 A1 | 7/2006 | Wondka et al. |
| 2006/0206147 A1 | 9/2006 | DeVore et al. |
| 2006/0212046 A1 | 9/2006 | Pearce et al. |
| 2006/0212051 A1 | 9/2006 | Snyder et al. |
| 2006/0235432 A1 | 10/2006 | DeVore et al. |
| 2006/0235467 A1 | 10/2006 | DeVore |
| 2006/0264772 A1 | 11/2006 | Aljuri et al. |
| 2006/0276807 A1 | 12/2006 | Keast et al. |
| 2006/0280772 A1 | 12/2006 | Roschak et al. |
| 2006/0280773 A1 | 12/2006 | Roschak et al. |
| 2006/0283462 A1 | 12/2006 | Fields et al. |
| 2007/0005083 A1 | 1/2007 | Sabanathan et al. |
| 2007/0027434 A1 | 2/2007 | Pedersen et al. |
| 2007/0043350 A1 | 2/2007 | Soltesz et al. |
| 2007/0051372 A1 | 3/2007 | Tanaka |
| 2007/0055175 A1 | 3/2007 | Caro |
| 2007/0088300 A1 | 4/2007 | Cline et al. |
| 2007/0123922 A1 | 5/2007 | Cooper et al. |
| 2007/0128174 A1 | 6/2007 | Kleinsek et al. |
| 2007/0142742 A1 | 6/2007 | Aljuri et al. |
| 2007/0163598 A1 | 7/2007 | Chang et al. |
| 2007/0185531 A1 | 8/2007 | Rimbaugh et al. |
| 2007/0186932 A1 | 8/2007 | Wondka et al. |
| 2007/0186933 A1 | 8/2007 | Domingo et al. |
| 2007/0299424 A1 | 12/2007 | Cumming et al. |
| 2008/0281151 A1 | 11/2008 | Chang et al. |
| 2008/0281295 A1 | 11/2008 | Chang et al. |
| 2008/0281433 A1 | 11/2008 | Chang et al. |
| 2008/0283065 A1 | 11/2008 | Chang et al. |
| 2008/0287878 A1 | 11/2008 | Tanaka |
| 2008/0287973 A1 | 11/2008 | Aster et al. |
| 2008/0295829 A1 | 12/2008 | Evens |
| 2009/0205641 A1 | 8/2009 | Tanaka |
| 2009/0205643 A1 | 8/2009 | Tanaka et al. |
| 2009/0205644 A1 | 8/2009 | Tanaka et al. |
| 2009/0205645 A1 | 8/2009 | Tanaka et al. |
| 2009/0205646 A1 | 8/2009 | Tanaka et al. |
| 2009/0205647 A1 | 8/2009 | Plough et al. |
| 2009/0205648 A1 | 8/2009 | Tanaka et al. |
| 2009/0205649 A1 | 8/2009 | Tanaka et al. |
| 2009/0205650 A1 | 8/2009 | Tanaka et al. |
| 2009/0205651 A1 | 8/2009 | Tanaka et al. |
| 2009/0205658 A1 | 8/2009 | Tanaka et al. |
| 2009/0205665 A1 | 8/2009 | Tanaka et al. |
| 2009/0209856 A1 | 8/2009 | Tanaka et al. |
| 2009/0209906 A1 | 8/2009 | Tanaka et al. |
| 2009/0209909 A1 | 8/2009 | Tanaka et al. |
| 2009/0209917 A1 | 8/2009 | Tanaka et al. |
| 2009/0209924 A1 | 8/2009 | Tanaka |
| 2009/0209936 A1 | 8/2009 | Tanaka et al. |
| 2009/0209970 A1 | 8/2009 | Tanaka et al. |
| 2009/0209971 A1 | 8/2009 | Tanaka et al. |

FOREIGN PATENT DOCUMENTS

| | | |
|---|---|---|
| EP | 1658867 | 5/2006 |
| EP | 1815821 | 8/2007 |
| EP | 2242527 | 10/2010 |
| JP | 62-2028747 U | 6/1986 |
| JP | 2000-197706 | 7/2000 |
| JP | 2000197006 | 7/2000 |
| RU | 2192185 | 10/2002 |
| WO | WO 96/39960 | 12/1996 |
| WO | WO 99/66975 | 12/1999 |
| WO | WO 00/76577 A1 | 12/2000 |
| WO | WO 01/45568 A1 | 6/2001 |
| WO | WO 02/04054 | 1/2002 |
| WO | WO2005070480 | 8/2005 |

OTHER PUBLICATIONS

International Search Report for PCT/US2009/034374 dated Jun. 22, 2011, 7 pages.
Extended European Search Report dated Jun. 22, 2011 for PCT/US2009034374, 7 pages.
Extended European Search Report dated Jun. 15, 2011 for PCT/US2009034322, 7 pages.
Extended European Search Report dated Sep. 16, 2011 for PCT/US2009034380, 8 pages.
Moore et al., "Unilateral Extrapulmonary Airway Bypass in Advanced Emphysema", The Annals of Thoracic Surgery 2010; 89:899-906.
International Search Report for PCT/US2009/034322 dated Jun. 6, 2011, 7 pages.
Aljuri et al., "Validation and pilot clinical study of a new bronchoscopic method to measure collateral ventilation before endobronchial lung volume reduction", J Appl Physio 106: 774-783, 2009.
Al-Salem et al., "Computed tomography-guided percutaneous needle aspiration of lung abscesses in neonates and children", Pediatr Surg Int (1997) 12: 417-419, copyright Springer-Verlag 1997.
Ball, Jr et al., "Percutaneous Drainage of Chest Abscesses in Children", Radiology 1989; 171: 431-434.
Becker et al., "Lung Volumes before and after Lung Volume Reduction Surgery: Quantitative CT Analysis", Am J Respir Crit Care Med 1998; 157: 1593-1599.
Brenner et al., "Innovative Approaches to Lung Volume Reduction for Emphysema", Chest 2004; 126: 238-248.
Brutinel et al., "A two-year experience with the neodymium-YAG laser in endobronchial obstruction", Chest 1987; 91: 159-165.
Celli et al. "Standards for the diagnosis and treatment of patients with COPD: a summary of the ATS/ERS position paper", European Respiratory Journal 2004; 23; 932-946.
Cetti et al., "Collateral ventilation", Thorax 2006; 61: 371-373.
Chino et al., "Ventilation of Excised Human Lungs Via Spiracles through the Pleura", Thematic Poster Session (Abstract p. A546) Session: 12:45 pm-4:15 pm, May 2003, Mechanics of the Lung and Respiratory System.
Choong et al., "Feasibility and safety of airway bypass stent placement and influence of topical mitomycin C on stent patency", The Journal of Thoracic and Cardiovascular Surgery 2005; 129: 632-638.
Choong et al., "Transpleural ventilation of explanted human lungs", Thorax 2007; 62: 623-630; originally published online Apr. 5, 2007.
Cope, J. Hallam, "Monaldi Procedure", Presented at the annual meeting of the California Tuberculosis and Health Association and the California Trudeau Society, Mar. 30-Apr. 1, 1950, San Diego; retrieved from California Medicine Dec. 1950; vol. 73, No. 6: 563-564.
Dumon, J. F., "A Dedicated Tracheobronchial Stent", Chest 1990; 97: 328-332.
Eloesser, "An Operation for Tuberculous Empyema", Chest 1935; 1: 8-23.
Fein, Alan M, "Lung Volume Reduction Surgery: Answering the Crucial Questions", Chest 1998; 113: 277-282.
Fernandes et al., *Airway Hyperresponsiveness: From Molecules to Bedside Invited Review*: Do inflammatory mediators influence the contribution of airway smooth muscle contraction to airway hyperresponsiveness in asthma?", Journal Appl Physiol 2003; 95; 844-853.
Fessler, Henry E., "Collateral Ventilation, the Bane of Bronchoscopic Volume Reduction", Am J Respir Crit Care Med 2005; 171: 423-425.
Frawley et al., "Airway Pressure Release Ventilation: Theory and Practice", AACN Clinical Issues 2001; vol. 12, No. 2; 234-246.
Freitag et al., "Theoretical and experimental basis for the development of a dynamic airway stent", European Respiratory Journal 1994; 7: 2038-2045.
Ghaye et al , "Imaging guided thoracic interventions", European Respiratory Journal 2001; 17: 507-528.

Golding et al., "External drainage of large bullae in severe generalized emphysema", Journal of Thoracic and Cardiovascular Surgery Jun. 1968; vol. 55, No. 6: 891-894.
Goldstraw et al., "The Surgical Treatment of Emphysema: The Brompton Approach", Chest Surgery Clinics of North America Nov. 1995; vol. 5, No. 4: 777-797.
Habashi, Nader M., "Other approaches to open-lung ventilation: Airway pressure release ventilation", Crit Care Med 2005, vol.33, No. 3 (Suppl): S228-S240.
Harada et al., "Re-expansion of Refractory Atelectasis Using a Bronchofiberscope with a Balloon Cuff", Chest 1983; 84: 725-728.
Head et al., "Intracavitary Suction (Monaldi) in the Treatment of Emphysematous Bullae and Blebs", Journal of Thoracic Surgery Dec. 1949; vol. 18, No. 6: 761-776.
Heimlich, Henry J., "Respiratory Rehabilitation with Transtracheal Oxygen System", Ann Otol Rhinol Laryngol Nov./Dec. 1982; 91: 643-647.
Hogg et al., "Chronic obstructive pulmonary disease c2: Pathology and biochemistry of emphysema", Thorax 2002; 57: 830-834.
Hogg et al., "The Resistance of Collateral Channels in Excised Human Lungs", Journal of Clinical Investigation 1969; 48: 421-431.
Joannette, Albert, "Drainage of Tuberculous Cavities by Aspiration (Monaldi Method)", The Canadian Medical Association Journal Jan. 1941; 46-48.
Korpela et al., "Bioabsorbable Self-reinforced Poly-L-Lactide, Metallic, and Silicone Stents in the Management of Experimental Tracheal Stenosis", Chest 1999; 115: 490-495.
Lausberg et al., "Bronchial Fenestration Improves Expiratory Flow in Emphysematous Human Lungs", Annals of Thoracic Surgery 2003; 75: 393-398.
Lorenzo et al., "Lung Abscesses in Children: Diagnostic and Therapeutic Needle Aspiration", Radiology Oct. 1985; 157: 79-80.
MacArthur et al., "Intracavity suction and drainage in the treatment of emphysematous bullae", Thorax 1977; 32: 668-672.
MacKlem, Peter T., "Collateral Ventilation", The New England Journal of Medicine Jan. 5, 1978; 298(1): 49-50.
Matson et al., "Evaluation of Various Surgical Procedures in the Treatment of Pulmonary Tuberculosis", Chest 1946; 12: 40-47.
McCoy, Robert, "Oxygen-Conserving Techniques and Devices", Respiratory Care Jan. 2000, vol. 45, No. 1: 95-104.
Meyers et al., "Chronic obstructive pulmonary disease 10: Bullectomy, lung volume reduction surgery, and transplantation for patients with chronic obstructive pulmonary disease", Thorax 2003; 58: 634-638.
Mineo et al., "Awake Nonresectional Lung Volume Reduction Surgery", Annals of Surgery 2006; 243: 131-136.
Monaldi, V., "Endocavitary Aspiration: Its Practical Application", Tubercle 1947: 223-228.
Monaldi, V., "Endocavitary Aspiration in the Treatment of Lung Abscess", Chest 1956; 29: 193-201.
Monaldi, V., "Endocavitary Aspiration in the Treatment of Pathological Cavities of the Lung", Proceedings of the International Conference on Tuberculosis, Scandinavian Journal of Respiratory Diseases Supplementum 1968; 65: 113-121.
U.S. Department of Health and Human Services; National Institutes of Health National Heart, Lung, and Blood Institute; "Chronic Obstructive Pulmonary Disease", NIH Publication No. 03/5229 Mar. 2003: 1-6.
Parker et al., "Percutaneous small bore catheter drainage in the management of lung abscesses", Chest 1987; 92: 213-218.
Petty, Thomas L., "The history of COPD", International Journal of COPD 2006; 1(1): 3-14.
Polkey, M. J., "Surgical procedures in emphysema: any impact on dynamic hyperinflation?" European Respiratory Review 2006; 15(100): 96-98.
Polkey, M. J., "Bronchoscopic lung volume reduction", European Respiratory Review 2006; 15(100): 99-103.
Rendina et al., "Feasibility and safety of the airway bypass procedure for patients with emphysema", The Journal of Thoracic and Cardiovascular Surgery 2003; 125: 1294-1299.
Rockey, Edward E., "Tube Pneumonostomy for Thoracotomy Reject Crippling Bulbous Emphysema", New York State Journal of Medicine Mar. 1, 1973: 664-671.
Rousseau et al., "Self-expandable Prostheses in the Tracheobronchial Tree", Thoracic Radiology 1993; 188: 199-203.
Russi et al., "Lung volume reduction surgery: what can we learn from the National Emphysema Treatment Trial?" European Respiratory Journal 2003; 22: 571-573.
Saad et al., "Surgical treatment of bullae for Bulbous emphysema: a simple drainage", J. Pneumologia 2000; 26(3): 1-11, retrieved from <http://www.scielo.br/scielo.php?script=arttext&pid=S0102-35862000000300003&lng=e...> May 2, 2007.
Shah, Pallav, "Surgical and Non-surgical Volume Reduction for COPD", Presented at the Clinical Consensus on COPD, Mar 2-3, 2007, Novotel London West, 56 pages; see p. 55 of 56.
Shah et al., "Surgical Treatment of Bulbous Emphysema: Experience with the Brompton Technique", Annals of Thoracic Surgery 1994; 58: 1452-1456.
Shim et al., "Percutaneous Drainage of Lung Abscess", Lung 1990; 168: 201-207.
Snell et al., "The Potential for Bronchoscopic Lung Volume Reduction Using Bronchial Prostheses: A Pilot Study", Chest 2003; 124: 1073-1080.
Snell, Gregory L, "Airway Bypass Stenting for Severe Emphysema", retrieved from <http://www.ctsnet.org/sections/thoracic/newtechnology/article-4.html>, Aug. 6, 2007, 4 pages.
Springmeyer, Steven C., "Development of a Bronchial Valve for Treatment of Severe Emphysema", retrieved from <http://www.ctsnet.org/sections/thoracic/newtechnology/article-10.html>, Jul. 16, 2007, 6 pages.
Stewart et al., "Decompression of Giant Bulla in Acute Pneumonia: Surgical Palliation Prior to Definitive Management", Ann Thoracic Surg 2006; 82: 2308-2309.
Sugarmann et al., "Mesh insertion as an aid for pleurodesis", Journal of Cardiovascular Surgery 1996; 37 (Suppl. 1 to No. 6):173-5.
Swallow et al., "Quadriceps strength predicts mortality in patients with moderate to severe chronic obstructive pulmonary disease", Thorax 2007; 62: 115-120.
Symbas et al., "Nontuberculous Pleural Empyema in Adults, The Role of a Modified Eloesser Procedure in Its Management", The Annals of Thoracic Surgery 1971; 12: 69-78.
Takizawa et al., "Computed tomography-guided drainage for large pulmonary bullae", Interactive Cardiovascular and Thoracic Surgery 2004; 3: 283-285.
Terry et al., "Collateral Ventilation in Man", The New England Journal of Medicine 1978; 298(1): 10-15.
Thourani et al., "Twenty-six Years of Experience With the Modified Eloesser Flap", Ann Thorac Surg 2003; 76: 401-406.
Toma et al., "Brave new world for interventional bronchoscopy", Thorax 2005; 60: 180-181.
Ugama et al., "Drainage of Giant Bulla with Balloon Catheter Using Chemical Irritant and Fibrin Glue", Chest 1988; 94(6); 1289-1290.
Vainrub et al., "Percutaneous Drainage of Lung Abscess", American Review of Respiratory Disease 1978; 117: 153-160.
Venn et al., "Intracavity drainage for Bulbous, emphysematous lung disease: experience with the Brompton technique", Thorax 1988; 43: 998-1002.
Wood et al., "A multicenter trial of an intrabronchial valve for treatment of severe emphysema", The Journal of Thoracic and Cardiovascular Surgery 2007; 133: 65-73.e2.
Woodring et al., "Pneumothorax ex vacuo", Chest 1996, 110: 1102-1124.
Woolcock et al., "Mechanical factors influencing collateral ventilation in human, dog, and pig lungs", Journal of Applied Physiology 1971, 30: 99-115.
Yellin et al., "Percutaneous Tube Drainage: The Treatment of Choice for Refractory Lung Abscess", The Annals of Thoracic Surgery 1985; 39: 266-270.
Yim et al., "Minimally invasive thoracic surgery: where do we stand now?" Hong Kong Medical Journal 1995; 1: 115-122.
Yim et al., "Early results of endoscopic lung volume reduction for emphysema", The Journal of Thoracic and Cardiovascular Surgery 2004; 127: 1564-1573.
International Search Report for PCT/US/2009/034374 dated Aug. 28, 2009; 13 pages.

International Search Report for PCT/US/2009/034380 dated Sep. 24, 2009; 12 pages.
International Search Report for PCT/US2009/034322 dated Oct. 5, 2009; 14 pages.

International Search Report for PCT/US2009/034406 dated Dec. 2, 2009; 16 pages.

* cited by examiner

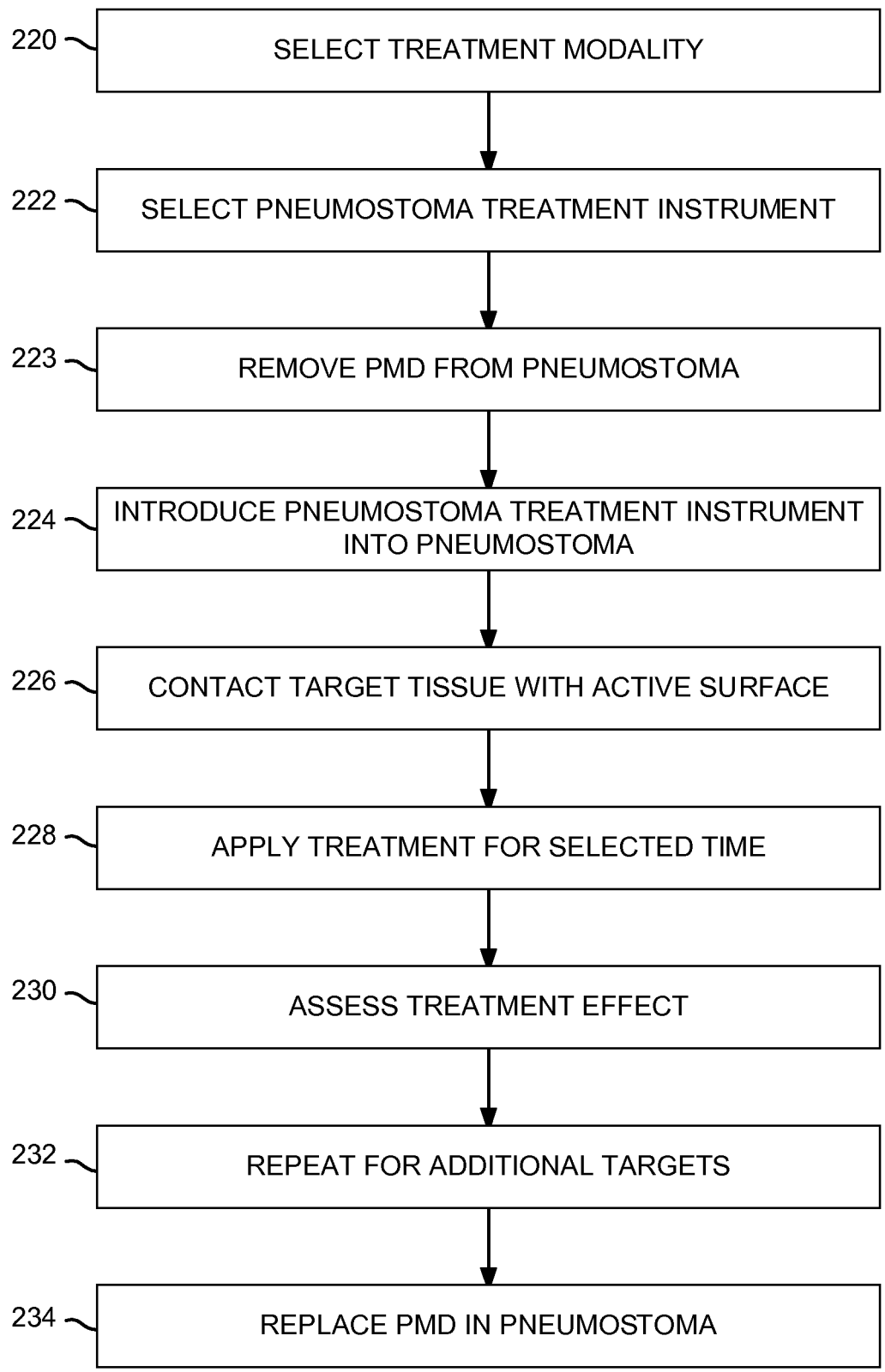

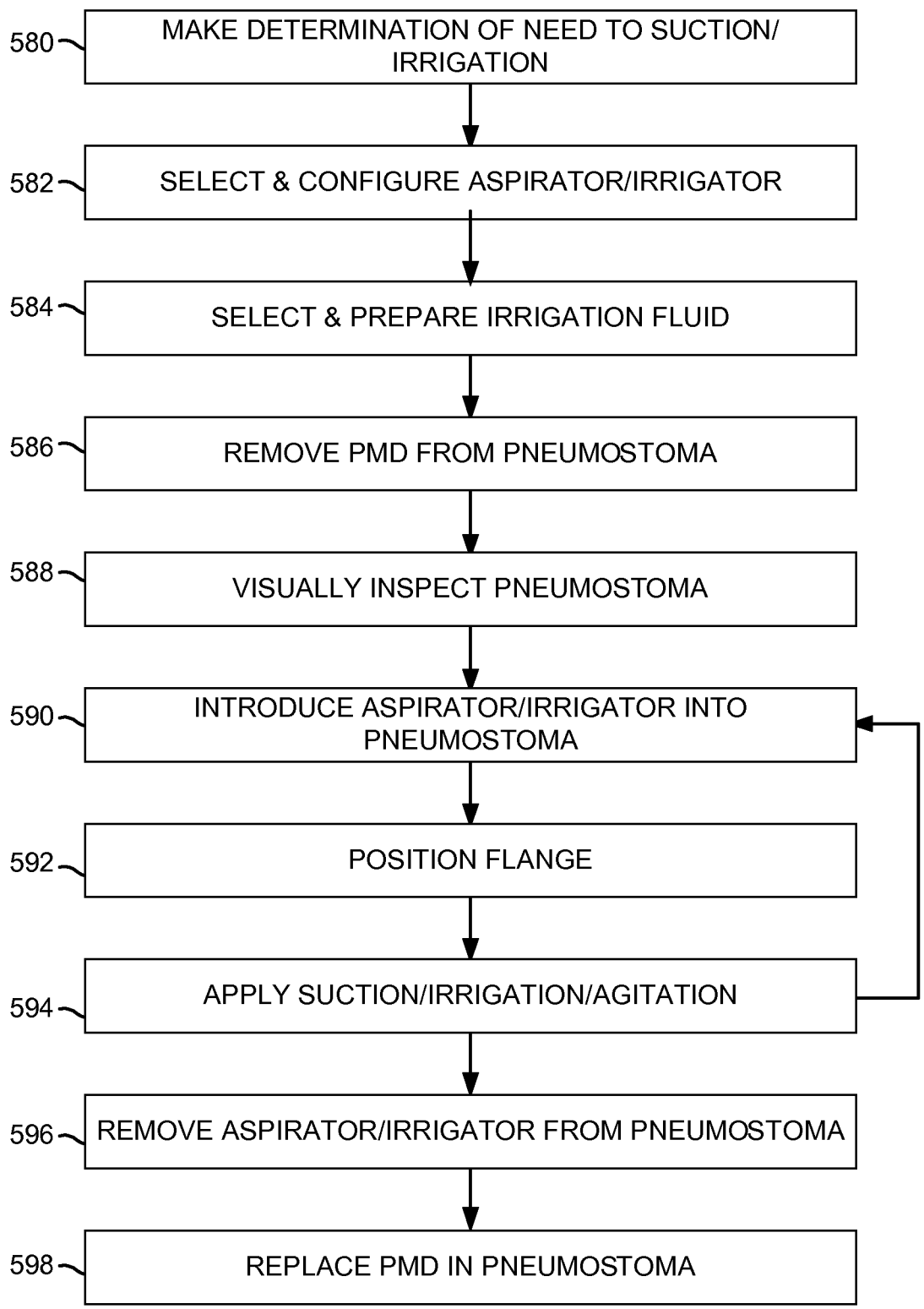

FIG. 7C
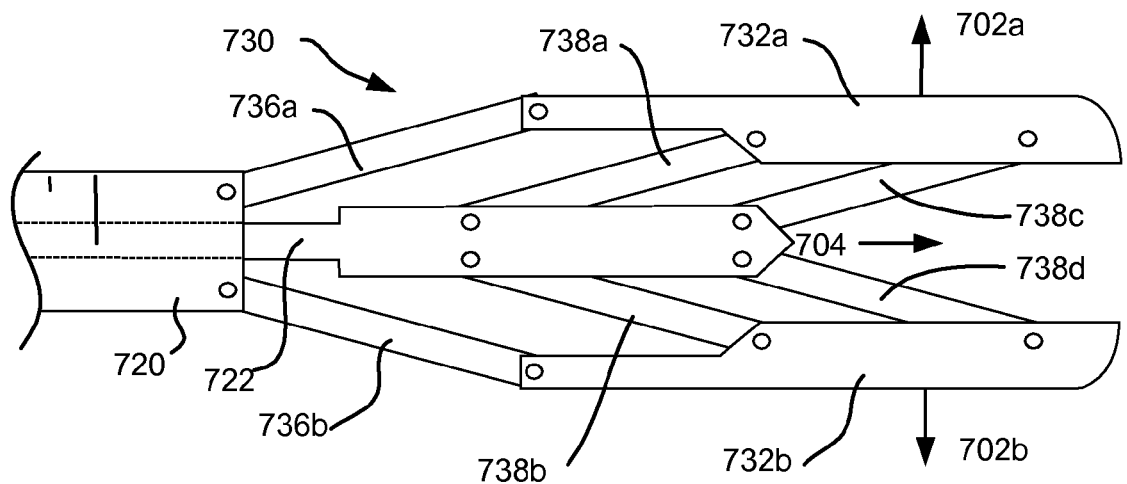
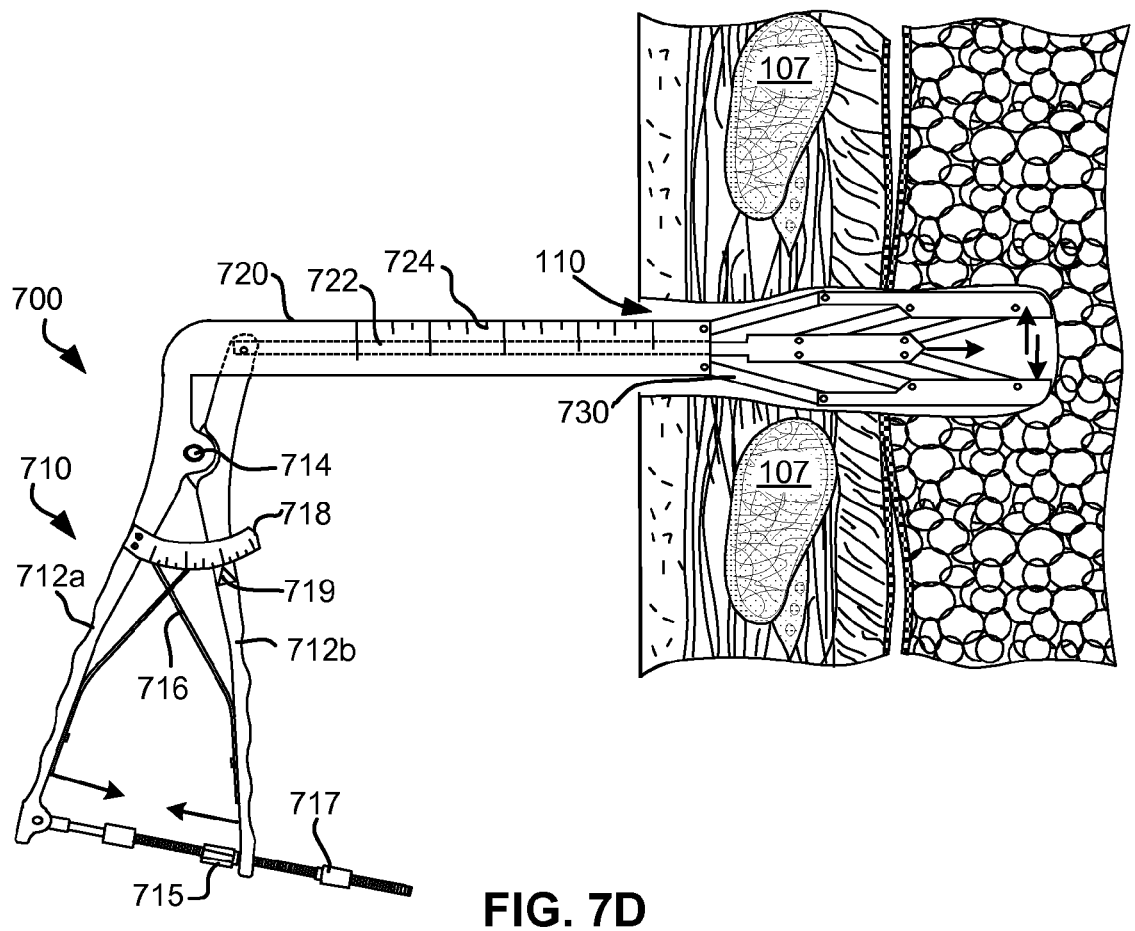
FIG. 7D

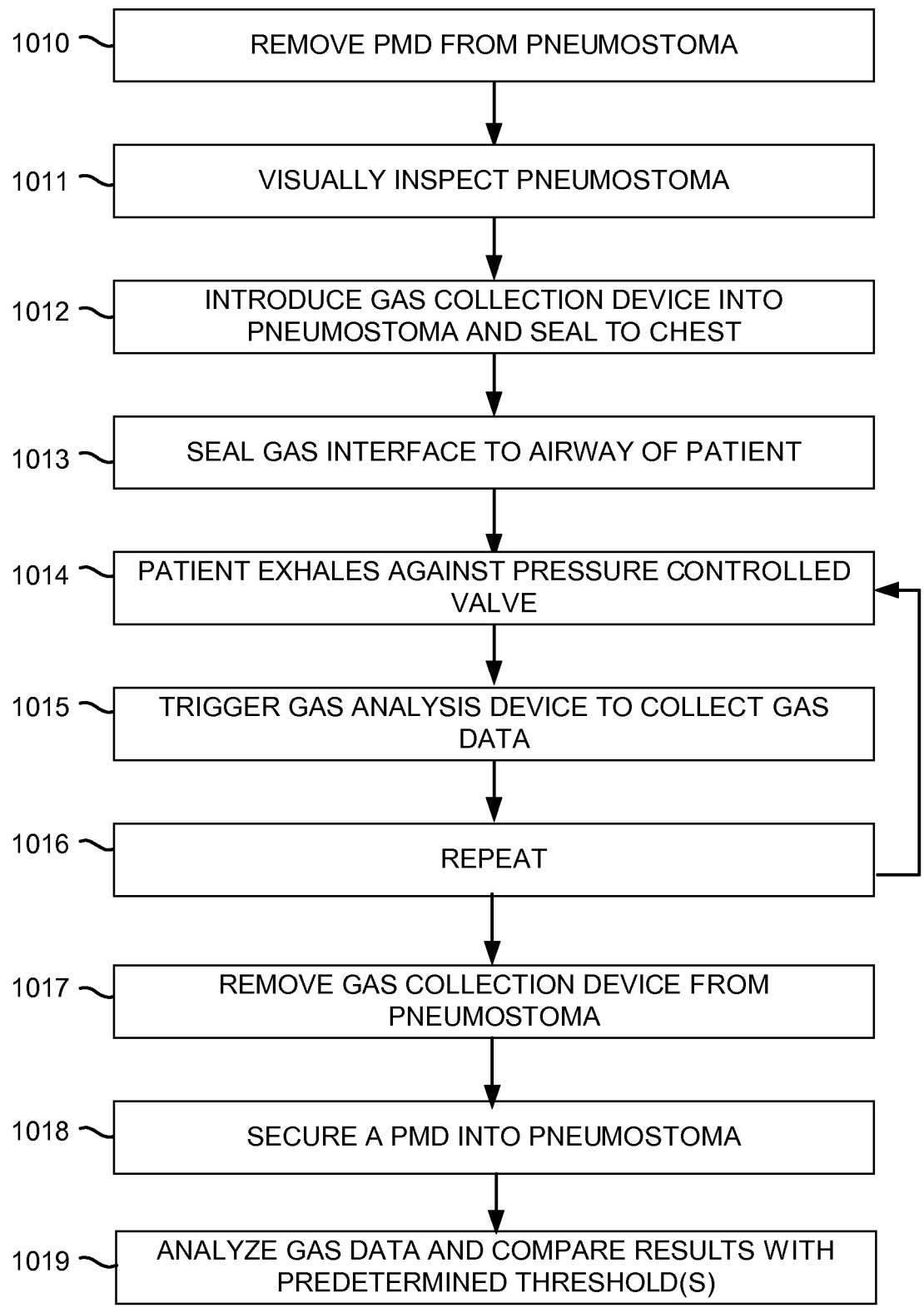

METHODS AND DEVICES FOR ASSESSMENT OF PNEUMOSTOMA FUNCTION

CLAIM TO PRIORITY

This application is a continuation-in-part application of U.S. patent application Ser. No. 12/388,459 entitled "METHODS AND DEVICES FOR FOLLOW-UP CARE AND TREATMENT OF A PNEUMOSTOMA" which application claims priority to all of the following applications including:

U.S. Provisional Application No. 61/029,830, filed Feb. 19, 2008, entitled "ENHANCED PNEUMOSTOMA MANAGEMENT DEVICE AND METHODS FOR TREATMENT OF CHRONIC OBSTRUCTIVE PULMONARY DISEASE";

U.S. Provisional Application No. 61/032,877, filed Feb. 29, 2008, entitled "PNEUMOSTOMA MANAGEMENT SYSTEM AND METHODS FOR TREATMENT OF CHRONIC OBSTRUCTIVE PULMONARY DISEASE";

U.S. Provisional Application No. 61/038,371, filed Mar. 20, 2008entitled "SURGICAL PROCEDURE AND INSTRUMENT TO CREATE A PNEUMOSTOMA AND TREAT CHRONIC OBSTRUCTIVE PULMONARY DISEASE";

U.S. Provisional Application No. 61/082,892, filed Jul. 23, 2008, entitled "PNEUMOSTOMA MANAGEMENT SYSTEM HAVING A COSMETIC AND/OR PROTECTIVE COVER";

U.S. Provisional Application No. 61/083,573, filed Jul. 25, 2008, entitled "DEVICES AND METHODS FOR DELIVERY OF A THERAPEUTIC AGENT THROUGH A PNEUMOSTOMA";

U.S. Provisional Application No. 61/084,559, filed Jul. 29, 2008, entitled "ASPIRATOR FOR PNEUMOSTOMA MANAGEMENT";

U.S. Provisional Application No. 61/088,118, filed Aug. 12, 2008, entitled "FLEXIBLE PNEUMOSTOMA MANAGEMENT SYSTEM AND METHODS FOR TREATMENT OF CHRONIC OBSTRUCTIVE PULMONARY DISEASE";

U.S. Provisional Application No. 61/143,298, filed Jan. 8, 2009, entitled "METHODS AND APPARATUS FOR THE CRYOTHERAPY CREATION OR RE-CREATION OF PNEUMOSTOMY"; and U.S. Provisional Application No. 61/151,581, filed Feb. 11, 2009, entitled "SURGICAL INSTRUMENTS AND PROCEDURES TO CREATE A PNEUMOSTOMA AND TREAT CHRONIC OBSTRUCTIVE PULMONARY DISEASE".

All of the afore-mentioned applications are incorporated herein by reference in their entireties.

CROSS-REFERENCE TO RELATED APPLICATIONS

This application is related to all of the above provisional applications and all the patent applications that claim priority thereto including:

U.S. patent application Ser. No. 12/388,465, filed Feb. 18, 2009, entitled "ENHANCED PNEUMOSTOMA MANAGEMENT DEVICE AND METHODS FOR TREATMENT OF CHRONIC OBSTRUCTIVE PULMONARY DISEASE";

U.S. patent application Ser. No. 12/388,447, filed Feb. 18, 2009, entitled "PNEUMOSTOMA MANAGEMENT SYSTEM AND METHODS FOR TREATMENT OF CHRONIC OBSTRUCTIVE PULMONARY DISEASE";

U.S. patent application Ser. No. 12/388,451, filed Feb. 18, 2009, entitled "PNEUMOSTOMA MANAGEMENT METHOD FOR TREATMENT OF CHRONIC OBSTRUCTIVE PULMONARY DISEASE";

U.S. patent application Ser. No. 12/388,435, filed Feb. 18, 2009, entitled "TWO-PHASE SURGICAL PROCEDURE FOR CREATING A PNEUMOSTOMA TO TREAT CHRONIC OBSTRUCTIVE PULMONARY DISEASE";

U.S. patent application Ser. No. 12/388,438, filed Feb. 18, 2009, entitled "ACCELERATED TWO-PHASE SURGICAL PROCEDURE FOR CREATING A PNEUMOSTOMA TO TREAT CHRONIC OBSTRUCTIVE PULMONARY DISEASE";

U.S. patent application Ser. No. 12/388,441, filed Feb. 18, 2009, entitled "SINGLE-PHASE SURGICAL PROCEDURE FOR CREATING A PNEUMOSTOMA TO TREAT CHRONIC OBSTRUCTIVE PULMONARY DISEASE";

U.S. patent application Ser. No. 12/388,446filed Feb. 18, 2009, entitled "PERCUTANEOUS SINGLE-PHASE SURGICAL PROCEDURE FOR CREATING A PNEUMOSTOMA TO TREAT CHRONIC OBSTRUCTIVE PULMONARY DISEASE";

U.S. patent application Ser. No. 12/388,453, filed Feb. 18, 2009, entitled "SURGICAL INSTRUMENTS FOR CREATING A PNEUMOSTOMA AND TREATING CHRONIC OBSTRUCTIVE PULMONARY DISEASE";

U.S. patent application Ser. No. 12/388,460, filed Feb. 13, 2009, entitled "PNEUMOSTOMA MANAGEMENT SYSTEM HAVING A COSTMETIC AND/OR PROTECTIVE COVER"

U.S. patent application Ser. No. 12/388,455 filed Feb. 18, 2009, entitled "DEVICES AND METHODS FOR DELIVERY OF A THERAPEUTIC AGENT THROUGH A PNEUMOSTOMA";

U.S. patent application Ser. No. 12/388,461, filed Feb. 18, 2009, entitled "ASPIRATOR FOR PNEUMOSTOMA MANAGEMENT";

U.S. patent application Ser. No. 12/388,462, filed Feb. 18, 2009, entitled "ASPIRATOR AND METHOD FOR PNEUMOSTOMA MANAGEMENT";

U.S. patent application Ser. No. 12/388,458, filed Feb. 18, 2009, entitled "FLEXIBLE PNEUMOSTOMA MANAGEMENT SYSTEM AND METHODS FOR TREATMENT OF CHRONIC OBSTRUCTIVE PULMONARY DISEASE";

U.S. patent application Ser. No. 12/388,459, filed Feb. 18, 2009, entitled "METHODS AND DEVICES FOR FOLLOW-UP CARE AND TREATMENT OF A PNEUMOSTOMA";

U.S. patent application Ser. No. 12/388,466, filed Feb. 18, 2009, entitled "ONE-PIECE PNEUMOSTOMA MANAGEMENT SYSTEM AND METHODS FOR TREATMENT OF CHRONIC OBSTRUCTIVE PULMONARY DISEASE";

U.S. patent application Ser. No. 12/388,467, filed Feb. 18, 2009, entitled "PNEUMOSTOMA MANAGEMENT SYSTEM WITH SECRETION MANAGEMENT FEATURES FOR TREATMENT OF CHRONIC OBSTRUCTIVE PULMONARY DISEASE";

U.S. patent application Ser. No. 12/388,468, filed Feb. 18, 2009, entitled "MULTI-LAYER PNEUMOSTOMA MANAGEMENT SYSTEM AND METHODS FOR TREATMENT OF CHRONIC OBSTRUCTIVE PULJMONARY DISEASE";

U.S. patent application Ser. No. 12/388,469, filed Feb. 18, 2009entitled "VARIABLE LENGTH PNEUMOSTOMA

MANAGEMENT SYSTEM FOR TREATMENT OF CHRONIC OBSTRUCTIVE PULMONARY DISEASE";

U.S. patent application Ser. No. 12/388,470, filed Feb. 18, 2009, entitled "SELF-SEALING DEVICE AND METHOD FOR DELIVERY OF A THERAPEUTIC AGENT THROUGH A PNEUMOSTOMA"; and U.S. patent application Ser. No. 12/704,452, filed Feb. 11, 2010, entitled "SURGICAL INSRUMENTS FOR CREATING A PNEUMOSTOMA AND TREATING CHRONIC OBSTRUCTIVE PULMONARY DISEASE".

All of the afore-mentioned applications are incorporated herein by reference in their entireties. This patent application also incorporates by reference all patents, applications, and articles discussed and/or cited herein.

BACKGROUND OF THE INVENTION

In the United States alone, approximately 14 million people suffer from some form of Chronic Obstructive Pulmonary Disease (COPD). However an additional ten million adults have evidence of impaired lung function indicating that COPD may be significantly underdiagnosed. The cost of COPD to the nation in 2002 was estimated to be $32.1 billion. Medicare expenses for COPD beneficiaries were nearly 2.5 times that of the expenditures for all other patients. Direct medical services accounted for $18.0 billion, and indirect cost of morbidity and premature mortality was $14.1 billion. COPD is the fourth leading cause of death in the U.S. and is projected to be the third leading cause of death for both males and females by the year 2020.

Chronic Obstructive Pulmonary Disease (COPD) is a progressive disease of the airways that is characterized by a gradual loss of lung function. In the United States, the term COPD includes chronic bronchitis, chronic obstructive bronchitis, and emphysema, or combinations of these conditions. In emphysema the alveoli walls of the lung tissue are progressively weakened and lose their elastic recoil. The breakdown of lung tissue causes progressive loss of elastic recoil and the loss of radial support of the airways which traps residual air in the lung. This increases the work of exhaling and leads to hyperinflation of the lung. When the lungs become hyperinflated, forced expiration cannot reduce the residual volume of the lungs because the force exerted to empty the lungs collapses the small airways and blocks air from being exhaled. As the disease progresses, the inspiratory capacity and air exchange surface area of the lungs is reduced until air exchange becomes seriously impaired and the individual can only take short shallow labored breaths (dyspnea).

The symptoms of COPD can range from the chronic cough and sputum production of chronic bronchitis to the severe disabling shortness of breath of emphysema. In some individuals, chronic cough and sputum production are the first signs that they are at risk for developing the airflow obstruction and shortness of breath characteristic of COPD. With continued exposure to cigarettes or noxious particles, the disease progresses and individuals with COPD increasingly lose their ability to breathe. Acute infections or certain weather conditions may temporarily worsen symptoms (exacerbations), occasionally where hospitalization may be required. In others, shortness of breath may be the first indication of the disease. The diagnosis of COPD is confirmed by the presence of airway obstruction on testing with spirometry. Ultimately, severe emphysema may lead to severe dyspnea, severe limitation of daily activities, illness and death.

There is no cure for COPD or pulmonary emphysema, only various treatments for ameliorating the symptoms. The goal of current treatments is to help people live with the disease more comfortably and to prevent the progression of the disease. The current options include: self-care (e.g., quitting smoking), therapeutic agents (such as bronchodilators which do not address emphysema physiology), long-term oxygen therapy, and surgery (lung transplantation and lung volume reduction surgery). Lung Volume Reduction Surgery (LVRS) is an invasive procedure primarily for patients who have a localized (heterogeneous) version of emphysema; in which, the most diseased area of the lung is surgically removed to allow the remaining tissue to work more efficiently. Patients with diffuse emphysema cannot be treated with LVRS, and typically only have lung transplantation as an end-stage option. However, many patients are not candidates for such a taxing procedure.

A number of less-invasive surgical methods have been proposed for ameliorating the symptoms of COPD. In one approach new windows are opened inside the lung to allow air to more easily escape from the diseased tissue into the natural airways. These windows are kept open with permanently implanted stents. Other approaches attempt to seal off and shrink portions of the hyperinflated lung using chemical treatments and/or implantable plugs. However, these proposals remain significantly invasive and are still in clinical trails. None of the surgical approaches to treatment of COPD has been widely adopted. Therefore, a large unmet need remains for a medical procedure that can sufficiently alleviate the debilitating effects of COPD and emphysema and is accepted by physicians and patients.

SUMMARY OF THE INVENTION

In view of the disadvantages of the state of the art, Applicants have developed a method for treating COPD in which an artificial passageway is made through the chest wall into the lung. An anastomosis is formed between the artificial passageway and the lung by pleurodesis between the visceral and parietal membranes surrounding the passageway as it enters the lung. The pleurodesis creates an adhesion between the pleural membrane surrounding the passageway which prevents air from entering the pleural cavity and causing a pneumothorax (deflation of the lung due to air pressure in the pleural cavity). Pleurodesis results from a fibrotic healing response between the pleural membranes and may be localized to the vicinity of the passageway. The artificial passageway through the chest wall also becomes epithelialized. The result is a stable artificial aperture through the chest wall which communicates with the parenchymal tissue of the lung.

The artificial aperture into the lung through the chest is referred to herein as a pneumostoma. The pneumostoma provides an extra pathway that allows air to exit the lung while bypassing the natural airways which have been impaired by COPD and emphysema. By providing this ventilation bypass, the pneumostoma allows the stale air trapped in the lung to escape from the lung thereby shrinking the lung (reducing hyperinflation). By shrinking the lung, the ventilation bypass reduces breathing effort, reduces expiratory pressures, reduces dyspnea, and allows more fresh air to be drawn in through the natural airways and increases the effectiveness of all of the tissues of the lung for gas exchange. Increasing the effectiveness of gas exchange allows for increased absorption of oxygen into the bloodstream and also increased removal of carbon dioxide. Reducing the amount of carbon dioxide retained in the lung reduces hypercapnia which also reduces dyspnea. The pneumostoma thereby achieves the advantages of lung volume reduction surgery without surgically removing or sealing off a portion of the lung or transplanting a lung.

The present invention provides methods and devices for assessing, and treating the health and functionality of a pneumostoma. Utilizing the methods and devices of the present invention a physician can enhance the health, patency and/or effectiveness of a pneumostoma thereby enhancing the remediation of COPD. Other objects, features and advantages of the invention are apparent from drawings and detailed description to follow.

BRIEF DESCRIPTION OF THE DRAWINGS

The above and further features, advantages and benefits of the present invention are apparent upon consideration of the present description taken in conjunction with the accompanying drawings.

FIG. 2B is a flow chart illustrating general steps for follow-up care and treatment of a patient having a pneumostoma according to an embodiment of the invention.

FIG. 5D is a flow chart illustrating steps for treatment of a pneumostoma with suction, irrigation and/or lavage according to an embodiment of the invention.

FIGS. 7A-7D show views of a mechanical instrument for dilating the pneumostoma or a portion of the pneumostoma according to an embodiment of the present invention.

FIG. 10C provides steps of a method for using the diagnostic systems of FIGS. 10A and 10B according to an embodiment of the present invention.

DETAILED DESCRIPTION OF THE INVENTION

Figure 1A:
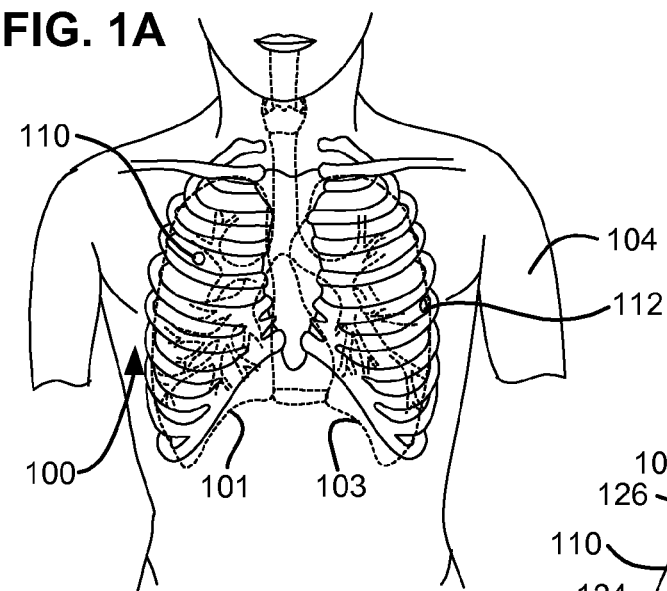
FIG. 1A shows the chest of a patient indicating alternative locations for a pneumostoma that may be managed using the devices and methods of the present invention.

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators are used to refer to like parts or elements throughout. In addition, the first digit of a reference number identifies the drawing in which the reference number first appears.

Pneumostoma Formation and Anatomy

FIG. 1A shows the chest of a patient identifying alternative locations for creating a pneumostoma that may be managed using the system of the present invention. A first pneumostoma 110 is shown on the front of the chest 100 over the right lung 101 (shown in dashed lines). The pneumostoma is preferably positioned over the third intercostal space on the midclavicular line. Thus the pneumostoma 110 is located on the front of the chest between the third and fourth ribs. Although the pneumostoma 110 is preferably located between two ribs, in alternative procedures a pneumostoma can also be prepared using a minithoracotomy with a rib resection.

In FIG. 1A a second pneumostoma 112 is illustrated in a lateral position entering the left lung 103 (shown in dashed lines). The pneumostoma 112 is preferably positioned over the fourth or fifth intercostal space under the left arm 104. In general, one pneumostoma per lung is created; however, more or less than one pneumostoma per lung may be created depending upon the needs of the patient. In most humans, the lobes of the lung are not completely separate and air may pass between the lobes. The upper lobe is the preferred location for a pneumostoma as the upper lobe tends to move less during breathing. However depending upon the patient, it may be desirable to position a pneumostoma in any one of the lobes of the lung including the lower lobes.

A pneumostoma is surgically created by forming an artificial channel through the chest wall and joining that channel with an opening through the visceral membrane of the lung into parenchymal tissue of the lung to form an anastomosis. The anastomosis is joined and sealed by sealing the channel from the pleural cavity using adhesives, mechanical sealing and/or pleurodesis.

Figure 1B:
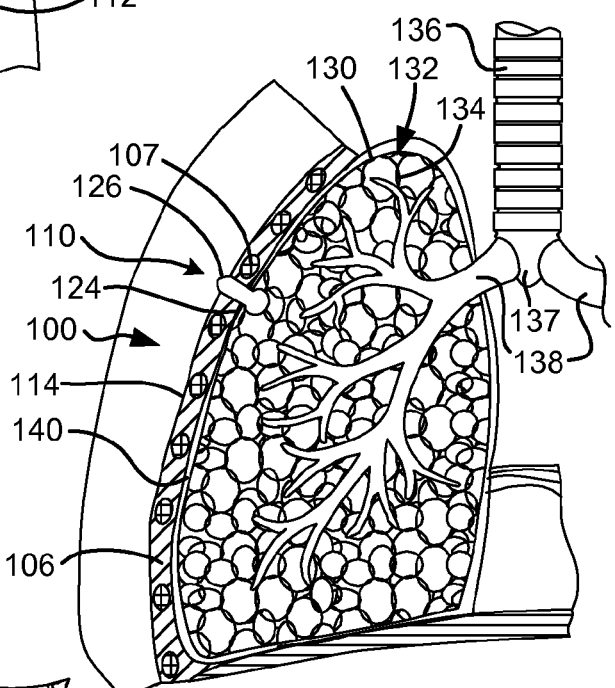
FIG. 1B shows a sectional view of the chest illustrating the relationship between the pneumostoma, lung and natural airways.

FIG. 1B shows a sectional view of chest 100 illustrating the position of the pneumostoma 110. The parenchymal tissue 132 of the lung 130 is comprised principally of alveoli 134. The alveoli 134 are the thin walled air-filled sacs in which gas exchange takes place. Air flows into the lungs through the natural airways including the trachea 136, carina 137, and bronchi 138. Inside the lungs, the bronchi branch into a multiplicity of smaller vessels referred to as bronchioles (not shown). Typically, there are more than one million bronchioles in each lung. Each bronchiole connects a cluster of alveoli to the natural airways. As illustrated in FIG. 1B, pneumostoma 110 comprises a channel through the thoracic wall 106 of the chest 100 between two ribs 107. Pneumostoma 110 opens at an aperture 126 through the skin 114 of chest 100.

Figure 1C:
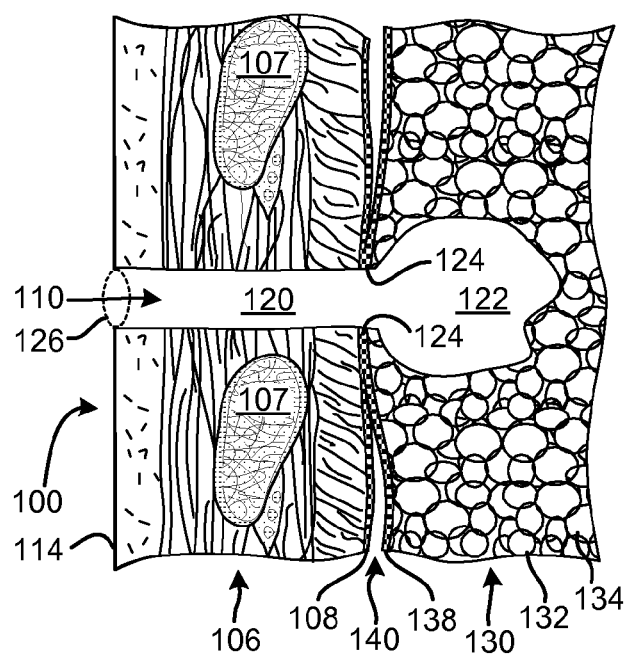
FIG. 1C shows a detailed sectional view of a pneumostoma.

FIG. 1C shows a detailed sectional view of the pneumostoma 110. As illustrated in FIG. 1C, pneumostoma 110 comprises a channel 120 through the thoracic wall 106 of the chest 100 between the ribs 107. The channel 120 is joined to cavity 122 in the parenchymal tissue 132 of lung 130. The cavity 122 will typically conform to the shape of the device inserted into the pneumostoma 110. An adhesion or pleurodesis 124 surrounds the channel 120 where it enters the lung 130. The thoracic wall 106 is lined with the parietal membrane 108. The surface of the lung 130 is covered with a continuous sac called the visceral membrane 138. The parietal membrane 108 and visceral membrane 138 are often referred to collectively as the pleural membranes. Between the parietal membrane 108 and visceral membrane 138 is the pleural cavity (pleural space) 140. The pleural cavity usually only contains a thin film of fluid that serves as a lubricant between the lungs and the chest wall. In pleurodesis 124 the pleural membranes are fused and/or adhered to one another eliminating the space between the pleural membranes in that region.

An important feature of the pneumostoma is the seal or adhesion 124 surrounding the channel 120 where it enters the lung 130 which may be formed by pleurodesis. Pleurodesis creates a fusion or adhesion 124 of the parietal membrane 108 and visceral membrane 138. A pleurodesis may be a complete pleurodesis in which the entire pleural cavity 140 is removed by fusion of the visceral membrane 138 with the parietal membrane 108 over the entire surface of the lung 130. However, as shown in FIG. 1C, the adhesion 124 is preferably localized to the region surrounding the channel 120. The adhesion 124 surrounding the channel 120 prevents air from entering the pleural cavity 140. If air is permitted to enter pleural cavity 140, a pneumothorax will result and the lung may collapse.

Adhesion 124 can be created between the visceral pleura of the lung and the inner wall of the thoracic cavity using chemical methods including introducing into the pleural space irritants such as antibiotics (e.g. Doxycycline or Quinacrine), antibiotics (e.g. iodopovidone or silver nitrate), anticancer therapeutic agents (e.g. Bleomycin, Mitoxantrone or Cisplatin), cytokines (e.g. interferon alpha-2β and Transforming growth factor-β); pyrogens (e.g. *Corynebacterium parvum*, *Staphylococcus aureus* superantigen or OK432); connective tissue proteins (e.g. fibrin or collagen) and minerals (e.g. talc slurry). Pleurodesis can also be performed using surgical methods including pleurectomy. For example, the pleural space may be mechanically abraded during thoracoscopy or thoracotomy. This procedure is called dry abrasion pleurodesis. A pleurodesis may also be formed using radiotherapy methods, including radioactive gold or external radiation. These methods cause an inflammatory response and or fibrosis, healing, and fusion of the pleural membranes. Alternatively, a seal can be created in an acute manner between the pleural membranes using biocompatible glues, meshes or mechanical means such as clamps, staples, clips and/or sutures. The adhesive or mechanical seal may develop cause pleurodesis over time. A range of biocompatible glues are available that may be used on the lung, including light-activatable glues, fibrin glues, cyanoacrylates and two part polymerizing glues.

When formed, pneumostoma 110 provides an extra pathway for exhaled air to exit the lung 130 reducing residual volume and intra-thoracic pressure without the air passing through the major natural airways such as the bronchi 138 and trachea 136. Collateral ventilation is particularly prevalent in an emphysemous lung because of the deterioration of lung tissue caused by COPD. Collateral ventilation is the term given to leakage of air through the connective tissue between the alveoli 134. Collateral ventilation may include leakage of air through pathways that include the interalveolar pores of Kohn, bronchiole-alveolar communications of Lambert, and interbronchiolar pathways of Martin. This air typically becomes trapped in the lung and contributes to hyperinflation. In lungs that have been damaged by COPD and emphysema, the resistance to flow in collateral channels (not shown) of the parenchymal tissue 132 is reduced allowing collateral ventilation to increase. Air from alveoli 134 of parenchymal tissue 132 that passes into collateral pathways of lung 130 is collected in cavity 122 of pneumostoma 110. Pneumostoma 110 thus makes use of collateral ventilation to collect air in cavity 122 and vent the air outside the body via channel 120 reducing residual volume and intra-thoracic pressure and bypassing the natural airways which have been impaired by COPD and emphysema. Cavity 122 will typically conform/adapt to the size and shape of the device inserted into the pneumostoma.

By providing this ventilation bypass, the pneumostoma allows stale air trapped in the parenchymal tissue 132 to escape from the lung 130. This reduces the residual volume and intra-thoracic pressure. The lower intra-thoracic pressure reduces the dynamic collapse of airways during exhalation. By allowing the airways to remain patent during exhalation, labored breathing (dyspnea) and residual volume (hyperinflation) are both reduced. Pneumostoma 110 not only provides an extra pathway that allows air to exit the lung 130 but also allows more fresh air to be drawn in through the natural airways. This increases the effectiveness of all of the tissues of the lung 130 and improves gas exchange. Pneumostoma 110 thus achieves many of the advantages sought by lung volume reduction surgery without surgically removing a portion of the lung or sealing off a portion of the lung.

Methods and instruments for forming the channel, opening, anastomosis and pleurodesis are disclosed in applicant's pending and issued patents and applications including those related cases incorporated by reference above.

Pneumostoma Management Device

Figure 1D:
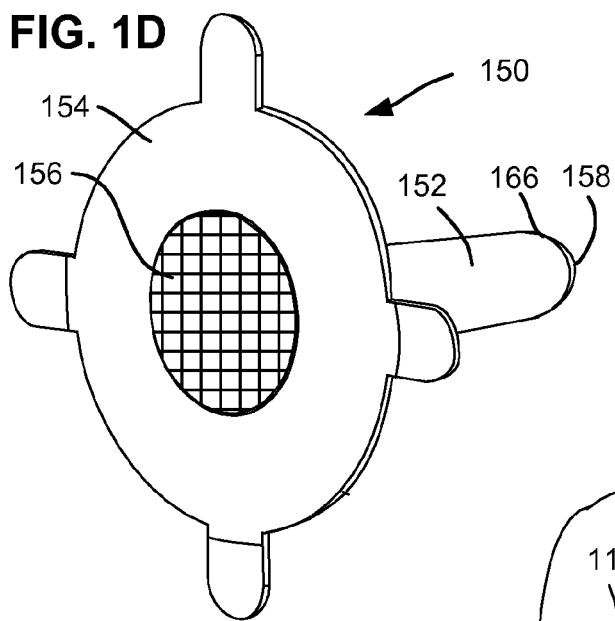
FIG. 1D shows a perspective view of a pneumostoma management device.
Figure 1E:
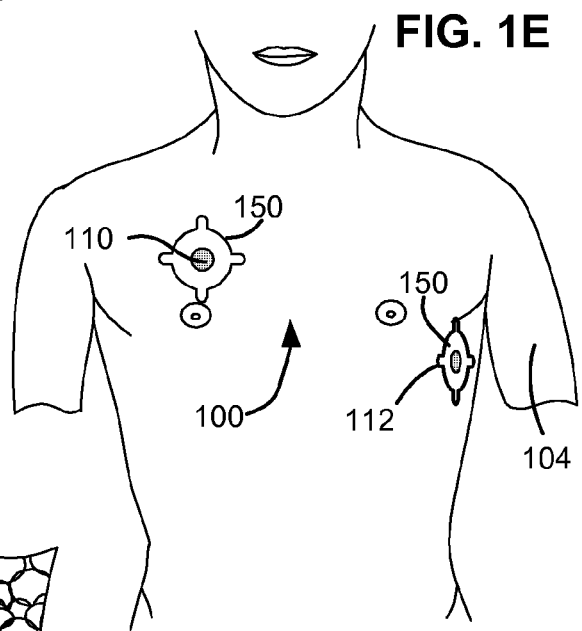
FIG. 1E shows the chest of a patient showing the pneumostoma management device positioned at alternative pneumostoma locations.
Figure 1F:
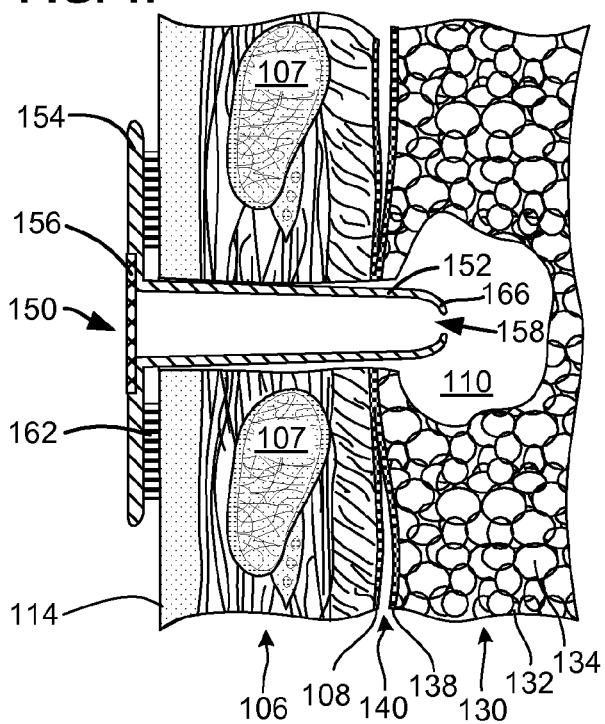
FIG. 1F shows a detailed sectional view of a pneumostoma management device positioned inside a pneumostoma.

As described above, a pneumostoma may be created to treat the symptoms of chronic obstructive pulmonary disease. A patient is typically provided with a pneumostoma management system to protect the pneumostoma and keeps the pneumostoma open on a day-to-day basis. In general terms a pneumostoma management device ("PMD") comprises a tube which is inserted into the pneumostoma and an external component which is secured to the skin of the patient to keep the tube in place. Gases escape from the lung through the tube and are vented external to the patient. The pneumostoma management device may, in some, but not all cases, include a filter which only permits gases to enter or exit the tube. The pneumostoma management device may, in some, but not all cases, include a one-way valve which allows gases to exit the lung but not enter the lung through the tube. FIGS. 1D, 1E and 1F show an example of pneumostoma management device ("PMD") 150. FIG. 1D shows a perspective view of PMD 150. FIG. 1E shows a view of the chest of a patient showing PMD 150 positioned in pneumostomas. FIG. 1F shows a sectional view of PMD 150 positioned within pneumostoma 110.

Referring to FIG. 1D, PMD 150 includes a vent tube 152, a flange 154 and a filter 156. Filter 156 prevents liquid and solid discharge from leaking out of the PMD and such discharge is trapped inside the pneumostoma or vent tube until the PMD is removed and replaced. Filter 156 also prevents the entry of contaminants into the pneumostoma. Filter 156 is preferably a hydrophobic filter to prevent leakage of fluids into or out of the pneumostoma. Flange 154 has an adhesive coating 162 (not shown) on the distal side. The adhesive coating 162 temporarily secures flange 154 to the skin 114 of the patient. Flange 154 also prevents over insertion of vent tube 152 by providing a mechanical stop to further insertion.

As shown in FIGS. 1E and 1F, during use, the vent tube 152 of PMD 150 is pushed into the pneumostoma 110. The vent tube is configured to fit into a pneumostoma to keep the pneumostoma open. Gases from the lung enter an opening 158 in the distal end of vent tube 152. Vent tube 152 is sized so as to pass through the thoracic wall into a portion of the pneumostoma 110 within the lung 130 as shown in FIG. 1F. However, vent tube 152 but is not so long that it causes damage to the parenchymal tissue 132 of the lung 130. Vent tube 152 is preferably rounded over to provide an atraumatic tip 166 at the distal end. A patient is provided with a PMD having a vent tube 152 of the appropriate length for their pneumostoma. When the patient exhales, the pressure inside the chest is above atmospheric pressure and gases are consequently pushed through the central lumen of vent tube 152 and out through filter 156. Additional details and variations of pneumostoma management devices are described in applicant's pending and issued patents and applications including those related cases incorporated by reference above.

Pneumostoma Follow-Up Care

The patient is typically responsible for day-to-day management of the pneumostoma including replacement of the PMD and whatever daily cleaning and skin care may be required. In preferred embodiments, the PMD is a disposable unit which is changed on a daily basis or as needed. While changing the PMD, the patient and/or caregiver can clean the skin surrounding the pneumostoma and observe the condition of the pneumostoma.

A patient with a pneumostoma is also under the care of a physician and undergoes periodic checkups to monitor the condition of their lungs and of the pneumostoma. Moreover, the patient is advised to visit the physician if certain conditions are observed. The patient therefore visits the physician for regular follow-up visits and as indicated by observed conditions. The patient will also preferably be enrolled in a pulmonary rehabilitation program which will include: medical evaluation and management including monitoring patient compliance with pneumostoma care procedures; setting short term and long-term exercise goals; therapy programs (including smoking cessation if necessary); evaluation; and exercise. The rehabilitation program can also monitor the pneumostoma and refer the patient for assessment and treatment of the pneumostoma where indicated.

Figure 2A:
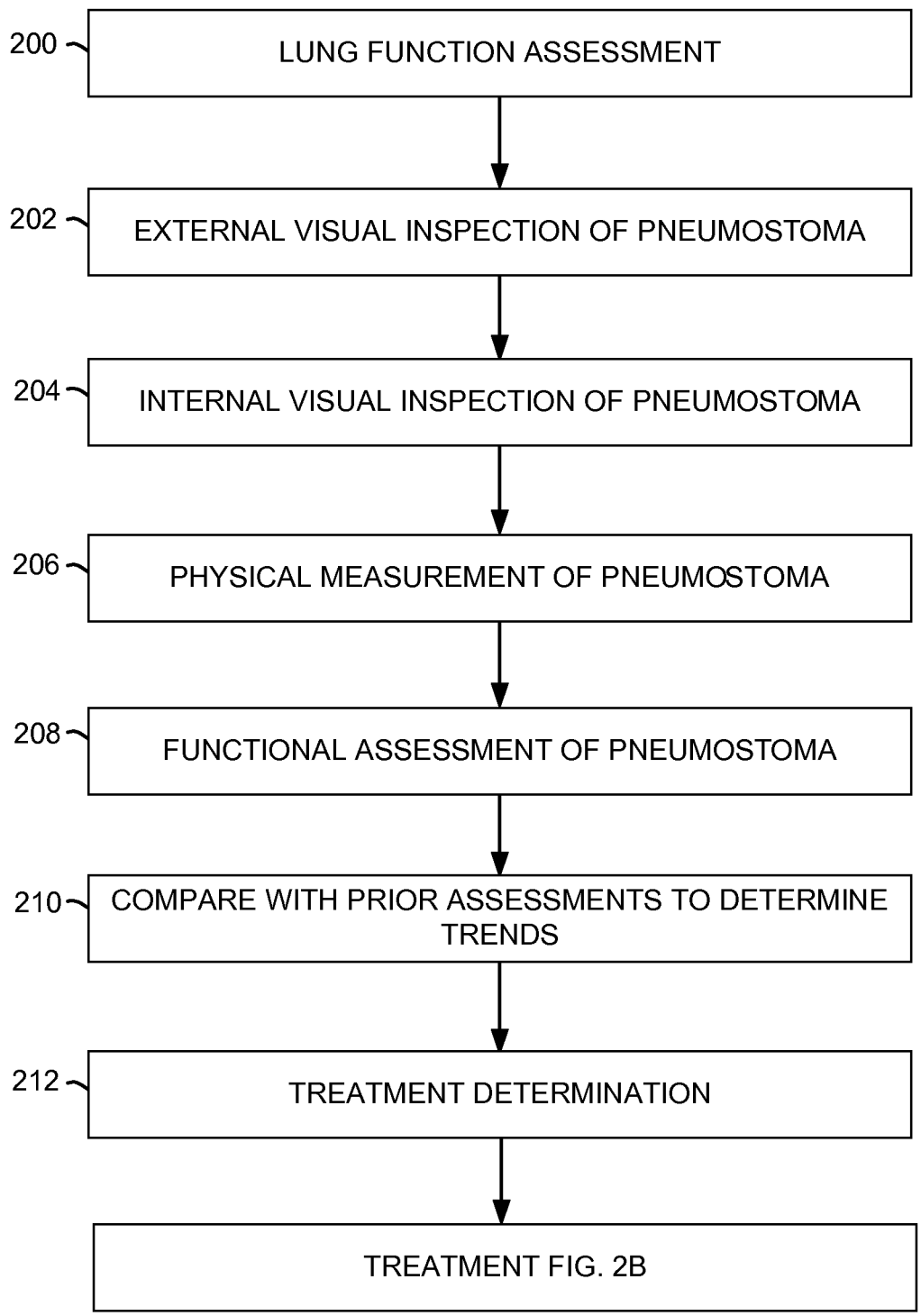
FIG. 2A is a flow chart illustrating general steps for follow-up care and assessment of a patient having a pneumostoma according to an embodiment of the invention.

The present invention provides a number of methods and devices for pneumostoma assessment and treatment. Such assessment and treatment is typically carried by a medical professional, for example a physician, nurse, respiratory therapist and/or medical assistant (this patent will use the term physician to include other medical care providers). FIG. 2A shows general assessment steps that may be performed when a patient visits a physician. The physician will typically assess the lung function of the patient (step 200). The physician will also assess each pneumostoma of the patient. The assessment of the pneumostoma may include one or more of an external visual inspection of the pneumostoma (step 202), an internal visual inspection of the pneumostoma (step 204); physical measurement of the pneumostoma (step 206), and a functional assessment of the pneumostoma (step 208). The results of the assessments may be compared with standard results and with prior assessments of the patient (step 210) to determine trends and variations in the lung/pneumostoma function. Based on the assessment of the lung function and pneumostoma, the physician determines whether any follow-up assessments and/or treatments are required (step 212).

The assessment of lung function (step 200) is performed as is typically done for COPD and emphysema patients. Such assessment may utilize one or more of: patient questionnaire/self reporting, spirometry (pre-/post-bronchodilator), pulmonary function test (lung volumes), diffusion capacity (DLLO), and arterial blood gas measurement.

In the external visual inspection (step 202) the physician examines the opening to the pneumostoma and the skin of the chest surrounding the pneumostoma. The physician observes any irritation, inflammation or infection and remediates where necessary. In the internal visual inspection (step 204) the physician examines the inside of the pneumostoma. The physician may use a pneumostoma inspection instrument.

The pneumostoma inspection instrument includes a short inspection tube that may be pushed into the pneumostoma and that provides illumination and magnification for observation of the interior of the pneumostoma. The observation may be achieved using a direct optical train or a video device which displays images on a video display. The pneumostoma inspection instrument is typically provided with a range of inspection tubes of different diameters and lengths. The physician chooses the inspection tube appropriate to the dimensions of the pneumostoma of the patient and is careful not to damage tissue of the pneumostoma during insertion. During the internal visual inspection the physician observes any irritation, inflammation or infection and remediates where necessary. The physician also makes a qualitative assessment of tissues surrounding the pneumostoma to determine encroachment to the pneumostoma. The physician may also use the pneumostoma inspection instrument to measure the diameter and length of the pneumostoma and the shape and/or profile of the pneumostoma. (step 206). These may be used to determine the size of any pneumostoma management device prescribed to the patient and the size of any instruments to be used during treatment of the pneumostoma. This step also allows the physician to monitor any tissue encroachment into the pneumostoma as indicated by change in dimensions of the pneumostoma over time.

In the functional assessment of the pneumostoma (step 208) the physician examines the ability of gas to pass through the pneumostoma. The ability of gas to pass through the pneumostoma may be measured in a number of ways. First, gas flow through the pneumostoma can be measured passively by placing a device over the pneumostoma which measures airflow out of and/or into the pneumostoma during regular breathing of the patient. Alternatively, gas may be provided to the pneumostoma at a slight positive pressure from outside the chest of the patient and the rate of flow of gas into the lung through the pneumostoma may be measured. Alternatively, as discussed below, diagnostic gases may be introduced through the pneumostoma to assess the patency and functionality of the pneumostoma. The diagnostic gases may be used for imaging the lungs and/or measuring collateral ventilation and gas exchange. The physician may compare the results of the visual, functional and/or structural assessment with prior assessment results and standard assessment results to determine changes and or trends in the results (step 210).

Based upon the results of the visual, functional and/or structural assessment of the pneumostoma and any trends in such results, the physician may decide to treat the pneumostoma and/or surrounding tissues to maintain or enhance the pneumostoma (step 212). The physician will select from the available treatment modalities a treatment suitable to maintain and/or enhance the function of the pneumostoma in light of the assessment results. (see step 220 of FIG. 2B). One or more treatment modalities may be used.

FIG. 2B illustrates a general method for treatment of a pneumostoma. First, based on the assessment results, the physician selects a treatment modality to maintain or enhance the health and/or functionality of the pneumostoma (step 220). For example, suction may be used to aspirate discharge or other materials from the pneumostoma. Irrigation/lavage may be used to introduce a liquid into the pneumostoma in order to treat the tissue or aid in the removal of material from the pneumostoma. Irrigation/lavage may be used in conjunction with suction/aspiration to remove the liquid. Suction and/or irrigation may also be used in conjunction with a mechanical cleaning mechanism such as soft bristles, mechanical agitation, sonic/ultrasonic agitation or the like. The pneumostoma may be mechanically expanded using a balloon dilator, mechanical dilator or other tools. The pneumostoma may additionally be treated with heat, cold, light, electromagnetic radiation, electrocautery, sound/ultrasound, and the like.

The physician next selects a pneumostoma treatment instrument suitable to apply the treatment modality to the pneumostoma (step 222). The selected instrument is preferably sized such that it can be introduced into the pneumostoma and placed at a desired depth in the pneumostoma. As pneumostomas may vary in size, the instrument may have a configurable size, or may have a range of different adapters. Thus selection of the instrument will include selecting an instrument appropriate for the treatment modality and selecting/configuring the instrument for the pneumostoma of a particular patient.

The selected/configured instrument is introduced into the pneumostoma (step 224). In most cases, the pneumostoma management device will need to be removed (step 223) prior to inserting the treatment device. In some cases, the treatment modality requires contact of a target tissue with a treatment surface of the device (step 226). In other cases, the instrument treats the entire pneumostoma. The treatment is applied for a selected time (step 228). The effect of the treatment may then be assessed (step 230). In some cases the effect of the treatment is assessed with the pneumostoma treatment instrument. In other cases the pneumostoma treatment instrument may be removed and replaced with a pneumostoma inspection instrument to permit the assessment. The treatment may then be repeated if and as necessary for the pneumostoma or additional targets within the pneumostoma (step 232) until the desired effects have been achieved. After the treatment is over a new pneumostoma management device should be promptly and correctly positioned in the pneumostoma either by the physician, or by the patient under the observation of the physician (step 234). Particular instruments suitable for assessing and treating pneumostomas in accordance with the general method steps of FIGS. 2A and 2B are described below.

Pneumostoma Assessment Instruments and Methods

To observe the interior of the pneumostoma the physician uses a pneumostoma inspection instrument placed within the pneumostoma. One type of pneumostoma inspection instrument includes a light source for illuminating the interior of the pneumostoma and a visualization system for visualizing (and typically magnifying) the interior of the pneumostoma. The visualization system may be a direct optical system comprising one or more optical components for providing a magnified image at an object lens mounted to the instrument. Alternatively, the visualization system may include means for obtaining a video image of the pneumostoma tissues and means for displaying the image, for example a video sensor and a video display. Such a pneumostoma inspection instrument, using a light source and visualization system, is referred to generally herein as a pneumoscope.

A pneumoscope may include a short inspection tube or speculum that may be pushed into the pneumostoma. The speculum holds open the pneumostoma during the inspection. The speculum may in some cases be a detachable metal speculum which may be sterilized between uses. Preferably, however, the speculum is disposable or covered with a disposable sleeve during use. The speculum may be provided in a range of different diameters and lengths as appropriate for a particular pneumostoma or patient. The physician chooses the speculum appropriate to the dimensions of the pneumostoma of the patient. The speculum may be provided with visible exterior markings so that the physician may gauge the depth of insertion of the speculum. The speculum may be provided with a flange which prevents over-insertion of the speculum—however the depth of insertion is typically under the control of the physician who should use care not to damage tissue of the pneumostoma during insertion. The physician may use the speculum to gauge the diameter, length and profile of the pneumostoma.

Figure 3A:
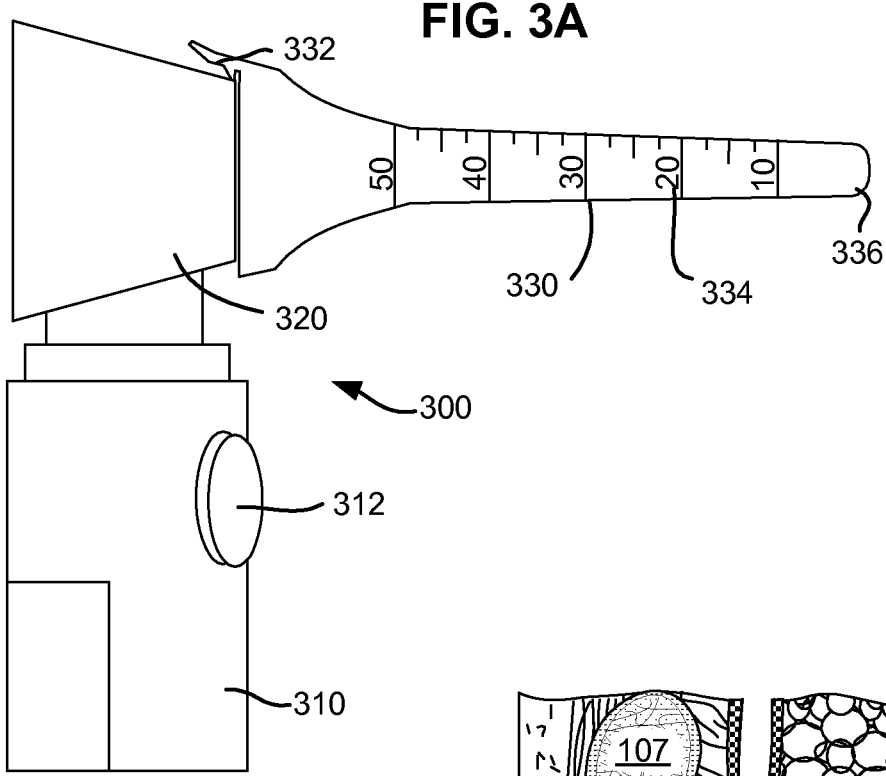
FIG. 3A shows an exterior view of an instrument for internal inspection of a pneumostoma according to an embodiment of the invention.
Figure 3B:
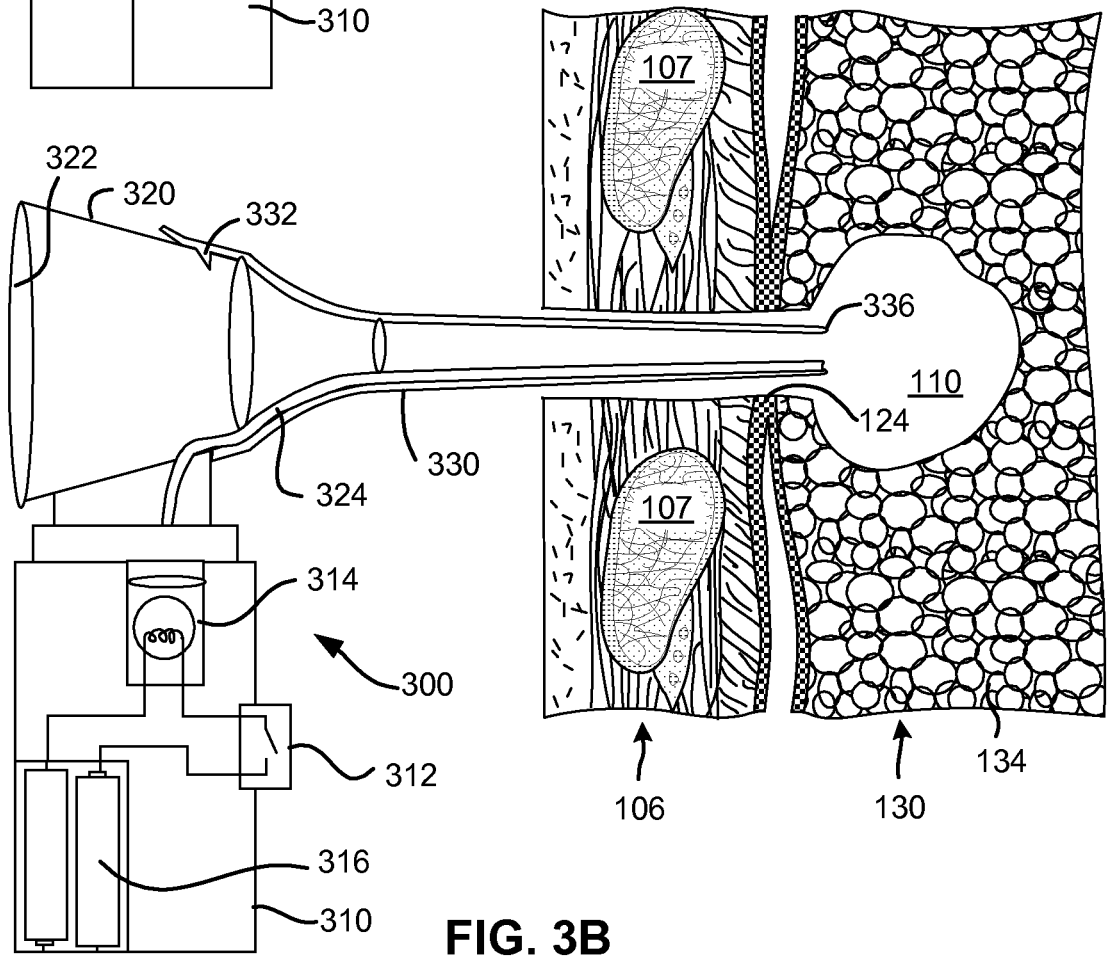
FIG. 3B shows a sectional view of the instrument for internal inspection of a pneumostoma of FIG. 3A positioned within a pneumostoma.

FIGS. 3A and 3B show an example of a pneumoscope according to one embodiment of the present invention. FIG. 3A shows an external view of a pneumoscope 300. FIG. 3B shows a sectional view of the pneumoscope positioned within a pneumostoma. As shown in FIG. 3A, pneumoscope 300 comprises a handle 310 and a head 320. A button 312 may be provided on handle 310 by which a physician may activate the light source and/or any image capturing system. A disposable speculum 330 is attached to head 320. Speculum 330 comprises a catch 332 at the proximal end for temporarily mounting speculum 330 to head 320 of pneumoscope 300. Speculum 330 is long enough to reach the end of a pneumostoma. As shown in FIG. 3A, speculum 330 bears external markings 334 indicating how far the distal tip 336 has travelled into the pneumostoma. External markings 334 may also be used to measure the depth of a pneumostoma. Pneumoscope 300 is preferably wireless and portable for ease of use.

As shown in FIG. 3B, handle 310 includes a light source 314 and power supply 316. In use, the distal tip 336 of speculum 330 is inserted into the pneumostoma 110. The physician actuates light source 314 to illuminate the interior of the pneumostoma 110. Light is directed from light source 314 to the pneumostoma 110 using an optical train 324 including e.g. fiber optics and/or lenses. The optical train 324 preferably provides uniform illumination of the field of view. In the embodiment of FIG. 3A, the head 320 comprises optics for viewing and magnifying the interior of the pneumostoma 110. The interior of the pneumostoma 110 may be observed by the physician through objective lens 322 within head 320. As shown in FIG. 3B, speculum 330 may be open at the distal tip 336. In alternative embodiments, distal tip 336 may be closed so long as a transparent window is provided through which the physician may observe the interior of the pneumostoma.

Figure 3C:
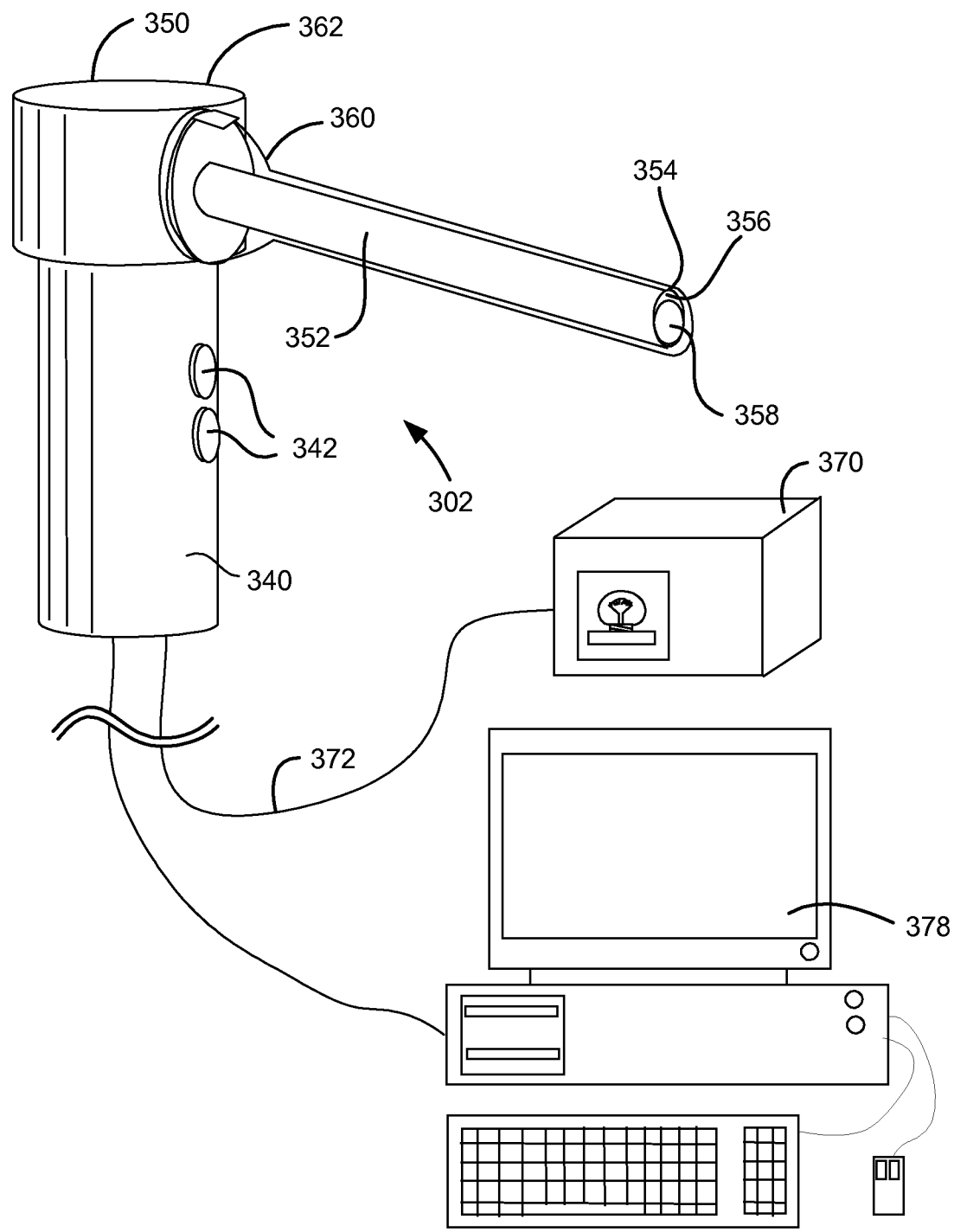
FIG. 3C shows an exterior view of an alternative instrument for internal inspection of a pneumostoma according to an embodiment of the invention.

FIG. 3C shows an alternative embodiment of a pneumoscope 302 comprising a handle 340 and a head 350. One or more buttons 342 may be provided on handle 340 by which a physician may activate the light source 370 and/or any image capturing system. A disposable cover 360 is attached to head 350. Cover 360 comprises a catch 362 at the proximal end for temporarily mounting cover 360 to head 350 of pneumoscope 302. Cover 360 protects an extension 352 of head 350. Extension 352 and cover 360 are long enough to reach the end of a pneumostoma. Cover 360 may be provided with external markings (not shown) indicating how far the distal tip 354 has travelled into a pneumostoma. Pneumoscope 302 is attached to a remote light source 370 and remote display system 378. Remote display system 378 may include an image capturing system to record video images of the pneumostoma.

Light source 370 provides light which is transmitted by a fiber optic cable 372 to the distal tip 354 of extension 352. A window 356 emits light to illuminate the field of view. A window 358 at the distal tip 354 admits light which is focused on an image sensor (not shown) which may be e.g. a CCD or CMOS sensor. The image sensor captures video image data which is transmitted to the display 378. The surgeon may observe video images of the interior of the pneumostoma on display 378 and/or may record images of the pneumostoma for later analysis. In alternative embodiments, one or both of the light source and display may be built into the head 350 and/or handle 340. Pneumoscope 302 may be inserted into a pneumostoma in the same manner as described with respect to pneumoscope 300 and illustrated in FIG. 3B.

Figure 3D:
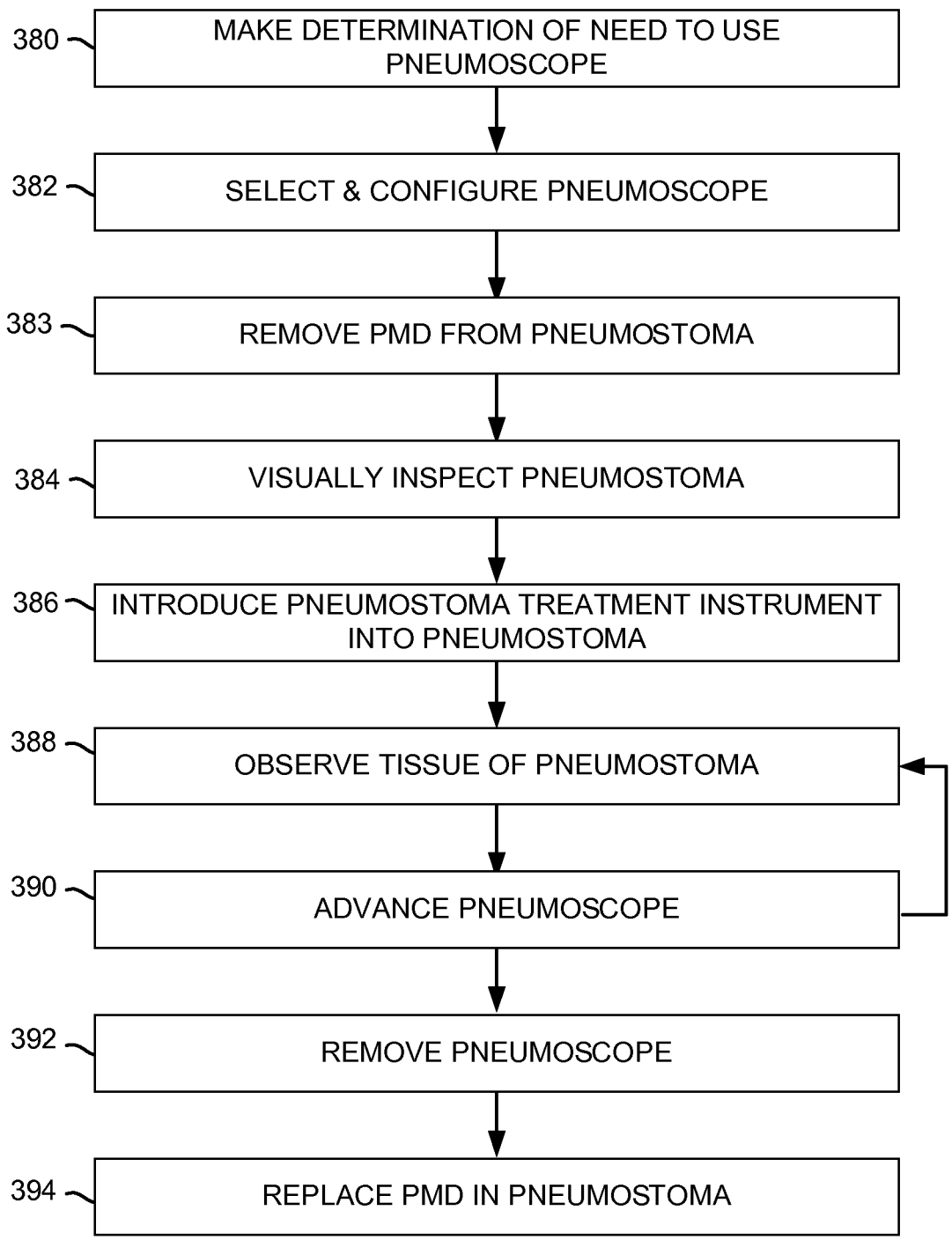
FIG. 3D is a flow chart illustrating steps for examination of a pneumostoma with a pneumoscope according to an embodiment of the invention.

FIG. 3D illustrates a general method for examining a pneumostoma with a pneumoscope. First, based on, for example, information from the patient or observation of the pneumostoma, the physician makes a determination to observe the pneumostoma using a pneumoscope (step 380). The physician next selects and/or configures a pneumoscope suitable to observe the pneumostoma of a particular patient (step 382). The selected instrument is preferably sized such that it can be introduced into the pneumostoma and placed at a desired depth in the pneumostoma. As pneumostomas may vary in size, the pneumoscope may have a configurable size, or may have a range of different sized speculums 330 and/or covers 360. Thus selection of the pneumoscope includes selecting/configuring the pneumoscope for the pneumostoma of a particular patient.

After the pneumoscope is ready, the pneumostoma management device will be removed from the pneumostoma (step 383). The pneumostoma should then be externally inspected (step 384) to determine whether there are any contraindications to use of a pneumoscope, for example any obstruction of the pneumostoma which must first be removed. If the external inspection reveals no contraindications, the pneumoscope is introduced into the pneumostoma (step 386). The physician should observe tissue of the pneumostoma through the visualization system of the pneumoscope (388) and note and/or record the appearance of the tissue. The physician then advances the pneumoscope into the pneumostoma (step 390) and repeats the observation (step 388) until reaching the end of the pneumostoma. When the inspection is completed the pneumoscope is removed (step 392). A PMD should be inserted into the pneumostoma promptly after removal of the pneumoscope either by the physician, or by the patient under the observation of the physician (step 394). In some cases, inspection with the pneumoscope is made in conjunction with treatment of the pneumostoma. In such a case, the pneumoscope may be used before, after and or during the treatment to observe effects of the treatment upon the tissue of the pneumostoma.

The pneumoscope allows the physician to visually inspect and examine the tissues of the pneumostoma. The physician may observe the pneumostoma and examine the tissue in the region of the chest wall, pleurodesis, and/or within the parenchymal tissue of the lung. In the event that inflamed, injured or unusual tissues are observed, it may be desirable to further assess the tissue. Further assessment of the tissue may be made, for example, by swabbing the tissue and culturing any microorganisms on the swab. Alternatively, a biopsy of tissue of the pneumostoma may be made by scraping tissue from the walls of the pneumostoma and examining cells under the microscope. In some embodiments, the pneumoscope may be provided with an auxiliary lumen through which a tool may be introduced into the pneumostoma in order to scrape or swab tissue under visualization.

Pneumostoma Assessment Using Gas

Measurement of gases entering or leaving the pneumostoma may be useful for assessing the functionality of the pneumostoma. The ability of gas to pass through the pneumostoma may be measured in a number of ways. First, gas flow through the pneumostoma can be measured passively by placing a device over the pneumostoma which measures airflow out of and/or into the pneumostoma during regular breathing of the patient. Essentially, gases exiting the pneumostoma are collected by a system which records the volume of gas.

Additionally, the gas may be analyzed to determine composition of the gases exiting the pneumostoma. In particular it may be useful to analyze the proportion of oxygen, carbon dioxide and carbon monoxide in the gases exiting the pneumostoma as compared to in air exhaled through the natural airways or in the ambient atmosphere. Levels of carbon dioxide in gases exiting the pneumostoma are a useful indicator that the pneumostoma is still functioning to allow gases to exit the lung. It may also be useful to measure the presence of nitric oxide in the gases exiting the pneumostoma because nitric oxide may be indicative of inflammation of the tissues of the lung.

Gases exiting the pneumostoma may be measured and/or analyzed with a pneumostoma management device in place. However it is preferable to avoid any confounding effects due to the PMD, for example obstruction of the pneumostoma by the PMD, the filter of the PMD or accumulated discharge in the PMD. Therefore gas measurement/analysis is preferably performed using a gas analysis device inserted into the pneumostoma which is designed to collect gases and interface with the gas measurement/analysis equipment. See, e.g. FIGS. 4D and 4E. Gas analysis and measurement may be performed in a number of modes depending upon the results desired. Different systems may be used for analysis of pneumostoma function, lung function or lung imaging as required.

Systems for supplying gases, to a patient and analyzing gases received from a patient are already in use for supplying gases to be inhaled through the natural airways and analyzing gases exhaled through the natural airways. For example a system for analyzing expiratory gases is described in U.S. Pat. No. 6,506,608 titled "Method And Apparatus For Respiratory Gas Analysis Employing Enhanced Measurement Of Expired Gas Mass" to Mault. A system for supplying and analyzing diagnostic gases is described in U.S. Pat. No. 5,022,406 title "Module For Determining Diffusing Capacity Of The Lungs For Carbon Monoxide And Method" to Tomlinson et al. A review of DLCO spirometry can be found in Macintyre et al., "Standardisation Of The Single-Breath Determination Of Carbon Monoxide Uptake In The Lung," Eur. Respir. J. 26 (4): 720-35 (2005) and reference cited therein. A system for supplying and imaging hyperpolarized noble gases in the lungs is described in U.S. Patent Publication 2005/0174114 title "Method And System For Rapid Magnetic Resonance Imaging Of Gases With Reduced Diffusion-Induced Signal Loss" to Mugler III et al. A review of diffusion imaging of the lung can be found in Mayo et al., "Hyperpolarized Helium 3 Diffusion Imaging Of The Lung," Radiology 222:8-11 (2202) and reference cited therein. The above articles, patents and applications are incorporated herein by reference. These and other such systems may be adapted as described herein to supply and analyze gases utilizing the pneumostoma and thereby provide information regarding lung function, pneumostoma function and collateral ventilation not previously available.

Figure 4A:
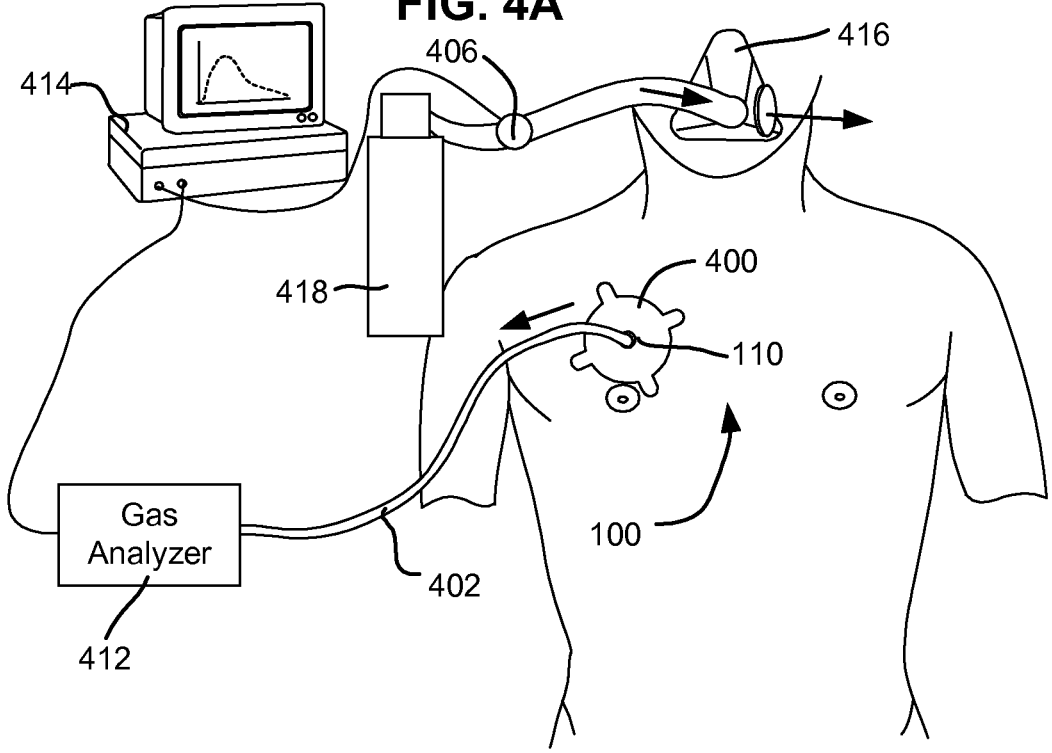
FIG. 4A shows a view of a spirometry system for assessing the functionality of a pneumostoma according to an embodiment of the present invention.

FIG. 4A shows a system for measuring/analyzing gases leaving the pneumostoma. Gas analysis equipment may be connected to a PMD and/or pneumostoma using one of the several techniques and mechanisms described herein. As shown in FIG. 4A, a gas analysis device 400 is inserted into the pneumostoma 110 of a patient. Gas analysis device 400 is connected by tube 402 to gas analyzer 412. The gases exhaled from the pneumostoma 110 may then be measured and/or analyzed during normal breathing or during an exercise test. The volume of gas exhaled may be measured by gas analyzer 412 to provide information regarding the patency/functionality of the pneumostoma. The exhaled gas may be also be analyzed by gas analyzer 412 to determine oxygen and carbon dioxide concentrations. In some cases, the concentrations are compared to oxygen and carbon dioxide concentrations in the gases exhaled through the natural airways or in the ambient atmosphere. Such evaluation may be useful in determining the effectiveness of a pneumostoma and the location and/or desirability of additional pneumostomas. The output of gas analyzer 412 may be provided to a computer system 414 to display the results of the gas analysis. Computer system 414 preferably records the results of the gas measurement and analysis and allows the physician to compare the results of the gas measurement/analysis with prior results for the same patient.

Optionally, a mask 416 may be provided. Mask 416 may be used to measure the volume of gas inhaled and exhaled by the patient through the natural airways. The volume of gas inhaled and exhaled through the natural airways may be compared to the volume of gas exiting the pneumostoma. Optionally, a diagnostic gas 418 is introduced through the natural airways and the expiration of gases from the pneumostoma is measured. Computer system 414 controls valve 406 to supply the diagnostic gas 418 to the mask 416. The diagnostic gas may, for example, be a gas mixture such as DLCO gas used in diffusion spirometry (which nominally consists of 10% helium, 3000 ppm carbon monoxide and the balance air). As shown in FIG. 4A, optional mask 416 may be used to provide a diagnostic gas mixture 418 via the natural airways. The concentration of gases exiting the pneumostoma 110 may be compared to the concentration of gases in the diagnostic gas supply 418. The time-course of exhalation of diagnostic gases through the pneumostoma may be analyzed by gas analyzer 412 to evaluate the function of the pneumostoma and the prevalence of collateral ventilation pathways connecting the pneumostoma to the remainder of the lung. Such evaluation may be useful in determining the effectiveness of a pneumostoma and the location and/or desirability of additional pneumostomas.

Alternatively, gases may be provided through the pneumostoma from outside the chest of the patient. Gas supply equipment may be connected to a PMD and/or pneumostoma using one of the several techniques and mechanisms described herein. The gas is preferably supplied at a controlled pressure slightly above the ambient air pressure so as not to cause injury to the pneumostoma. In a simple case, the rate of flow of gas into the lung through the pneumostoma may be measured. The rate of gas flow at a particular pressure may be used to assess the patency of the pneumostoma. Alternatively, diagnostic gases may be introduced through the pneumostoma for assessing collateral ventilation and gas exchange. Diagnostic gases may be helpful in measuring functional attributes of the pneumostoma and the lung. In particular, introduction of diagnostic gases through the pneumostoma may be useful for assessing gas diffusion between the pneumostoma and the lung.

In one example, a diagnostic gas is introduced through the pneumostoma and the gas is measured as it is exhaled through the natural airways. The diagnostic gas may, for example, be a gas mixture such as DLCO gas used in diffusion spirometry (which nominally consists of 10% helium, 3000 ppm carbon monoxide and the balance air). Gases exhaled through the natural airways are analyzed to determine gas concentrations. The time course of exhalation of the diagnostic gas is indicative of factors such as pneumostoma functionality and collateral ventilation. The time course of exhalation of gas through the natural airways compared to introduction into the pneumostoma may be analyzed to evaluate the function of the pneumostoma and the prevalence of collateral ventilation pathways connecting the pneumostoma to the remainder of the lung. Such evaluation may be useful in determining the effectiveness of a pneumostoma and the location and/or desirability of additional pneumostomas. A supply of the diagnostic gas may be connected to a PMD and/or pneumostoma using one of the several techniques and mechanisms described herein.

Figure 4B:
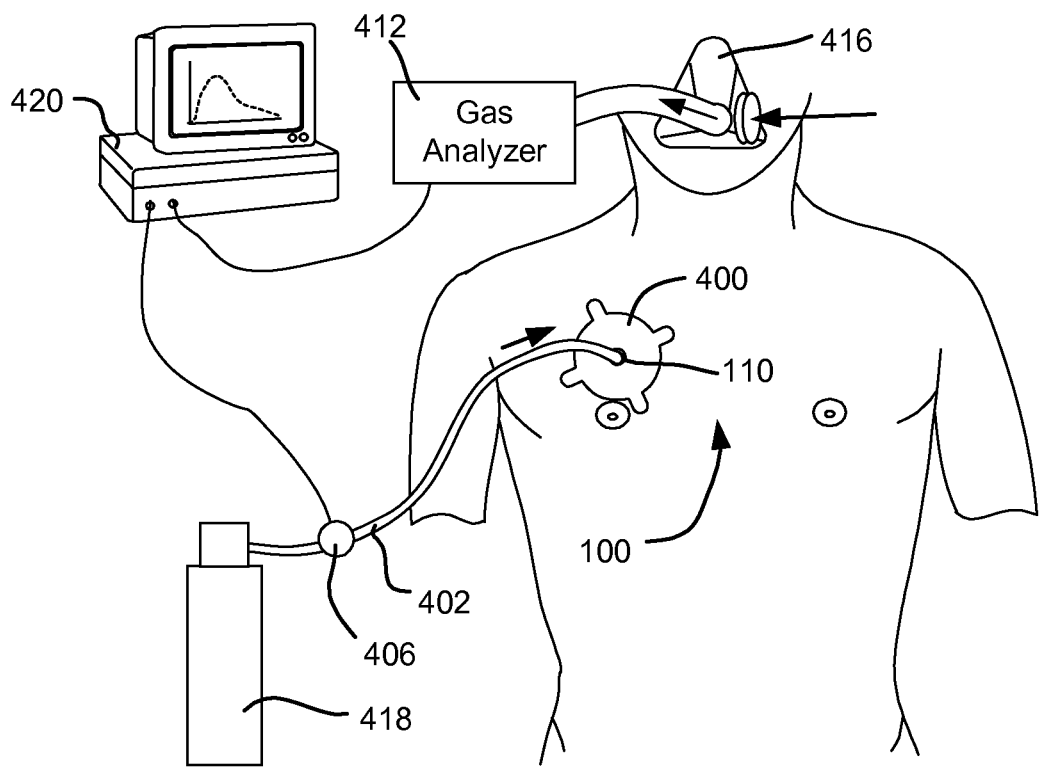
FIG. 4B shows a view of a gas analysis system for assessing the functionality of a pneumostoma according to an embodiment of the present invention.

FIG. 4B shows a schematic view of a lung assessment system using introduction of diagnostic gas 418 through a pneumostoma 110. As shown in FIG. 4B a gas analysis device 400 is inserted into the pneumostoma 110 of a patient. Gas analysis device 400 is connected by tube 402 to a pressure-regulated source of diagnostic gas 418. A solenoid-controlled valve 406 in tube 402 controls the flow of diagnostic gas into pneumostoma 110. The patient is provided with a mask 416 which allows the patient to inhale ambient air but that collects the exhaled air and passes it to gas analyzer 412. During exhalation, a portion of the exhaled gases is collected in a sample collection system and then analyzed using discrete gas sensors and/or a gas chromatograph. The gas analyzer 412 and the solenoid-controlled valve 406 are connected to a computer system 420 which may be a general purpose computer. Computer system 420 controls solenoid-controlled valve 406 and receives data from gas analyzer 412. Computer system 420 analyzes the gas concentrations in the gas exhaled by the patient and factors the relative values with inspired gas volume and other parameters to calculate factors related to collateral ventilation and pneumostoma function. The output of gas analyzer 412 may be provided to computer system 420 to display the results of the gas analysis. Computer system 420 preferably records the results of the gas measurement and analysis and allows the physician to compare the results of the gas measurement/analysis with prior results for the same patient.

Introduction of diagnostic gases through a pneumostoma may also be used to enhance imaging the lung with a CT scan or NMR scan. For example polarized Helium-3 may be utilized to enhance nuclear magnetic resonance/magnetic resonance imaging of the lung (analogous to the way contrast agents enhance X-ray imaging). For example, polarized helium-3 may be produced with lasers and the magnetized pressurized gas may be stored for several days. When introduced into the lung, the polarized helium-3 can be imaged with an MRI-like scanner which produces breath-by-breath images of lung ventilation, in real-time. Polarized helium-3 may thus, be used to visualize airways in static or dynamic fashion. Alternative gases which may be used as visualization agents include gaseous radionuclide xenon or technetium DTPA in an aerosol form.

Introducing a controlled amount of a visualizable gas, e.g. polarized Helium-3, through the pneumostoma and imaging the diffusion of the gas into the lung over time may be utilized for quantitative evaluation of the function of the pneumostoma and the prevalence of collateral ventilation pathways connecting the pneumostoma to the parenchymal tissue of the lung. Measuring the time-course variations in diffusion of Helium-3 into the lung allows analysis of diffusion coefficients for areas of the lung. Such evaluation may be useful in determining the effectiveness of a pneumostoma and the location and/or desirability of additional pneumostomas. A source of polarized Helium-3 may be connected to a PMD and/or pneumostoma using one of the several techniques and mechanisms described herein.

Figure 4C:
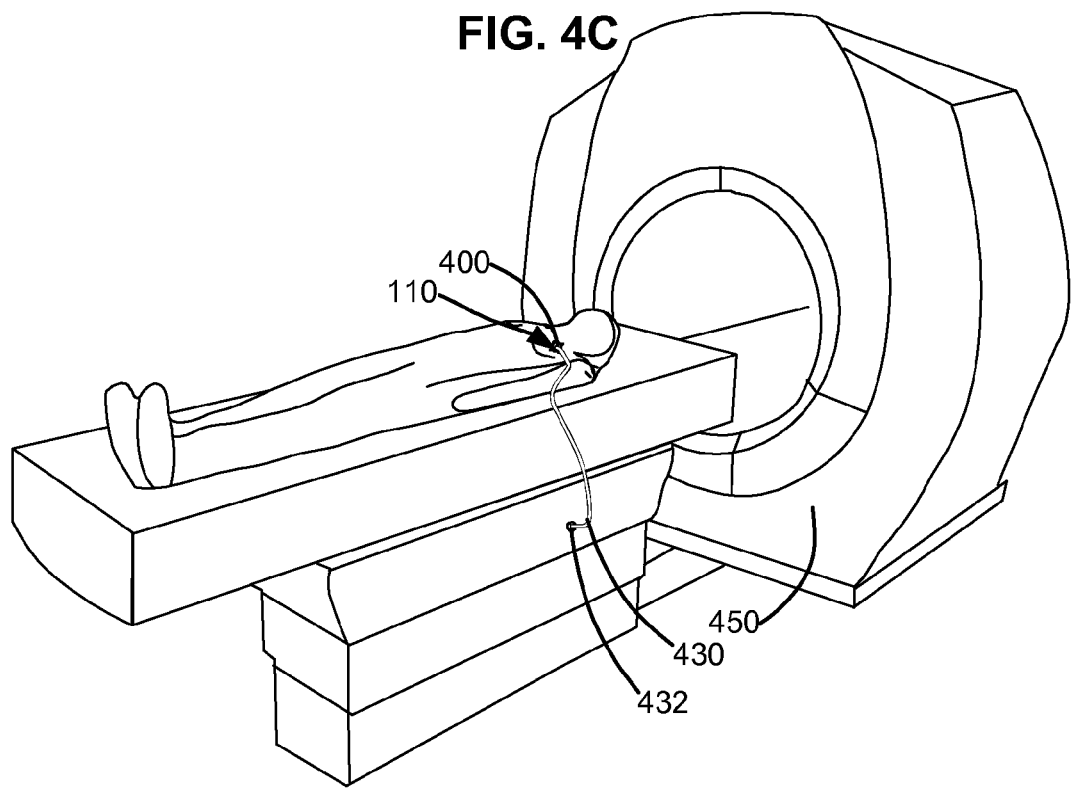
FIG. 4C shows a view of lung imaging system for imaging gas diffusion from a pneumostoma according to an embodiment of the present invention.

FIG. 4C shows a schematic view of a lung assessment system using a diagnostic gas in conjunction with an imaging scanner 450. Scanner 450 may be an MRI, NMR, CT or X-Ray so long as the particular diagnostic gas used may be successfully imaged with the system. As shown in FIG. 4B, gas analysis device 400 is inserted into the pneumostoma 110 of a patient. Gas analysis device 400 is connected by tube 430 to a pressure-regulated source of a visualizable gas (e.g. polarized Helium-3). A solenoid-controlled valve 432 in tube 430 controls the flow of diagnostic gas into pneumostoma 110. The scanner 450 and the solenoid-controlled valve 432 are connected to a computer system 420 (not shown) which may be a general purpose computer. The computer system 420 (not shown) controls solenoid-controlled valve 432 and receives data from scanner 450. The computer system 420 coordinates the introduction of diagnostic gas into the patient with the patient's breathing and also with the operations of scanner 450 in order to accurately image dispersion of the diagnostic gas from the pneumostoma 110 to other parts of the lung. Computer system 420 analyzes the time course distribution of the diagnostic gas from the pneumostoma into the lung tissues to calculate factors related to collateral ventilation and pneumostoma function, e.g. diffusion coefficients.

Figure 4D:
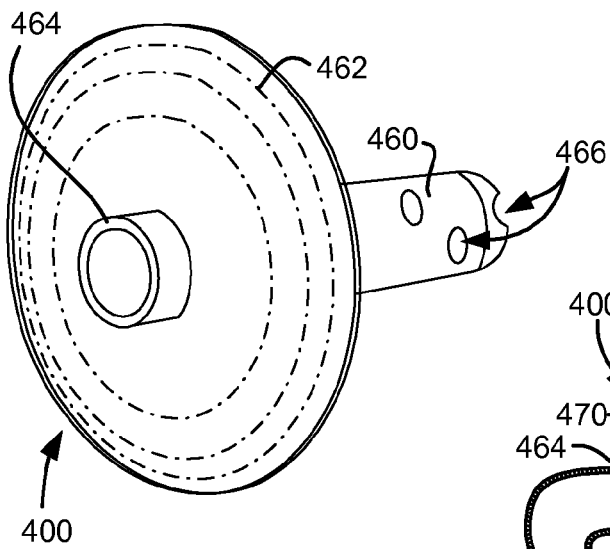
FIGS. 4D and 4E show views of a diagnostic device for delivering diagnostic gas to a pneumostoma or sampling gas from a pneumostoma according to embodiments of the present invention.
Figure 4E:
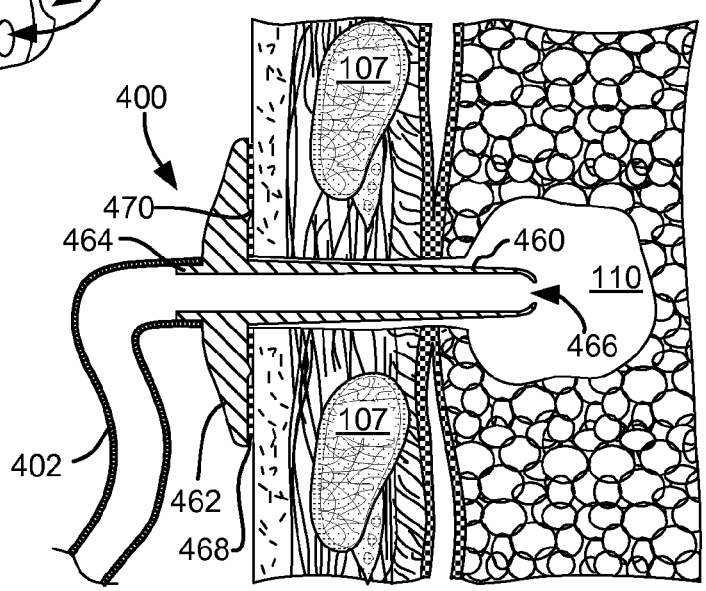

FIGS. 4D and 4E show views of the gas analysis device 400 of FIGS. 4A-4C. FIG. 4D shows a perspective view of the gas analysis device 400 while FIG. 4E shows a sectional view of gas analysis device 400 positioned within a pneumostoma. In general terms, gas analysis device 400 is a device which can be secured into a pneumostoma for sampling gases exiting the pneumostoma and/or providing gases into the pneumostoma. Gas analysis device 400 can form part of a system which utilizes such gas sampling or gas provision for assessment of pneumostoma function and/or lung function. As used in FIGS. 4A and 4C, gas analysis device 400 is used to introduce diagnostic gas into the pneumostoma. As used in FIG. 4B, gas analysis device 400 is used to collect gases exhaled from the lung for analysis by gas analyzer 412.

Referring to FIG. 4D, gas analysis device 400 includes a hollow tube 460 for insertion into the pneumostoma. Hollow tube 460 is surrounded by a flange 462 which secures tube 460 in position in the pneumostoma. Hollow tube 460 connects to a coupling 464 on the proximal side of flange 462. Coupling 464 is configured so that tube 402 (shown in FIG. 4E) may be readily connected and disconnected. Hollow tube 460 has one or more holes 466 at the distal end through which gas may pass into or out of a pneumostoma. Hollow tube 460 and flange 462 also provide a temporary seal which inhibits leakage of gas from around hollow tube 460.

FIG. 4E shows a sectional view of gas analysis device 400 of FIGS. 4A-4D in position in a pneumostoma 110. It is preferable to minimize leakage of gases into or out of the pneumostoma. Flange 462 is thus provided with an adhesive coating 468 on the distal surface to provide a temporary seal between the gas analysis device 400 and the skin of the chest of the patient. Surface features may also be provided on the distal surface of flange 462 or on tube 460 to promote sealing between gas analysis device 400 and the pneumostoma. For example, a circular ridge 470 is shown in section on FIG. 4E. Gas analysis device 400 is preferably a disposable component that will be used only with one patient. One or more filters may be interposed between gas analysis device 400 and the gas supply and/or gas analyzer to prevent possible cross-contamination between patients.

Pneumostoma Treatment

Based upon the assessment of the pneumostoma, it may be necessary or desirable to treat the pneumostoma in order to preserve and/or enhance the health and/or functionality of the pneumostoma. A principal purpose of the pneumostoma is to permit the escape of gases trapped in the lung thereby reducing the lung volume and ameliorating symptoms of COPD such as dyspnea and anoxia. To serve this purpose gases should be able to enter the pneumostoma from the parenchymal tissue of the lung. High rates of air flow are not required. However, if the pneumostoma becomes completely obstructed then it will no longer permit the escape of gases trapped in the lung. The function of the pneumostoma may be impaired by, among other causes, the encroachment of tissues into the pneumostoma, obstruction with secretions, discharge and/or foreign objects, inflammation and/or infection. For example, encroaching tissues may impair the patency and functionality of the pneumostoma.

The pneumostoma and surrounding tissues may be treated using a number of different treatment modalities to maintain and/or enhance patency, remove obstructions, decrease inflammation and prevent infection. The treatment modalities include: suction, irrigation, lavage, mechanical agitation, ultrasound, infrasound, mechanical dilation, balloon dilatation, cryotherapy, and energy treatment (including e.g. UV, light, LASER, LED, IR, heat, RF and electrocautery). The physician may select from among the several treatment modalities a treatment modality most appropriate for the conditions observed during the pneumostoma assessment.

Pneumostoma Treatment Using Suction, Irrigation and Lavage

The treatment modalities available for treating a pneumostoma include dilation, suction, irrigation, mechanical agitation and lavage. These treatment modalities are suitable for removing obstructions and discharge from the pneumostoma, cleaning the pneumostoma and treating the tissues of the pneumostoma. Additional methods and devices for applying suction to a pneumostoma are disclosed in applicant's U.S. Provisional Patent Application 61/084,559 titled "Aspirator For Pneumostoma Management" which is incorporated herein by reference. An aspirator may be used without irrigation for the removal of liquid/soft discharge and materials from the pneumostoma.

Figure 5A:
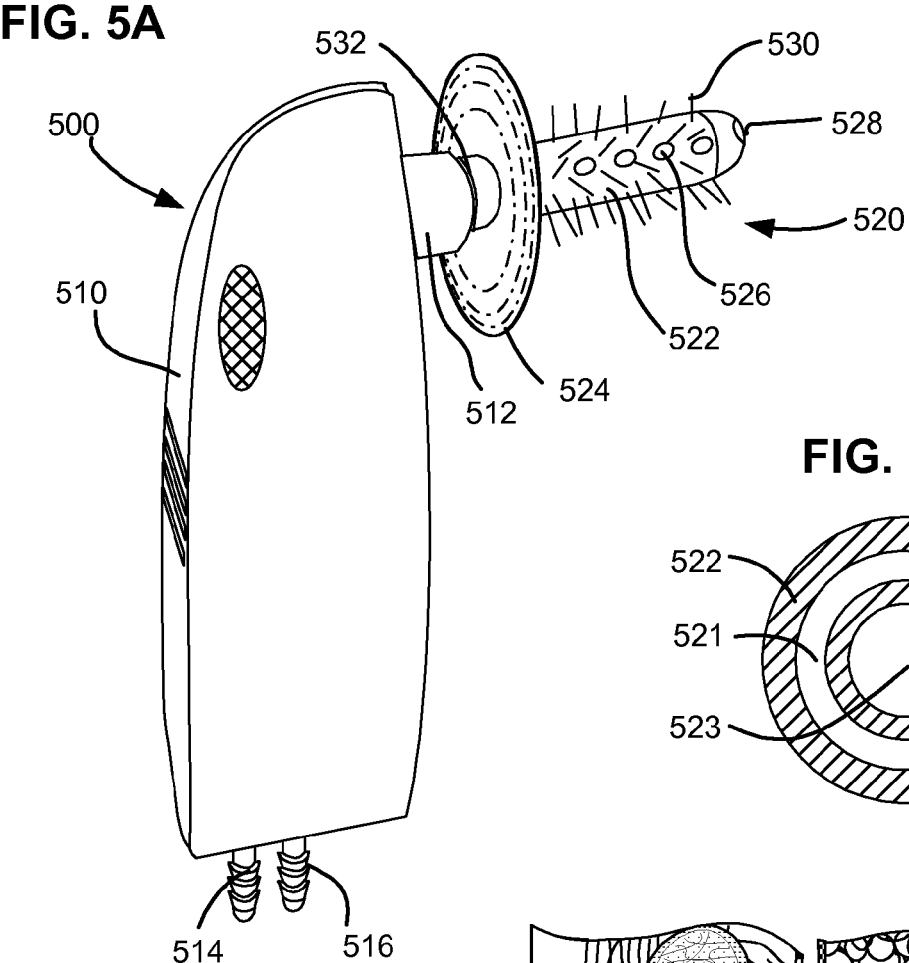
FIGS. 5A-5C show views of a device for cleaning and treating the pneumostoma according to an embodiment of the invention.
Figure 5B:
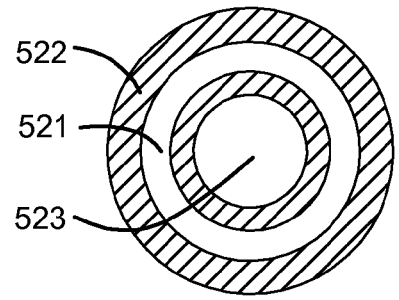
Figure 5C:
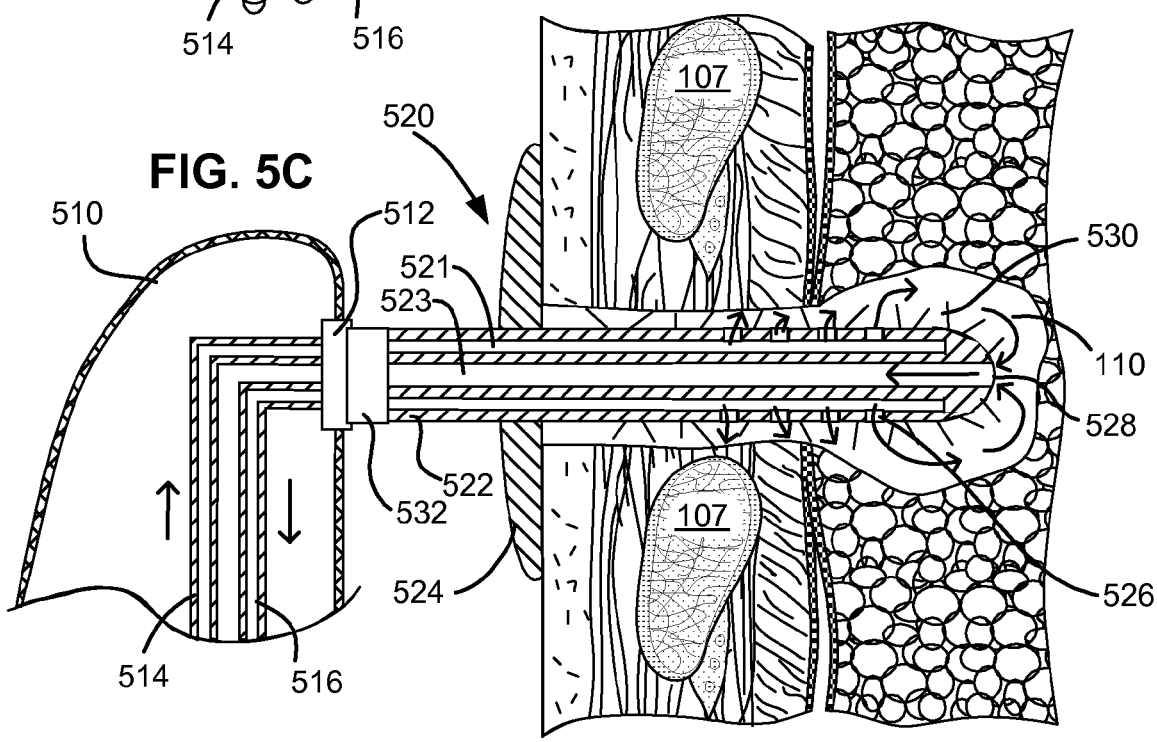

FIGS. 5A-5C illustrate a device for treating a pneumostoma with suction, irrigation, mechanical irritation and/or lavage. As shown in FIG. 5A, a suction-irrigation device 500 includes a body 510 attached to a suction-irrigation probe 520. Suction-irrigation probe 520 includes a multi-lumen tube 522 and a flange 524. As shown in the sectional view FIG. 5B of suction-irrigation probe 520, multi-lumen tube 522 has an outer lumen 521 and an inner lumen 523. Referring again to FIG. 5A, multi-lumen tube 522 has a number of side apertures 526 for releasing fluid from the outer lumen 521. Multi-lumen tube 522 has a distal aperture 528 in the distal tip for applying suction and removing fluid via the inner lumen 523. Distal aperture 528 may be provided with a cage or mesh covering to prevent damage to tissues and/or obstruction of distal aperture 528. Multi-lumen tube 522 also supports a plurality of soft bristles 530 for mechanically agitating the surface of a pneumostoma. Although bristles are shown, other mechanical features may be used to assist the removal of material which may be adhered to the tissue of the pneumostoma, for example ribs, fingers or surface roughness.

Referring now to FIG. 5C, suction irrigation probe 520 is connected to a body 510 by a coupling 532 which mounts releasably to a mating coupling 512 on body 510. Body 510 is also connected to a pressure-regulated supply of irrigation fluid and a pressure-regulated vacuum supply (not shown). The irrigation supply and vacuum supply are attached or connected to an irrigation conduit 514 and suction conduit 516 within body 510. The couplings 532 and 512 releasably mount the suction-irrigation probe 520 to body 510. The couplings 532 and 512 also put the lumens of multi-lumen tube 522 in fluid communication with the irrigation conduit 514 and suction conduit 516 within body 510. The releasable couplings 532 and 512 also enable the suction-irrigation probe 520 to be removed, and either cleaned and replaced, or disposed of and replaced. Couplings 532, 512 may be, for example, threaded couplings, bayonet couplings, luer locks or other connector suitable for releasable connecting lumens.

FIG. 5C shows a sectional view of suction-irrigation device 500 with suction-irrigation probe 520 inserted into a pneumostoma 110. As shown in FIG. 5C, irrigation fluid exits through side apertures 526 and is collected through distal aperture 528. Bristles 530 contact the tissue of the pneumostoma 110. Suction-irrigation probe 520 may be moved in and out of pneumostoma 110 so that bristles 530 dislodge any material stuck on the side of pneumostoma 110. The irrigation fluid serves to move any dislodged materials into aperture 528. Flange 524 serves to prevent over-insertion of suction-irrigation probe 520 and also to prevent excessive leakage of irrigation fluid from the pneumostoma. In some embodiments, flange 524 may be configured to slide up and down multi-lumen tube 522 such that the depth of the distal end of probe 520 may be adjusted while the flange remains in contact with the chest of the patient. In other embodiments, flange 524 may be fixed or adjustably fixed to multi-lumen tube 522.

Suction-irrigation device 500 may include additional features to facilitate removal of material from the pneumostoma. For example, suction-irrigation device 500 may include a visualization system to permit the physician to guide suction-irrigation probe 520 and visualize the tissues inside pneumostoma 110. See, e.g. FIGS. 3A-3C and accompanying text. Suction-irrigation device 500 may also include an ultrasound generator or another device to agitate bristles 530 and the irrigation fluid to aid in the mechanical removal of materials from the pneumostoma 110. Suction irrigation device 500 may also include a trap for trapping any solid materials dislodged from the pneumostoma. For irrigation, a sterile but inert solution may be used. For example, sterile saline or sterile water may be used. The irrigation fluid will typically be sterile water or saline solution. In some cases, it may be desirable to use a medicated irrigation fluid. For example, an antibacterial or mucolytic solution may be used. In such cases a small concentration of the therapeutic agent is added to the sterile water or saline. Suitable therapeutic agents include anti-inflammatories, antibiotics and anti-stenosis compounds. The irrigation fluid may also include a small concentration of an agent for maintaining the patency of the pneumostoma, for example, Paclitaxel. The cleaning solution should be formulated carefully to avoid injury or irritation to the lung.

FIG. 5D illustrates a method for treatment of a pneumostoma. First, based on, for example, information from the patient or observation of the pneumostoma, the physician makes a determination to treat the pneumostoma with one or more of suction, irrigation and/or lavage. (step 580). The physician next selects and/or configures an aspirator/irrigator suitable to treat the pneumostoma of a particular patient. (step 582). The selected instrument is preferably sized such that it can be introduced into the pneumostoma and placed at a desired depth in the pneumostoma. As pneumostomas may vary in size, the aspirator/irrigator may have a configurable size, or may have a range of different sized probes 520. Thus selection of the aspirator/irrigator includes selecting/configuring the aspirator/irrigator for the pneumostoma of a particular patient. If irrigation/lavage is to be performed, the physician should also select and/or prepare the irrigation fluid (step 584).

After the aspirator/irrigator and optional irrigation fluid is ready, the pneumostoma management device will be removed from the pneumostoma (step 586). The pneumostoma should then be externally inspected (step 588) to determine whether there are any contraindications to use of the aspirator/irrigator, for example any obstruction of the pneumostoma which must first be removed. If the visual inspection reveals no contraindications, the aspirator/irrigator is introduced into the pneumostoma (step 590). The physician may then position the flange so as to prevent excess leakage from the pneumostoma (step 592). The physician will the apply suction to remove materials from the pneumostoma (step 594). While suction is applied the physician may also provide irrigation/lavage and or agitation to dislodge materials for removal (step 594.) The physician may advance the aspirator/irrigator incrementally further into the pneumostoma and repeats the treatment (step 594) until reaching the end of the pneumostoma. When the treatment is completed the aspirator/irrigator is removed (step 596). A PMD should be inserted into the pneumostoma promptly after removal of the aspirator/irrigator either by the physician, or by the patient under the observation of the physician (step 598). In some cases, treatment with the aspirator/irrigator is made in conjunction with inspection of the pneumostoma with a pneumoscope. In such case, the pneumoscope may be used before and after treatment to observe effects of the treatment upon the tissue of the pneumostoma and to ensure all deleterious materials have been removed from the pneumostoma.

Pneumostoma Treatment Using Sound

The treatment modalities available for treating a pneumostoma include the use of sound waves. Sound waves can be used to agitate the walls of the pneumostoma to dislodge materials. Sound waves of different frequencies may be of use, including infrasound below 20 Hz, acoustic sound waves between 20 Hz and 20 KHz and ultrasound above 20 KHz. These treatment modalities are suitable for removing obstructions and discharge from the pneumostoma, cleaning the pneumostoma and treating the tissues of the pneumostoma to enhance and/or maintain patency of the pneumostoma. The amplitude, frequency and duration of sound waves supplied may be selected to achieve the desired effects. In some cases the amplitude, frequency and duration of the sound waves may be sufficient to kill cells, inhibit proliferation of cells or disrupt cells and connective tissue in order to enhance or maintain the patency of the pneumostoma. In other cases, the sound waves may be selected to dislodge materials e.g. discharge, which may be adhered to the tissues of the pneumostoma. In some embodiments, ultrasound may be used in conjunction with suction/irrigation to remove materials from the pneumostoma.

Figure 6A:
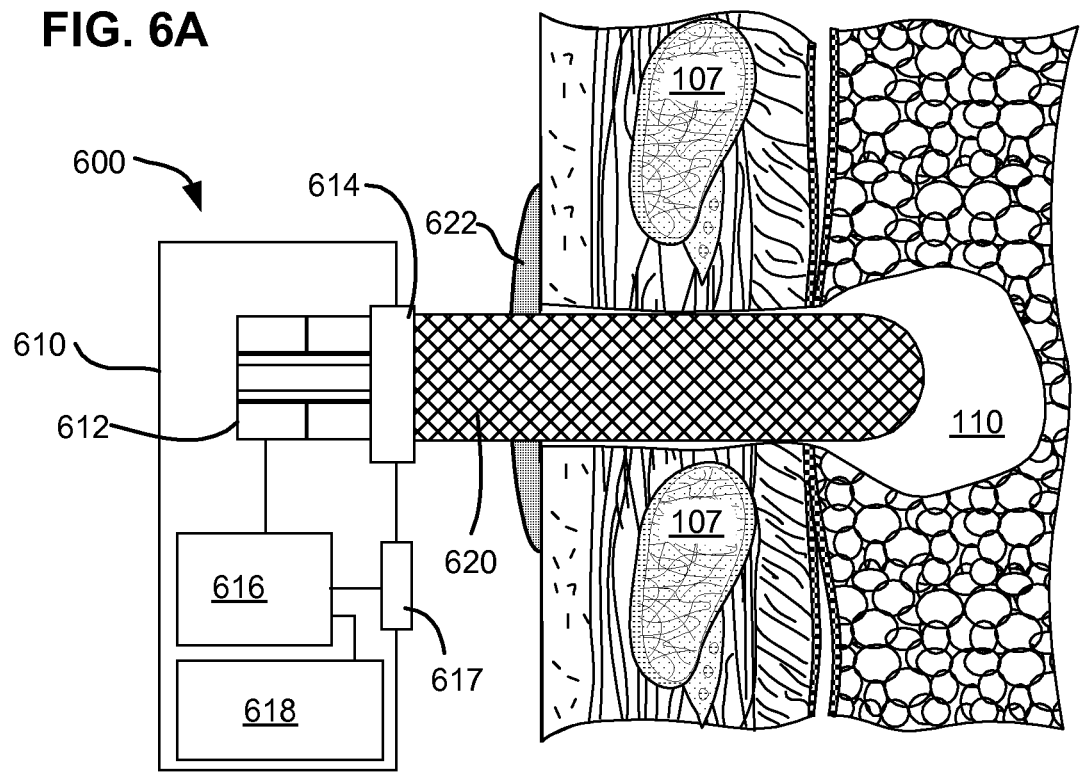
FIG. 6A shows a view of an ultrasound device for cleaning or treating the pneumostoma according to an embodiment of the invention.

FIG. 6A shows a sectional view of an ultrasound device 600 for use in a pneumostoma 110. Ultrasound device 600 includes a body 610 containing an ultrasonic transducer 612 coupled by a coupling 614 to an ultrasound probe 620. Ultrasonic transducer 612 is coupled to ultrasound probe 620 so that, when energized, ultrasonic transducer 612 transmits ultrasound into ultrasound probe 620. Ultrasound device 600 includes within body 610, a switch 617, a controller 616 and power supply 618. The physician operates switch 617 to cause controller 616 to energize ultrasonic transducer 612. In preferred embodiments, controller 616 energizes ultrasonic transducer 612 for a predefined and limited period of time.

Ultrasound probe 620 is sized and configured to enter pneumostoma 110 and conduct ultrasound energy from ultrasonic transducer 612 to the walls of the pneumostoma and any materials adhered thereto. Ultrasound probe 620 may also include a flange 622 which serves as protection against over insertion of probe 620. A biocompatible gel or liquid (not shown) may be used with ultrasound probe 620 to enhance the conduction of ultrasonic waves from ultrasound probe 620 to tissues of the pneumostoma. In such case, flange 622 may also be useful to create a temporary seal to retain the gel or liquid with pneumostoma 110 during the ultrasound treatment. In some embodiments, ultrasound probe 620 may be provided with a channel to provide suction to remove any materials dislodged by the ultrasound. Alternatively, a separate suction/irrigation device may be utilized to remove materials from the pneumostoma after treatment with the ultrasound probe 620.

Figure 6B:
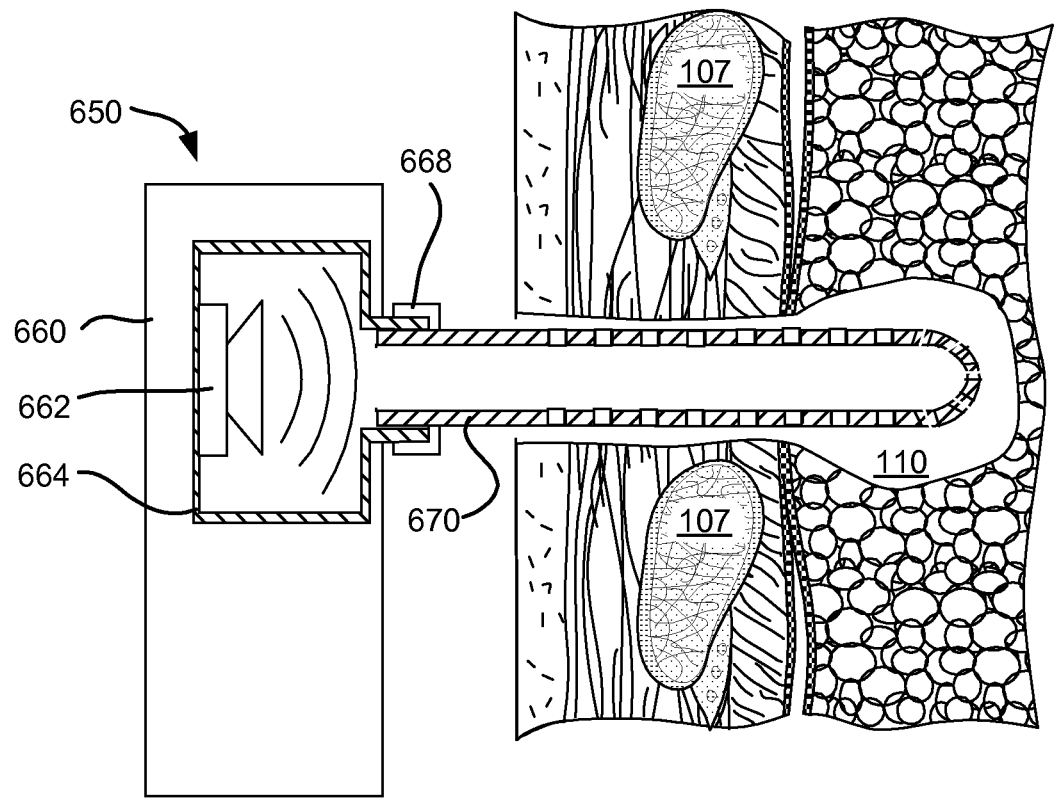
FIG. 6B shows a view of a sound-wave therapy device for cleaning or treating the pneumostoma according to an embodiment of the invention.

FIG. 6B shows a schematic view of alternate sound delivery device 650 for use in a pneumostoma 110. Sound delivery device 650 includes a body 660 containing a speaker 662 which typically comprises a magnetically-driven armature or diaphragm. Speaker 662 generates acoustic and/or infrasound waves in chamber 664. Chamber 664 is in communication via coupling 668 with sound probe 670. As shown in FIG. 6B, sound probe 670 is a hollow tube for holding open the pneumostoma and delivering the sound waves into the pneumostoma. Sound probe 670 may have one or more apertures. A baffle may be provided around sound probe 670 to concentrate pressure waves induced by the speaker with the pneumostoma. Alternatively, sound probe 670 may be a solid probe coupled to the armature of speaker 662 or a suitable transducer. In alternative embodiments, the sound may be generated by a speaker located within the probe which is thus located within the pneumostoma during use. The energy delivered by sound delivery device 650 serves to dislodge materials from the pneumostoma and/or disrupt the connective tissue of the pneumostoma. In some embodiments, sound probe 670 may be provided with a channel to provide suction to remove any materials dislodged by the sound waves. Alternatively, a separate suction/irrigation device may be utilized to remove materials from the pneumostoma after treatment with the sound delivery device 650.

Figure 6C:
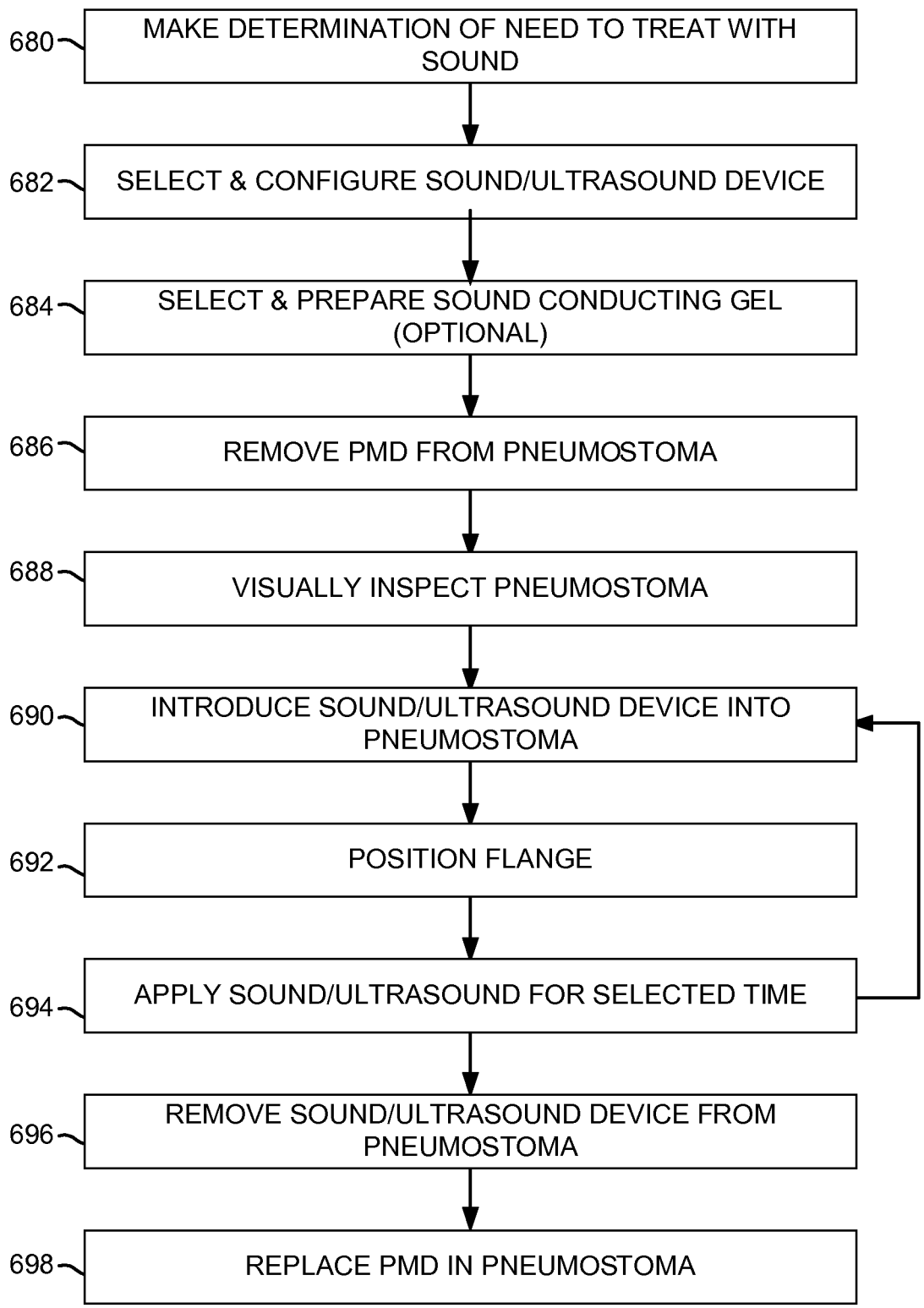
FIG. 6C is a flow chart illustrating steps for treatment of a pneumostoma with sound and/or ultrasound according to an embodiment of the invention.

FIG. 6C illustrates a method for treatment of a pneumostoma. First, based on, for example, information from the patient or observation of the pneumostoma, the physician makes a determination to treat the pneumostoma with one or more of acoustic sound, infrasound, and/or ultrasound. (step 680). The physician next selects and/or configures a sound/ultrasound device suitable to treat the pneumostoma of a particular patient. (step 682). The selected instrument is preferably sized such that it can be introduced into the pneumostoma and placed at a desired depth in the pneumostoma. As pneumostomas may vary in size, the sound/ultrasound device may have a configurable size, or may have a range of different sized probes 620 or 670. Thus selection of the sound/ultrasound device includes selecting/configuring the sound/ultrasound device for the pneumostoma of a particular patient. If a sound conducting liquid or gel is to be used, the physician should also select and/or prepare the fluid (step 684).

After the sound/ultrasound device and optional sound-conducting fluid is ready, the pneumostoma management device will be removed from the pneumostoma (step 686). The pneumostoma should then be externally inspected (step 688) to determine whether there are any contraindications to use of the sound/ultrasound device, for example any obstruction of the pneumostoma which must first be removed. If the visual inspection reveals no contraindications, the sound/ultrasound device is introduced into the pneumostoma (step 690). The physician may then position the flange so as to prevent excess leakage from the pneumostoma (step 692). The physician will then energize the sound/ultrasound probe for a selected period of time (step 694). The physician may advance the sound/ultrasound device incrementally further into the pneumostoma and repeat the treatment (step 694) until reaching the end of the pneumostoma. When the treatment is completed the sound/ultrasound device is removed (step 696). A PMD should be inserted into the pneumostoma promptly after removal of the aspirator/irrigator either by the physician, or by the patient under the observation of the physician (step 698).

In some cases, treatment with the sound/ultrasound device is made in conjunction with inspection of the pneumostoma with a pneumoscope. In such case, the pneumoscope may be used before and after treatment to observe effects of the treatment upon the tissue of the pneumostoma and to ensure all deleterious materials have been removed from the pneumostoma. It may also be desirable to clean the pneumostoma with suction/irrigation prior to reinsertion of the PMD in order to remove any materials that may have been dislodged during the treatment.

Pneumostoma Treatment Using Mechanical Dilatation

The treatment modalities available for treating a pneumostoma include the use of mechanical dilatation. Overtime, the natural healing response of the body may cause tissues to encroach into the lumen of the pneumostoma. Additionally, the tissues bordering the pneumostoma may thicken over time reducing the permeability of the pneumostoma walls to gases. A dilator may be used to stretch the tissues of the pneumostoma to maintain the patency of the pneumostoma. Dilatation not only increases the size of the lumen of the pneumostoma but also thins the tissues surrounding the pneumostoma. This thinning of the tissues bordering the pneumostoma in the lung may enhance the ability of air to enter the pneumostoma from the parenchymal tissue of the lung thereby enhancing the functionality of the pneumostoma. In embodiments, a dilator comprises an expander which can be inserted into the pneumostoma at a first contracted size and then expanded to a desired expanded size thereby stretching the pneumostoma. In preferred embodiments the dilator comprises an indicator outside the body which indicates the extent to which the expander has been expanded and/or an adjustable limiter which limits expansion of the expander to a safe amount.

Figure 7A:
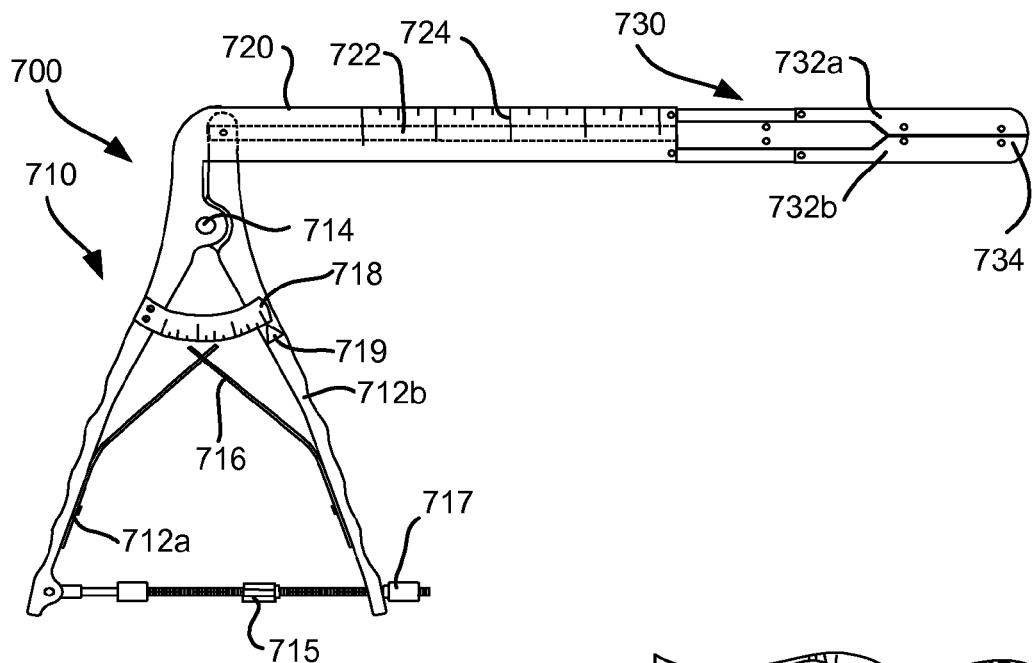

FIGS. 7A-7D show views of one embodiment of mechanical dilator 700. As shown in FIG. 7A, mechanical dilator 700 comprises a handle 710, a shaft 720 and an expander 730. Handle 710 includes two arms 712*a*, 712*b* connected by a pivot 714. A spring mechanism 716 biases arms 712*a*, 712*b* apart. A screw mechanism 717 may be used to lock arms 712*a*, 712*b* closer together at any desired position. A limit mechanism 715 may be used to limit the approach of arm 712*a* towards arm 712*b* in order to prevent over expansion of the expander 730. Handle 710 is connected to shaft 720. Arm 712*a*, is fixedly connected to the exterior of shaft 720, arm 712*b* is pivotally connected to inner shaft 722. Moving arm 712*b* towards arm 712*a* moves inner shaft 722 more distally relative to shaft 720. Handle 710 also includes a gauge 718 marked to indicate the amount of expansion of expander 730. Gauge 718 is fixed to arm 712*a*. An indicator 719 fixed to arm 712*b* moves along gauge 718 as the arms are moved towards each other thereby expanding expander 730. The markings on gauge 718 correspond to the expansion of expander 730.

Shaft 720 is sized so as to fit into the pneumostoma. Shaft 720 may be provided with markings 724 on the exterior surface so the physician may determine the depth to which the distal tip of expander 730 has been inserted in the pneumostoma. Expander 730 includes two blades 732*a*, 732*b*. Blades 732*a*, 732*b* are semicircular in section so that, in the collapsed configuration, blades 732*a*, 732*b* form a cylinder of the same external diameter as shaft 720. Blades 732*a*, 732*b* also form a rounded distal tip 734 in their collapsed configuration to facilitate insertion of expander 730 into the pneumostoma.

Figure 7B:
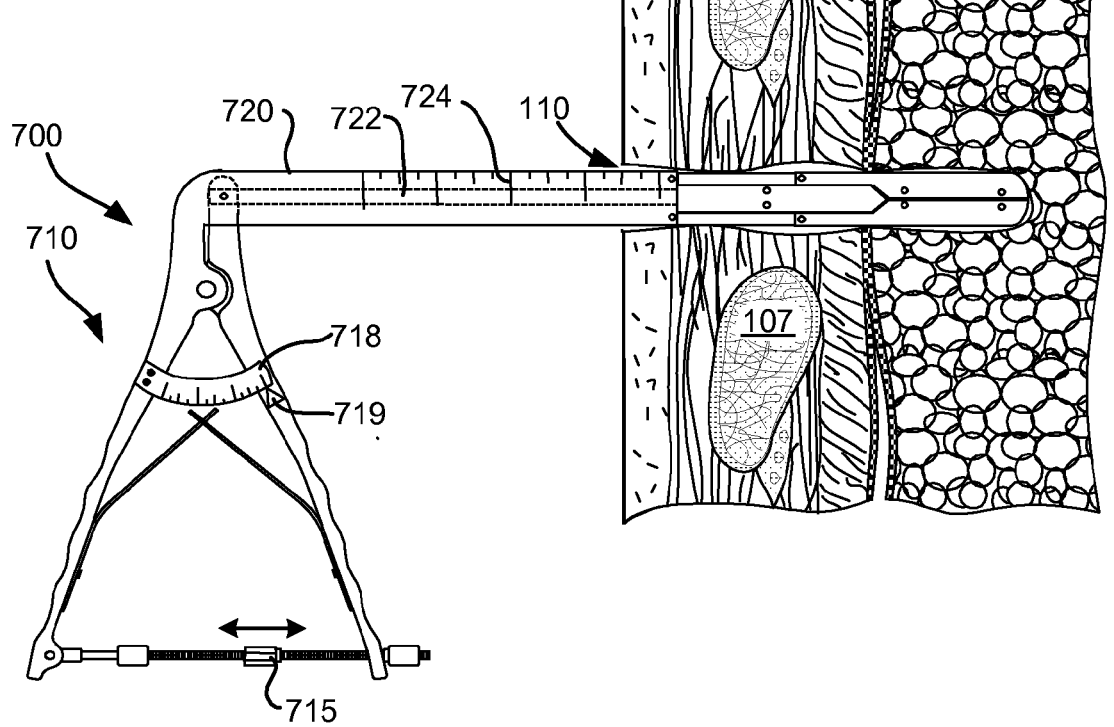

FIG. 7B shows mechanical dilator inserted into a pneumostoma 110 (shown in section). As shown in FIG. 7B, the mechanical dilator 700 is inserted into the pneumostoma 110 in the collapsed configuration of FIG. 7A until it is located at the desired depth in the pneumostoma as indicated by the markings 724. In some situations, mechanical dilator 700 may be used to measure the diameter of a pneumostoma. The expander may be inserted into the pneumostoma and the handles compressed until resistance is felt. The indicator 719 will indicate on gauge 718 the degree of expansion of expander 730 at this point of first resistance and thus indicate the internal diameter of the pneumostoma. Limit mechanism 715 may then be positioned to allow only a desired amount of incremental expansion of the pneumostoma compared to the measured initial diameter of the pneumostoma. In alternative embodiments, a fixed or adjustable flange (not shown) may be provided mounted on shaft 720. The flange serves as mechanical stop to limit insertion of the mechanical dilator 700 at a fixed or adjustable depth.

FIG. 7C shows a close-up view of the expander 730 in an expanded configuration. As shown in FIG. 7C, each of blades 732*a* and 732*b* are pivotally connected by linkages 736*a*, 736*b* to the distal end of shaft 720. Each of blades 732*a*, 732*b* is also pivotally connected to the distal end of inner shaft 722 by linkages 738*a*, 738*b*, 738*c*, 738*d*. Linkages 738*a*, 738*b*, 738*c*, 738*d* are designed to fit within a slot in the interior surface of blades 732*a*, 732*b* when the blades are in the collapsed configuration of FIG. 7A. In alternative embodiments, expander 730 may have 3 or more blades, each blade taking up a fractional portion of the circumference of the device and each blade having three linkages connecting the blade to the distal end of inner shaft 722. As inner shaft 722 moves in the direction of arrow 704, blades 732*a*, 732*b* move outwards as shown by arrows 702*a*, 702*b*.

FIG. 7D shows mechanical dilator 700 positioned in a pneumostoma 110. As shown in FIG. 7D, expander 730 is positioned within the pneumostoma at the desired depth. Handle 712*b* has been pushed towards handle 712*a* until it makes contact with limit mechanism 715. Handle 712*b* may optionally be locked into position with screw mechanism 717. Inner shaft 722 has been pushed distally relative to shaft 720. Linkages 738*a*, 738, *b*, 738*c*, 738*d* have thus forced blades 732*a*, 732*b* away from each other causing the expander 730 to adopt the expanded position shown in FIG. 7C (see FIGS. 7B and 7C for identification of the components of expander 730). Note that indicator 719 has moved along gauge 718 to indicate the amount of expansion of expander 730.

In practice, mechanical dilator 700 is preferably expanded a small amount and then locked in place as the tissues of the pneumostoma relax. Mechanical dilator 700 is then expanded another small amount and then locked in place again as the tissues of the pneumostoma relax. A number of incremental expansion steps may be performed until the desired diameter of the pneumostoma is achieved. The incremental steps can be controlled by incremental movement of limit mechanism 715 and screw mechanism 717. In some cases, it may be desirable to expand the dilator at two or more different depths in the pneumostoma so as to expand two or more different potions of the pneumostoma. Dilator 700 may then be collapsed and withdrawn from the pneumostoma. The pneumostoma will tend to contract after dilatation so it is important to insert a pneumostoma management device into the lumen of the pneumostoma upon removal of the mechanical dilator 700.

In some situations where a pneumostoma is no longer permitting the escape of gases (pneumostoma is closed) a surgical tool, e.g. mechanical dilator 700 and/or forceps, can be used by a physician to reopen the pneumostoma by blunt dissection of the pneumostoma within the lung. Blunt dissection creates new and/or additional pathways for gases to enter the pneumostoma from the parenchymal tissue of the lung avoiding a new pneumostomy procedure to create a new pneumostoma.

Figure 7E:
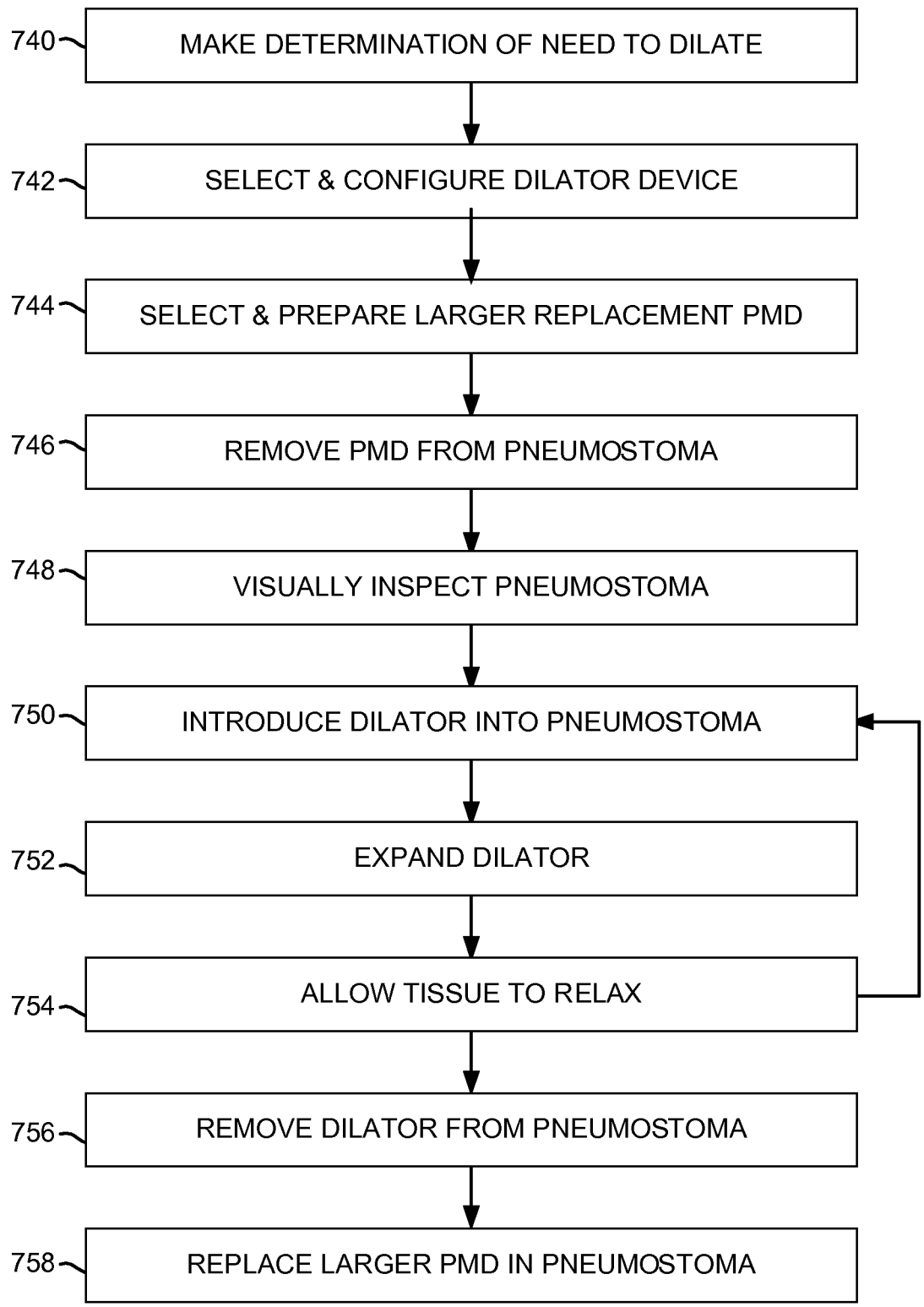
FIG. 7E is a flow chart illustrating steps for treatment of a pneumostoma with a mechanical instrument for dilating the pneumostoma according to an embodiment of the invention.

FIG. 7E illustrates a method for treatment of a pneumostoma with a dilator. First, based on, for example, information from the patient or observation of the pneumostoma, the physician makes a determination to treat the pneumostoma with a dilator. (step 740). The physician next selects and/or configures a dilator suitable to treat the pneumostoma of a particular patient. (step 742). The selected instrument is preferably sized such that it can be introduced into the pneumostoma and placed at a desired depth in the pneumostoma. As pneumostomas may vary in size, the dilator may have a configurable size, or a range of initial sizes. Thus selection of the dilator includes selecting/configuring the dilator for the pneumostoma of a particular patient such that it may be inserted into the pneumostoma to the desired depth prior to dilation. After dilation of the pneumostoma it is preferable to insert a PMD to support the pneumostoma as soon as the dilator is removed. Therefore, it is preferable to select and prepare a larger PMD for the patient to fit the anticipated dilated pneumostoma (step 744).

After the dilator and replacement PMD are, the original (smaller) pneumostoma management device will be removed from the pneumostoma (step 746). The pneumostoma should then be externally inspected (step 748) to determine whether there are any contraindications to use of the dilator, for example any obstruction of the pneumostoma which must first be removed. If the visual inspection reveals no contraindications, the dilator is introduced into the pneumostoma (step 750). The physician may then expand the dilator incrementally (step 752). The physician will then allow the tissue of the pneumostoma to relax (step 754) and repeat the incremental expansion (step 752) until the desired dilation has been achieved. The physician may also repeat the dilation at one or more depths within the pneumostoma depending upon the length of the pneumostoma. When the dilation is complete the dilator is removed (step 756). A new larger PMD should then be promptly inserted into the pneumostoma by the physician, or by the patient under the observation of the physician (step 758).

In some cases, treatment with the dilator is made in conjunction with inspection of the pneumostoma with a pneumoscope. In such case, the pneumoscope may be used before and after treatment to observe effects of the treatment upon the tissue of the pneumostoma and to ensure all deleterious materials have been removed from the pneumostoma. It may also be desirable to clean the pneumostoma with suction/irrigation prior to reinsertion of the PMD in order to remove any materials that may have been dislodged during the treatment.

Figure 7F:
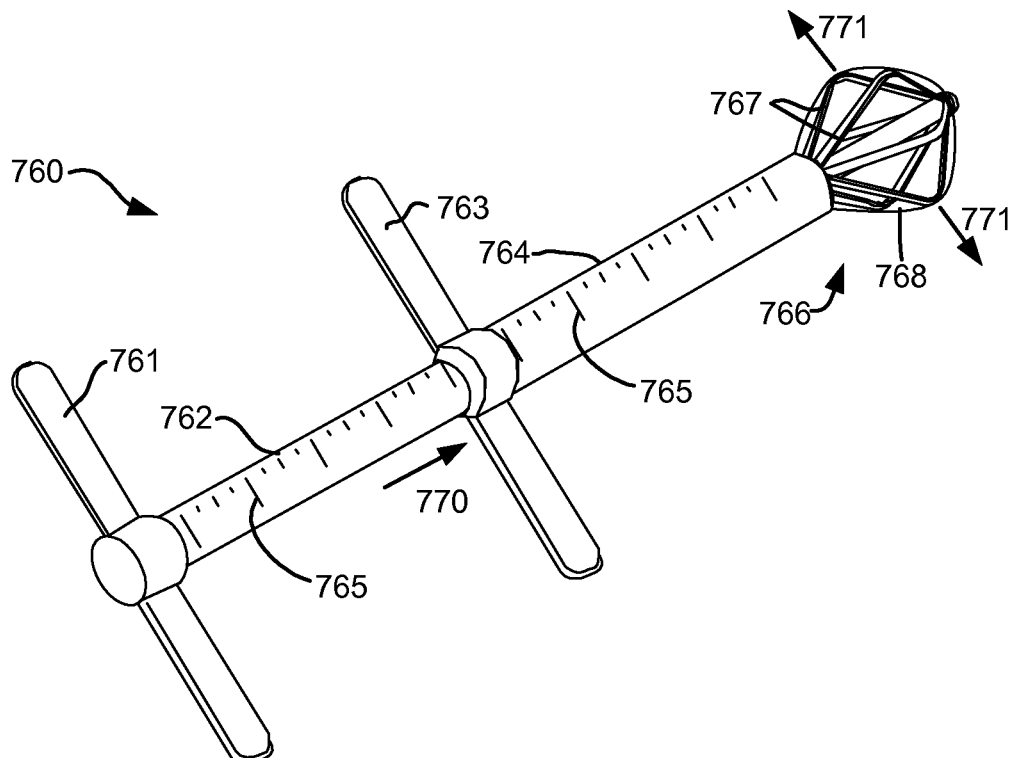
FIG. 7F shows an alternative mechanical instrument for dilating the pneumostoma or a portion of the pneumostoma according to an embodiment of the present invention.
Figure 7G:
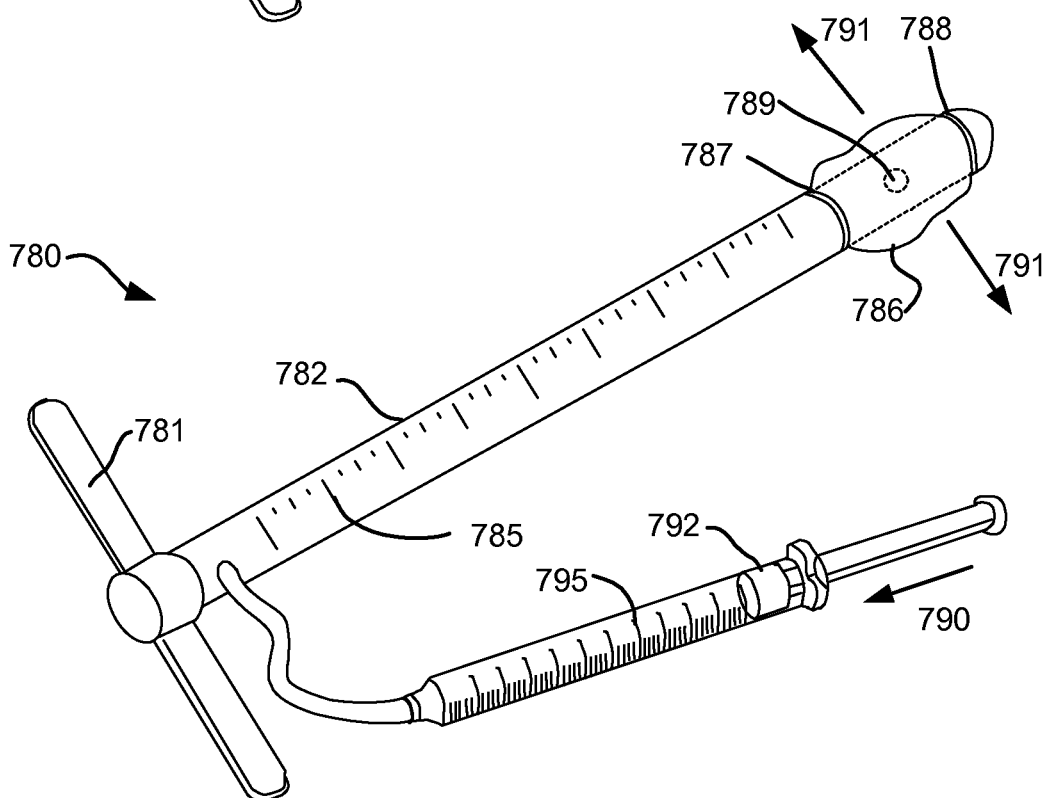
FIG. 7G shows an alternative mechanical instrument for dilating the pneumostoma or a portion of the pneumostoma according to an embodiment of the present invention.

Alternative means may be used to dilate the pneumostoma in alternative embodiments. FIG. 7F shows an alternative mechanical dilator 760 and FIG. 7G shows a balloon dilator 780. Referring to FIG. 7F, mechanical dilator 760 comprises first handle 761 connected to inner shaft 762 which extends to the distal tip of the mechanical dilator 760. A second handle 763 is connected to an outer shaft 764 which rides on inner shaft 762. At the distal end of mechanical dilator 760 is expander 766. Expander 766 includes a plurality of flexible elements 767 covered by a polymer shell 768. The distal end of each flexible element 767 and polymer shell 768 is connected to the distal end of inner shaft 762. The proximal end of each flexible element 767 and polymer shell 768 is connected to the distal end of outer shaft 764. When outer shaft 764 is pushed distally along inner shaft 762 (as shown by arrow 770), flexible elements 767 bend or bow outwards (as shown by arrows 771). Elements 767 push on polymer shell 768 causing it to also bow outwards (in the direction of arrows 771). Thus mechanical dilator 760 transitions from the collapsed configuration to the expanded configuration by pushing handle 763 distally relative to handle 761. Both outer shaft 764 and inner shaft 762 have markings 765 on the exterior surface so the physician may assess the depth of insertion of mechanical dilator 760 and the diameter of expansion of mechanical dilator 760. Mechanical dilator 760 may be used in the same way as dilator 700 of FIGS. 7A-7D, either for dilating the pneumostoma or assessing the diameter of the pneumostoma. Mechanical dilator 760 may additionally be provided with a locking device to hold it in an expanded position and/or a limit device to control expansion of the expander 766.

FIG. 7G shows a balloon dilator 780. Referring to FIG. 7F, mechanical dilator 780 comprises first handle 781 connected to a hollow shaft 782 which extends to the distal tip of the balloon dilator 780. At the distal end of mechanical dilator 780 is balloon 786. Balloon 786 is sealed to the hollow shaft at the proximal end 787 and distal end 788 of balloon 786. An aperture in hollow shaft 782 communicates between the lumen of the hollow shaft 782 and the interior of balloon 786. A syringe 792 is connected to the proximal end of hollow shaft 782. When syringe 792 is compressed (as shown by arrow 790), a liquid such as sterile saline is pushed through hollow shaft 782 into balloon 786 causing balloon 786 to inflate (as shown by arrows 791). Thus balloon dilator 780 transitions from the collapsed configuration to the expanded configuration by compressing syringe 792. Hollow shaft 782 has markings 785 on the exterior surface so the physician may assess the depth of insertion of balloon dilator 780. Syringe 792 has exterior markings 795 so that the physician may assess the volume of balloon 786 and hence the diameter to which it has been expanded. Balloon dilator 780 may be used in the same way as dilator 700 of FIGS. 7A-7D, either for dilating the pneumostoma or assessing the diameter of the pneumostoma.

Balloon 786 may be formed of a relatively inelastic material. In such case, injection of the liquid into the balloon will expand the balloon to a preset size. This ensures that the balloon does not stretch the pneumostoma more than desired. Moreover, the balloon can be expanded at high pressure without risk of over-expansion. However, a number of different balloon dilators may be required having different sizes in order to treat different pneumostomas or to incrementally expand a single pneumostoma. In alternative embodiments, a relatively elastic material may be used to make balloon 786. In such case, the balloon will have a larger diameter for larger amounts of liquid allowing broader application. However, the pressure applied by the balloon to the tissue will be lower than for an inelastic balloon.

Pneumostoma Treatment Using Localized Thermotherapy

The treatment modalities available for treating a pneumostoma include the application of heat (thermotherapy) or cold (cryotherapy). Thermotherapy and cryotherapy can be used to affect physical characteristics of tissues and cell proliferation and also to treat infection. For example, the tissues of the pneumostoma tend to encroach into the lumen of the pneumostoma thereby impairing the function of the pneumostoma. One way to reduce tissue encroachment is through the use of thermotherapy or cryotherapy thereby maintaining or enhancing the patency of the pneumostoma. In some embodiments a pneumostoma treatment device may be used to heat the tissue in others the pneumostoma treatment device may be used to cool the tissue to achieve the desired effects.

In one method of thermotherapy, a surface of a pneumostoma treatment device is brought into contact with a target tissue of the pneumostoma. The surface of the pneumostoma treatment device is then heated to raise the temperature of the target tissue (e.g. by electrical heating, laser heating, or by circulating a heated medium). Other methods of thermotherapy include application of focused ultrasound, infrared light, radio or microwave-frequency radiation to the target tissue to induce the desired temperature rise in the target tissue. For example, thermotherapy treatment device may direct energy at the tissue to heat the target tissue. The energy may be supplied as ultrasound, electrical energy, electromagnetic energy (for example IR or laser energy). The treatment is applied for a selected period of time. After the treatment the tissue is reassessed and treated again as necessary. The treatment may be applied to the pneumostoma tissue using a range of treatment devices and modalities as described in more detail below. In preferred embodiments, the temperature and duration of the heat treatment are selected to affect physical characteristics of tissues, reduce cell proliferation and/or treat infection but not to kill tissues of the pneumostoma.

Methods of cryotherapy include placing the target tissues in thermal contact with a cooled device or medium to lower the temperature of the target tissue. Cryotherapy may be used in two modes. The first mode of cryotherapy is cryogenic ablation in which cryotherapy is used to freeze tissue. A device is used to lower the temperature of the target cells to temperatures below freezing for short periods of time. The cells in the frozen tissue die and the tissue is removed. However, it is a disadvantage of tissue ablation that the cell necrosis stimulates the healing response. The healing response causes cell proliferation and generation of more cells in the form of scar tissue. As a result, cryogenic ablation may ultimately lead to greater tissue encroachment rather than less tissue encroachment. Cryogenic ablation may however still be useful for treating regions where tissue is encroaching into the pneumostoma.

A second mode of cryotherapy is cryogenic cooling in which cells are cooled below physiologic temperatures without freezing the cells. A device is used to lower the temperature of the target cells to temperatures between normal physiologic temperatures and a temperature above freezing for short periods of time. Cryogenic cooling has been found to reduce hyperplasia in blood vessels. See e.g. U.S. Pat. No. 6,811,550 entitled "Safety Cryotherapy Catheter" to Holland et al. Cryogenic cooling may also be used to his mode of cryotherapy to treat larger areas of the pneumostoma including up to the entire pneumostoma. In preferred embodiments, the temperature and duration of the cryotherapy are selected to affect physical characteristics of tissues, reduce cell proliferation and/or treat infection but not to kill tissues of the pneumostoma.

Figure 8A:
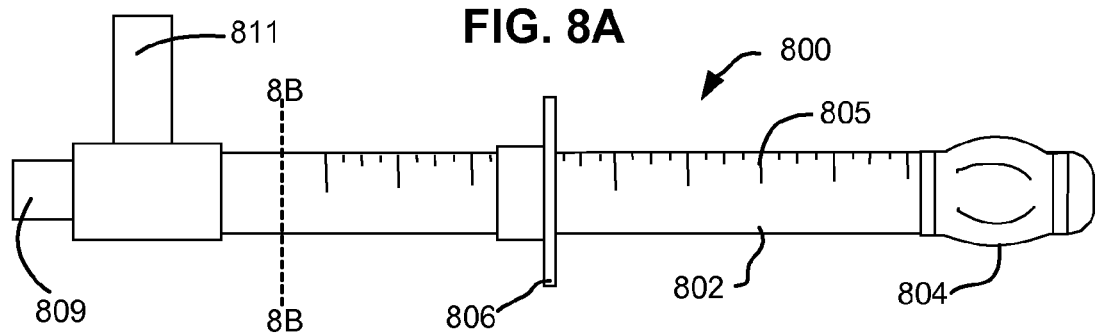
FIGS. 8A-8C show views of a thermotherapy device for treating tissues of a pneumostoma according to an embodiment of the present invention.
Figure 8B:
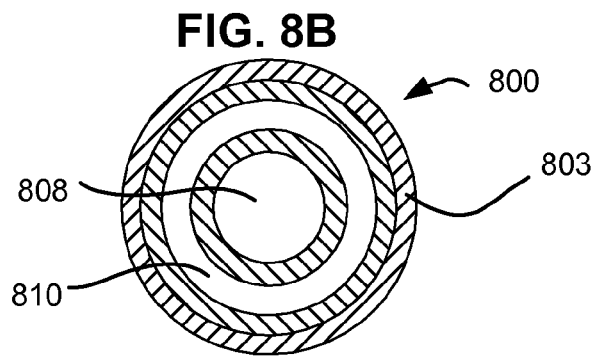
Figure 8C:
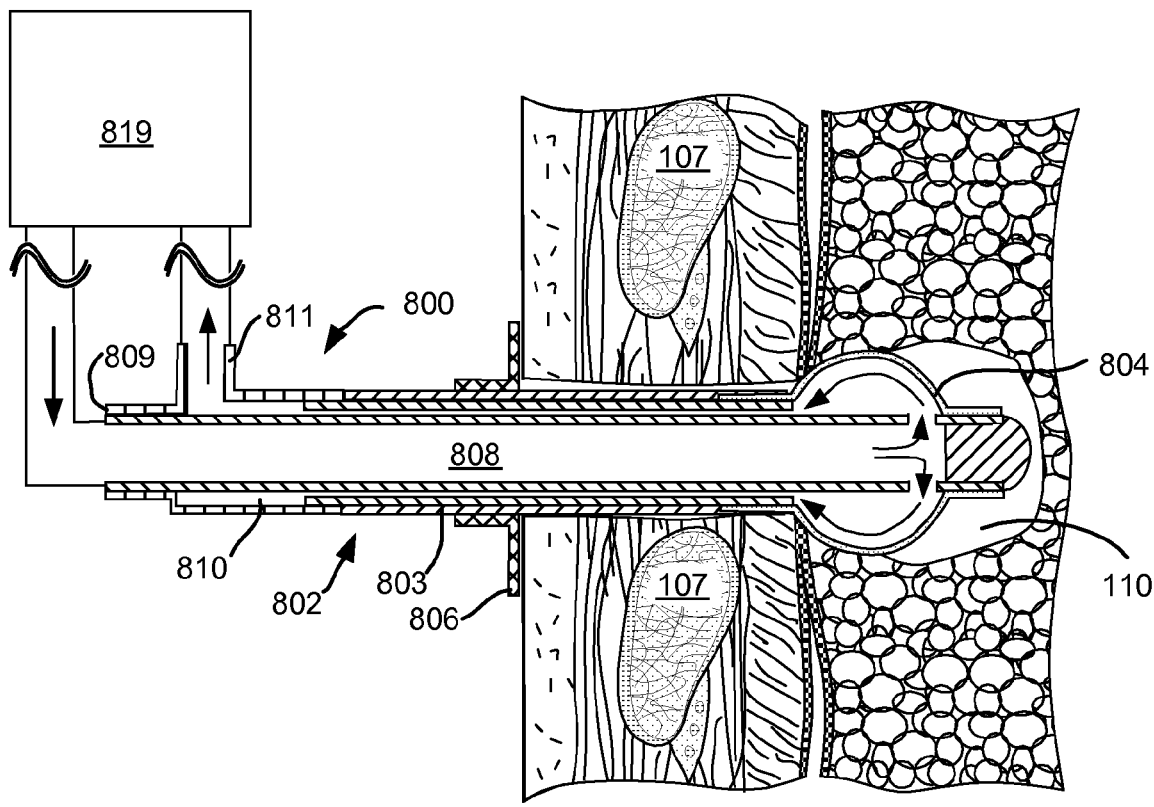

FIGS. 8A-8C show a catheter which may be used for cryotherapy or thermotherapy of a pneumostoma tissues. As shown in FIG. 8A, catheter 800 includes a shaft 802, a balloon 804 and a flange 806. Flange 806 slides on the exterior of shaft 802 and acts as a mechanical stop for insertion of shaft 802 into a pneumostoma. The positioning of flange 806 on shaft 802 allows the physician to control the depth of balloon 804 and thus the location of the treatment area. The shaft 802 is provided with external markings 805 to indicate the distance between the treatment area and flange 806 thereby facilitating application of the treatment to the desired target tissues.

As shown in FIG. 8B, shaft 802 has two lumens in inner lumen 808 and outer lumen 810. In some embodiments shaft 802 may be coated with an insulating layer 803 so that treatment is limited to the region of the balloon 804. The balloon may then be moved to different locations in the pneumostoma to treat different areas. In other embodiments, shaft 802 is not insulated and is also designed to treat the tissues of the pneumostoma in addition to the balloon. In such cases, it is preferable that treatment is performed at a single position (because to do otherwise would treat areas along the shaft 802 multiple times). As shown in FIG. 8C, at the proximal end of shaft 802 are an inlet 809 which communicates with inner lumen 808 and an outlet 811 which communicates with outer lumen 810.

As used for cryotherapy, catheter 800 is introduced in to the pneumostoma 110 to a depth limited by flange 806 as shown in FIG. 8C. Cryotherapy catheter 800 is connected to a cryotherapy coolant system 819 which supplies a temperature-controlled coolant fluid to cryotherapy catheter 800. A coolant fluid is introduced through inlet 809 into inner lumen 808. The coolant passes through inner lumen 808 to the distal end of cryogenic catheter 800. The coolant passes through an aperture out of inner lumen 808 into the balloon 804. The coolant inflates balloon 804 to bring it into contact with the tissue of the pneumostoma 110. The coolant circulates around balloon 804 and cools the surface of balloon 804 to the desired temperature. The coolant then returns through the outer lumen 810 and exits the catheter via the outlet 811. In some embodiments, a temperature sensor may be included in the distal tip of cryotherapy catheter 800 in order to monitor the temperature of the balloon. However, in other embodiments, temperature regulation is performed by regulating the temperature of the coolant supplied by the cryotherapy coolant system.

The coolant fluid is preferably a non-toxic liquid such as saline. However, liquids other than saline may be used and in some cases the coolant fluid may be a temperature-controlled gas. One system for supplying coolant is described in U.S. Pat. No. 6,432,102 entitled "Cryosurgical Fluid Supply" to Joye et al. If thermotherapy of the tissues is desired, a fluid heated to above body-temperature may be used in place of the coolant.

Figure 8D:
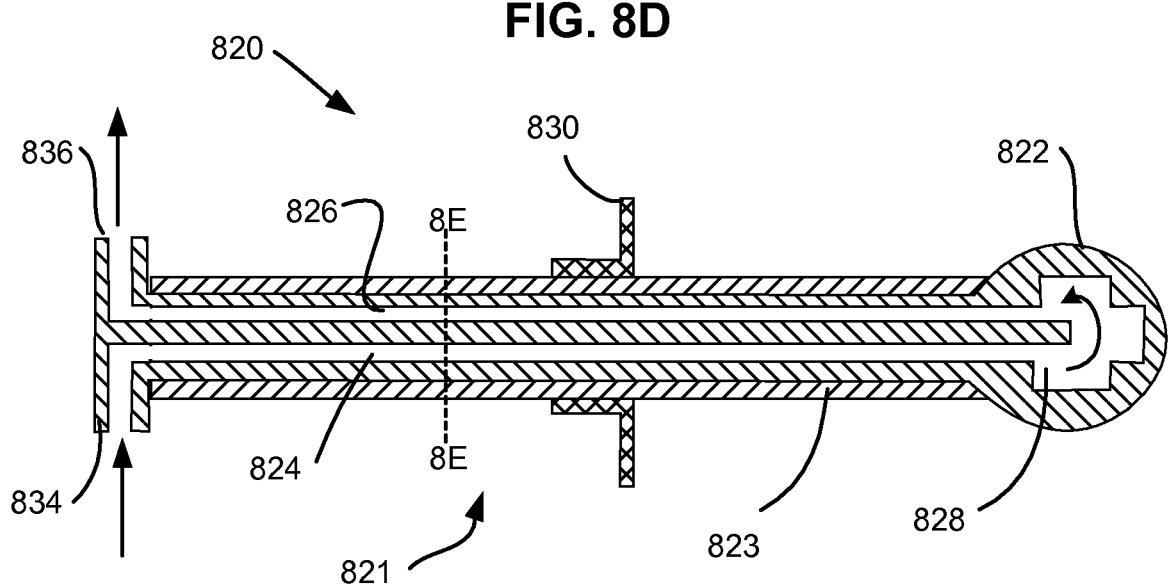
FIGS. 8D-8E show views of an alternate thermotherapy device for treating tissues of a pneumostoma according to an embodiment of the present invention.
Figure 8E:
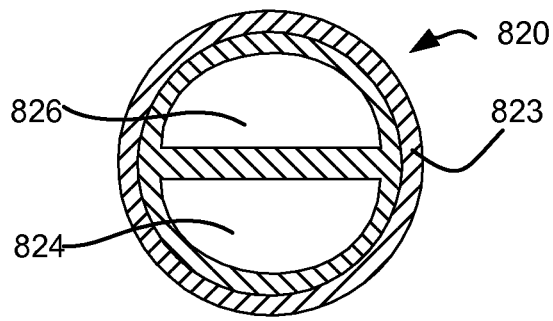

FIG. 8D shows an alternative cryotherapy probe 820. Cryotherapy probe 820 includes a shaft 821 and tip 822. Tip 822 is of fixed size and is preferably made of a heat conductive material. Tip 822 may be made in whole or in part of a biocompatible metal, for example surgical steel. Tip 822 may be made in one piece with shaft 821 or may be made separately and joined to shaft 821. As shown in FIG. 8E, shaft 821 (shown in FIG. 8D) includes two lumens 824, 826 for supplying coolant to tip 822 (in FIG. 8D). Tip 822 has a cavity 828 in which the coolant circulates. At the proximal end of cryotherapy probe 820 is an inlet 834 which communicates with lumen 824 and an outlet 836 which communicates with lumen 826. In some embodiments, shaft 820 may be coated with an insulating layer 823 so that treatment is limited to the region of the tip 822. Shaft 821 may be coated with an insulating material 823 in order that the cryotherapy treatment is localized to the region of tip 822. The tip 822 may then be moved to different locations in the pneumostoma to treat different areas.

The size of tip 822 may differ between different cryotherapy probes 820. A physician may have a range of cryotherapy probes available and choose the cryotherapy probe based upon the anatomy of the pneumostoma and the size and location of the tissues to be treated. Cryotherapy probe 820 may optionally be provided with a flange 830 positionable along shaft 821 in order to limit insertion of tip 822 into the pneumostoma and thereby control the location of tip 822 and the location of the cryotherapy treatment site.

In use, cryotherapy probe 820 is introduced into a pneumostoma to a position indicated by the markings on the exterior of the shaft 821 or position of the flange 830. Tip 822 is brought into thermal contact with the pneumostoma tissues to be treated. Cryotherapy probe 820 is connected to a cryotherapy coolant system 819. A coolant fluid is introduced through inlet 834 into lumen 824. The coolant passes through lumen 824 to the distal end of cryotherapy probe 820. The coolant passes through an aperture out of lumen 824 into the cavity 828. The coolant circulates around cavity 828 and cools the surface of tip 822 to the desired temperature. The coolant then returns through lumen 826 and exits the probe via the outlet 836. In some embodiments a temperature sensor may be included in the tip 822 of cryotherapy probe 820 in order to monitor the temperature of the tip. However, in other embodiments, temperature regulation is performed by regulating the temperature of the coolant supplied by the cryotherapy coolant system. For thermotherapy, a heated fluid may be circulated through the probe in place of the coolant.

Pneumostoma Treatment Using Electromagnetic Radiation

The treatment modalities available for treating a pneumostoma include the application of energy in the form of electromagnetic radiation, for example, infrared, ultraviolet, visible light, RF, microwaves. Such energy treatment can be used to affect physical characteristics of tissues and cell proliferation and also to treat infection. For example, the tissues of the pneumostoma tend to encroach into the lumen of the pneumostoma and/or thicken the walls of the pneumostoma thereby impairing the function of the pneumostoma. One way to reduce tissue encroachment and/or thickness is through the application of energy to the tissues, either to kill the cells or to reduce their proliferation thereby maintaining or enhancing the patency of the pneumostoma. In some embodiments a pneumostoma treatment device may be used to direct energy to particular localized regions of the pneumostoma tissue, in other embodiments, the pneumostoma treatment device may apply energy equally in all directions. In other embodiments, the electromagnetic radiation may be selected to kill or damage bacteria to reduce infection while minimizing damage to the cells of the pneumostoma. Some frequencies of visible light, for example, have been shown to kill certain bacteria without causing significant damage to human cells.

Figure 9A:
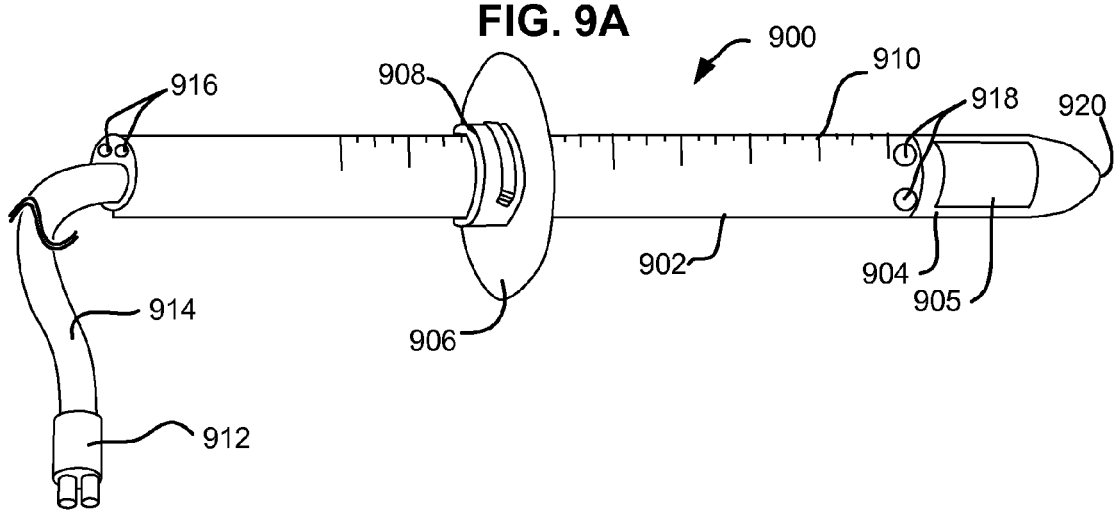
FIGS. 9A-9B show views of an electromagnetic treatment device for treating tissues of the pneumostoma according to an embodiment of the present invention.

FIG. 9A illustrates a pneumostoma treatment device 900 for treatment of pneumostoma tissues with electromagnetic radiation. The device includes a shaft 902 having at its distal end a treatment head 904. The treatment head has a tapered or rounded tip 920 to facilitate introduction into the pneumostoma. The treatment head 904 may generate electromagnetic radiation in situ, or the electromagnetic radiation may be transmitted from an external source to the treatment head 904. The treatment head may in some cases have a window 905 which is either open or covered with a material transparent to the electromagnetic radiation to be transmitted. In other cases the entire treatment head 904 may be enclosed in a material which is transparent to the delivered electromagnetic radiation.

At the proximal end the pneumostoma treatment device 900 has a coupling 912 for connecting the pneumostoma treatment device 900 to a power source which may provide the electromagnetic radiation directly or provide electrical power to create electromagnetic radiation in the treatment head 904. Coupling 912 may be connected to shaft 910 by a flexible cable 914. The proximal end of shaft 902 may also provide access to lumens 916 which communicate with apertures 918 adjacent treatment head 904. Lumens 916 and apertures 918 optionally provide suction, irrigation and/or cooling to the region adjacent treatment head 904 as necessary and/or desirable for a particular treatment modality.

The shaft 902 and treatment head 904 are of suitable diameter for insertion into a pneumostoma. Typically the shaft 902 and treatment head 904 will be less than approximately 10 mm in diameter. In some cases the shaft and treatment head may be approximately 5 mm in diameter. The shaft 902 is flexible enough to allow insertion of the treatment head 904 into a pneumostoma even when the pneumostoma is not entirely straight. The shaft 902 should however be stiff enough that it can provide adequate force to push the treatment head 904 to the correct location in the pneumostoma.

The pneumostoma treatment device carries a flange 906 which can slide on shaft 902. The flange 906 has a locking collar 908 to fix the flange 906 at an adjustable position along the shaft 902, other locking means may be used, for example, a suture, tape glue or mechanical lock. The physician will typically adjust the location of the flange 906 along the shaft 902 so that, when the treatment head 904 and shaft 902 are inserted to the desired depth into a pneumostoma, the flange contacts the chest of the patient, and prevents further insertion. Correct pre-positioning of the flange 906 on shaft 902 serves to guide treatment depth and protect against over insertion. The shaft 902 may also be provided with external markings 910 so that the physician may determine the correct location for flange 906 and the corresponding depth of treatment head 904.

Figure 9B:
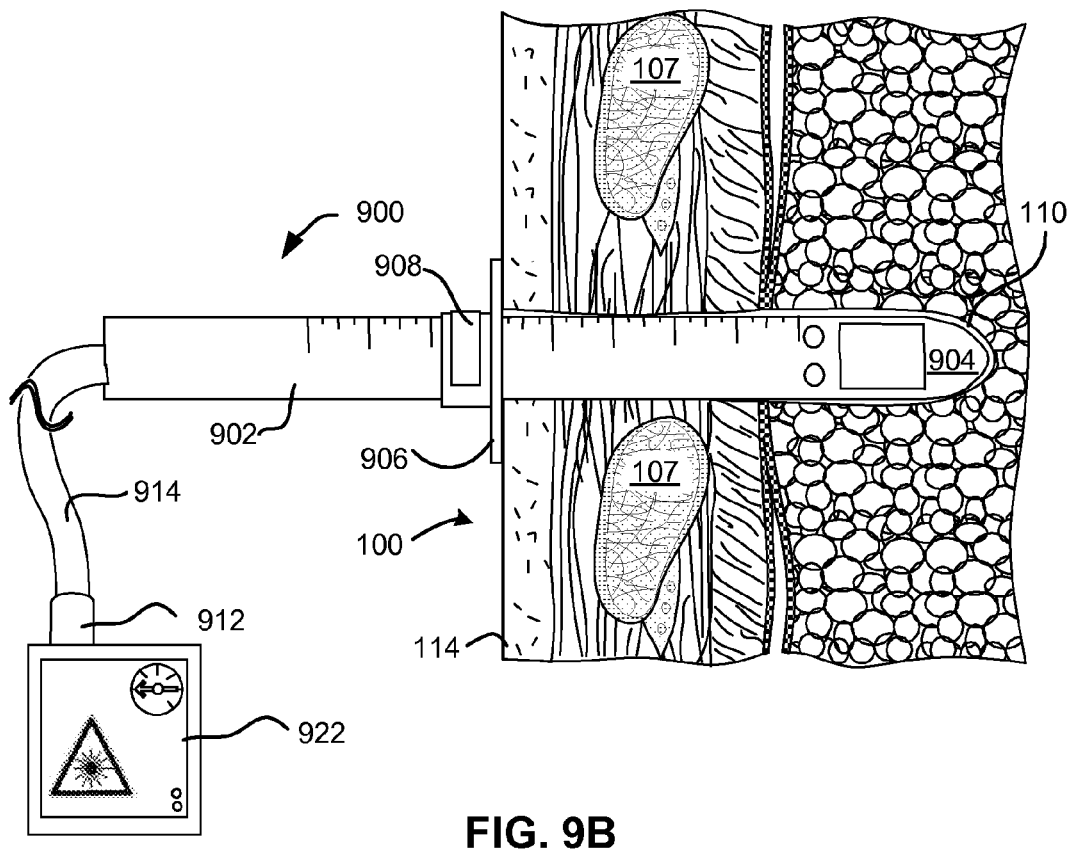

FIG. 9B shows a sectional view of pneumostoma treatment device 900 inserted into a pneumostoma 110. Note that flange 906 is in contact with the skin 114 of the chest 100 of the patient and thus acts as a mechanical stop to prevent further insertion. Flange 906 may additionally be provided with an adhesive (not shown) to temporarily secure the flange 906 to the skin 114 of the chest 100 of the patient thereby securing the treatment head 904 at the desired depth within the pneumostoma 110. Coupling 912 connects controller 922 via cable 914 to the proximal end of shaft 902 and via shaft 902 to treatment head 904. Controller 922 may be used to control the provision of electromagnetic radiation by treatment head 904. Controller may control one or more of: the location, intensity, wavelength and/or duration of the application of the electromagnetic radiation as directed by a physician.

The treatment head 904 may be designed so that it delivers electromagnetic radiation equally in all directions thereby treating uniformly all of the tissues adjacent the treatment head. In alternative embodiments treatment head 904 may be designed such that it applies the electromagnetic radiation in a directional manner—this adds additional complexity in that a mechanism needs to be provided for aligning the electromagnetic radiation with the target tissues. However, the directional solution allows for different tissues within the pneumostoma to be treated differently and also different regions to be treated differently from other regions. Directionality may be provided, for example, using scanning optics to aim a beam of electromagnetic radiation provided by controller 922 through a fiber optic cable.

Figure 9C:
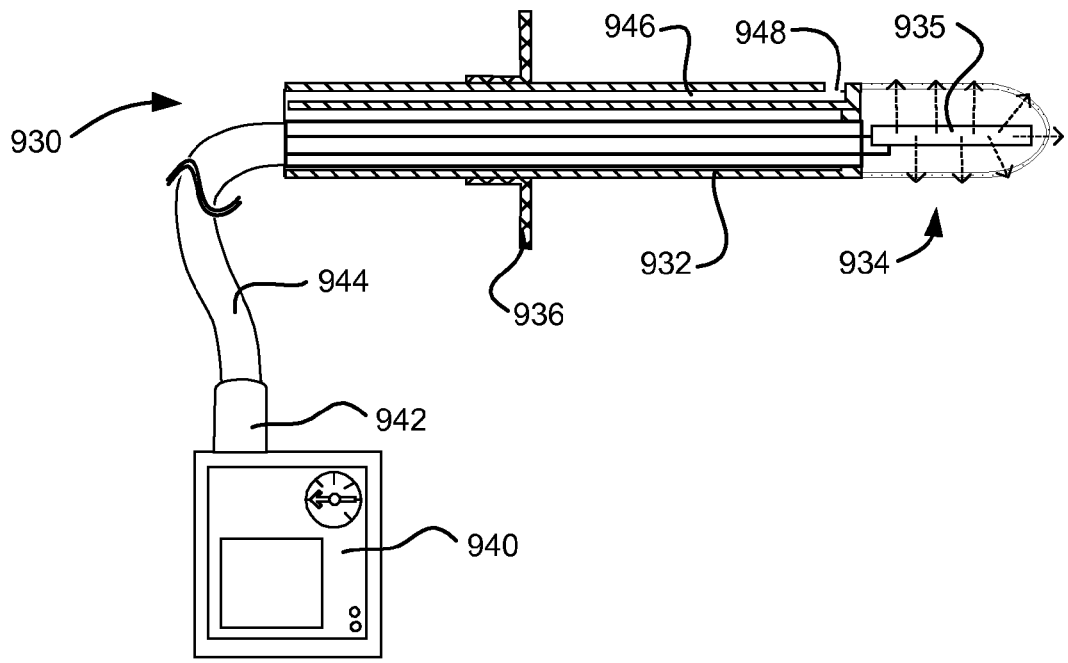
FIG. 9C shows a view of an alternate electromagnetic treatment device for treating tissues of the pneumostoma according to an embodiment of the present invention.

FIG. 9C shows a sectional view of a pneumostoma treatment device 930 for treatment of pneumostoma tissues with electromagnetic radiation. The device includes a shaft 932 having at its distal end a treatment head 934. The shaft 932 carries a flange 936 which can slide on shaft 932. One or more lumens 946 passes along the length of shaft 932 to one or more aperture 948 adjacent treatment head 934. Lumens 946 and apertures 948 optionally provide suction, irrigation and/or cooling to the region adjacent treatment head 934 as necessary and/or desirable to enhance treatment or protect tissue during treatment. At the proximal end the pneumostoma treatment device 930 has a coupling 942 for connecting the pneumostoma treatment device 930 to a power source 940 which provides electrical power through cable 944 to create electromagnetic radiation in the treatment head 934.

In the embodiment shown in FIG. 9C, the treatment head 934 generates electromagnetic radiation in situ. The treatment head 934 is enclosed in a material which is transparent to the delivered electromagnetic radiation. As shown in FIG. 9C the treatment head 934 radiates electromagnetic radiation in all directions uniformly from source 935 located within head 934. Source 935, generates the desired electromagnetic radiation from electrical power provided by power source 940. The source may be for example, a source of IR, UV visible light, X-rays or other electromagnetic radiation with which it is desired to treat the tissue of the pneumostoma. Particular devices suitable for use as source 935 include for example incandescent light sources, LEDs, fluorescent lamps and miniature X-ray sources. The source may be provided with additional features to ensure uniformity of distribution of the selected electromagnetic radiation including, for example a collimator, diffuser, and or reflector.

Figure 9D:
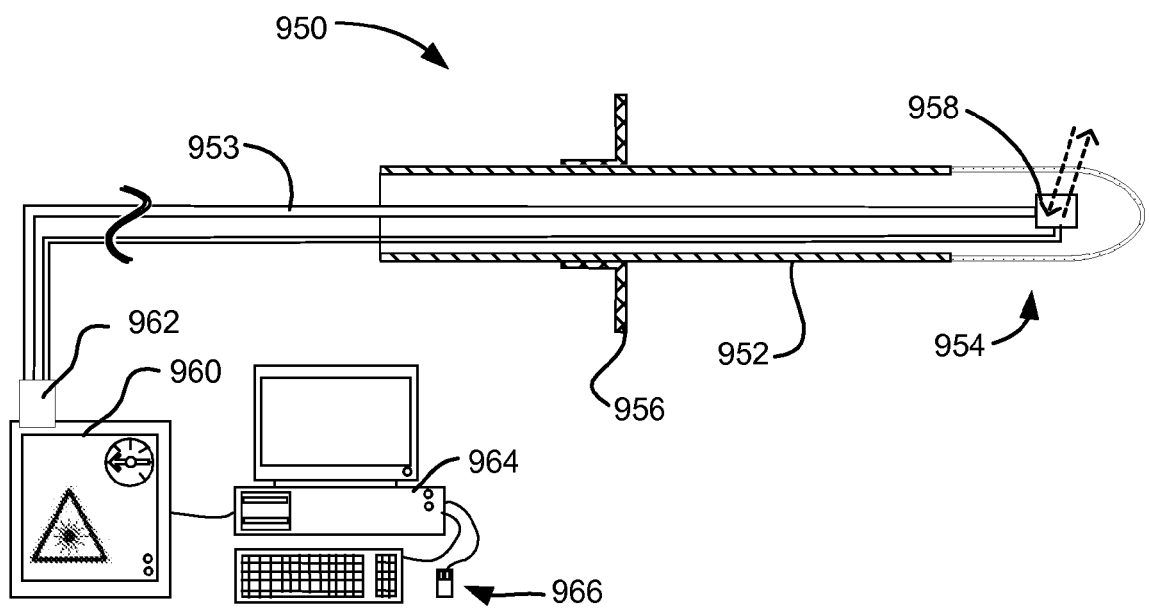
FIG. 9D shows a view of an alternate electromagnetic treatment device for treating tissues of the pneumostoma according to an embodiment of the present invention.

FIG. 9D shows a sectional view of a pneumostoma treatment device 950 for treatment of pneumostoma tissues with electromagnetic radiation. The device includes a shaft 952 having at its distal end a treatment head 954. The shaft 952 carries a flange 956 which can slide on shaft 952. Flange 956 may be locked to shaft 952 and secured to the chest of the patient so that head 954 may be secured in a fixed relation to the pneumostoma during operation of pneumostoma treatment device 950. At the proximal end the pneumostoma treatment device 950 has a coupling 962 for connecting the pneumostoma treatment device 950 to a controller 960 which provides light and power through cable 964 to treatment head 954.

In the embodiment shown in FIG. 9D, the treatment head 954 does not generate electromagnetic radiation in situ. Instead, the electromagnetic radiation is generated by controller 960 and transmitted through an optical fiber 953 to treatment head 954. The treatment head 954 is enclosed in a material which is transparent to the delivered electromagnetic radiation. As shown in FIG. 9D, the treatment head 954 includes scanning optics 958 which direct the electromagnetic radiation in a particular direction under the control of controller 960. Controller 960 generates the desired electromagnetic radiation, transmits it to head 954 which directs it to a particular region of tissue of the pneumostoma. Controller 960 is connected to a computer system 964 which provides the physician with an interface 966 to operate controller 960 and control head 954 to treat selected target tissues within a pneumostoma.

Controller 960 may generate one or more selectable frequencies of electromagnetic radiation. Controller 960 may, for example include a tunable laser source cable of generating coherent light over a range of different frequencies. The light frequency and intensity may be selected based upon the effect desired. For example, in some case the light frequency and intensity may be selected to ablate certain target tissues in the pneumostoma. Tissue ablation may be used to generate pores in the wall of the pneumostoma to enhance patency of the pneumostoma and/or restore pathways for gas to exit the pneumostoma.

In some embodiments, the scanning optics may also receive light received back from the tissue, which light may pass back down the fiber optic to controller 960. The received light may be analyzed using tissue spectroscopy and/or tomography techniques to determine properties of the particular tissue from which the light is received. In such way the head 954 can be used to analyze the tissue of the pneumostoma in addition to, or instead of, treating the tissue. Tissue scanning may be used in order to select target tissues for e.g. ablation to enhance the selectivity of treatment and reduce damage to sensitive tissue. For example, tissue scanning may be used to ensure that tissue ablation avoids blood vessels in proximity to the pneumostoma when forming pores to restore or enhance the exit of gas through the pneumostoma.

Because of the proximity of blood vessels to the surface of the pneumostoma, the pneumostoma may also be used as a port for analysis of compounds in the bloodstream. For example analysis of blood gases, and/or glucose concentration. The analysis can be performed by scanning the thin tissues of the pneumostoma and analyzing the light received from the tissues. Information in the received light at different frequencies and in a number of modes (for example scattering, reflectance, absorption and fluorescence) may be used to derive detailed information regarding the tissues of the pneumostoma and blood in vessels immediately adjacent the pneumostoma.

Further Techniques for Assessment of Pneumostoma Function

Methods and devices for assessing the functionality of a pneumostoma are described in FIGS. 3A-3D, 4A-4E and accompanying text. In a preferred system for assessing functionality of a pneumostoma, the patency is assessed by measuring/analyzing gases escaping from the pneumostoma under standard conditions. In order to induce a measurable flow through the pneumostoma it is desirable to increase the pressure in the parenchymal tissue of the lungs above ambient pressure so that gases are forced out through the pneumostoma. Additionally, it is desirable to increase the pressure in the parenchymal tissue of the lungs by a selected and/or standard amount above ambient pressure so the analysis of pneumostoma function can be compared with result obtained at different times and/or with different patients. By providing standardized parenchymal pressure for the assessment, a standardized repeatable measure can be obtained that has clinical relevance to the function of the pneumostoma and can be used to identify appropriate pneumostoma treatment timing and modality.

During normal tidal breathing, the pressure differential between gases in the parenchymal tissue in the lung and atmospheric pressure is between about −4 and −10 cm $H_2O$ (−392 and −980 Pa) during inhalation and +4 and +10 cm $H_2O$ (+392 and +980 Pa) during exhalation. The pressure of gases in the parenchymal tissue of the lung during tidal breathing depends upon a variety of factors including the general health, pulmonary health, strength, and motivation of the patient on the day of assessment. Thus, the pressure of gases in the parenchymal tissue of the lung can vary over time in a single patient and also varies widely between patients. Thus, pressure of gases in the parenchymal tissue of the lung during tidal breathing creates a pressure differential across the pneumostoma which is relatively low and very variable.

The pressure in the parenchymal tissue of the lung can be increased by the patient by forcible exhalation against a closed airway known as the Valsalva maneuver. In the Valsalva maneuver a patient can raise the pressure in the parenchymal tissue in the lung substantially—including, for example, +30 cm $H_2O$ (+2940 Pa). However, the peak pressure achieved depends upon the general health, pulmonary health, strength, and motivation of the patient on the day of assessment. Thus, the pressure of gases in the parenchymal tissue of the lung achieved and/or sustained through the Valsalva maneuver can vary over time in a single patient and also varies widely between patients. Furthermore, the Valsalva maneuver also reduces cardiac output while increasing $CO_2$ concentration and thus may not be comfortably tolerated in patients who have cardiac and/or respiratory dysfunction. Thus, neither tidal breathing nor the Valsalva maneuver can provide a standard/uniform elevated pressure differential desirable for obtaining a repeatable measure of pneumostoma function.

FIGS. 10A-10F illustrate aspects of a variety of pneumostoma diagnostic systems and devices useful for assessing pneumostoma patency/function. In general terms, the pneumostoma diagnostic systems include an airway interface and a pressure elevation device. The pressure elevation device is coupled to the patient through the airway interface and elevates the pressure in the patient's lung to a selected pressure. The pneumostoma diagnostic systems also include a pneumostoma interface for collecting gases from the pneumostoma and a gas analyzer. The gas analyzer is coupled to the pneumostoma by the pneumostoma interface and analyzes the amount of gas in and/or exiting the pneumostoma, including, e.g., flow, volume, pressure and concentrations of gases.

Figure 10A:
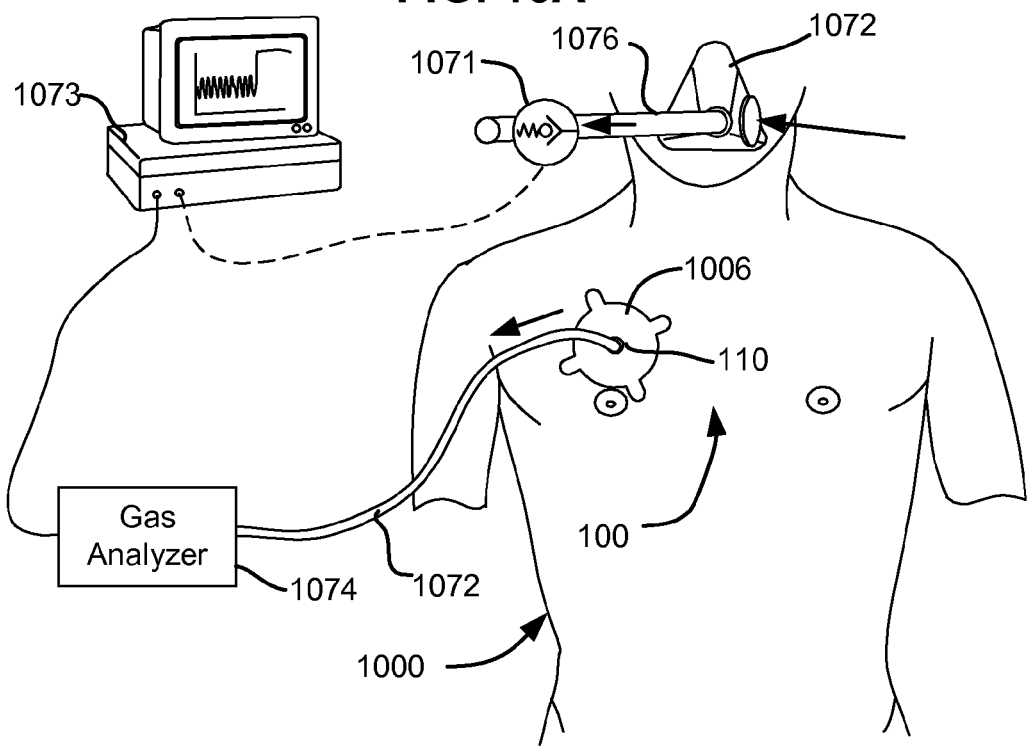
FIG. 10A shows a pneumostoma diagnostic system for elevating the pressure in the lungs and measuring/analyzing gas exhaled through a pneumostoma according to an embodiment of the present invention.
Figure 10B:
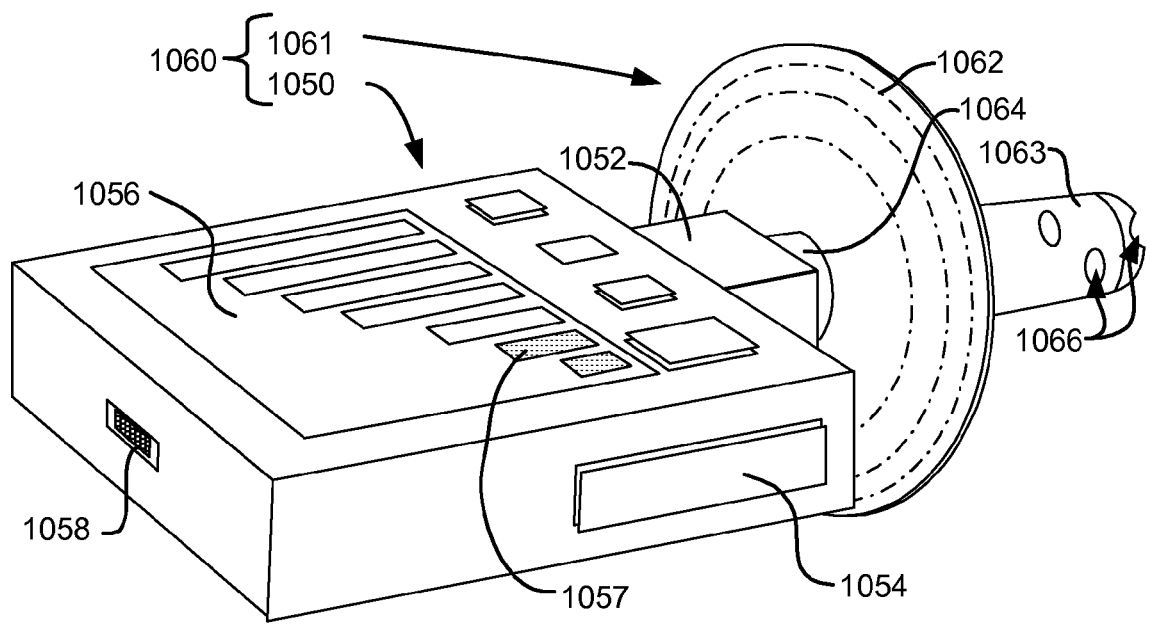
FIG. 10B shows a portable pneumostoma diagnostic system for measuring/analyzing gas exhaled through a pneumostoma, during elevated-pressure exhalation, according to an embodiment of the present invention.
Figure 10D:
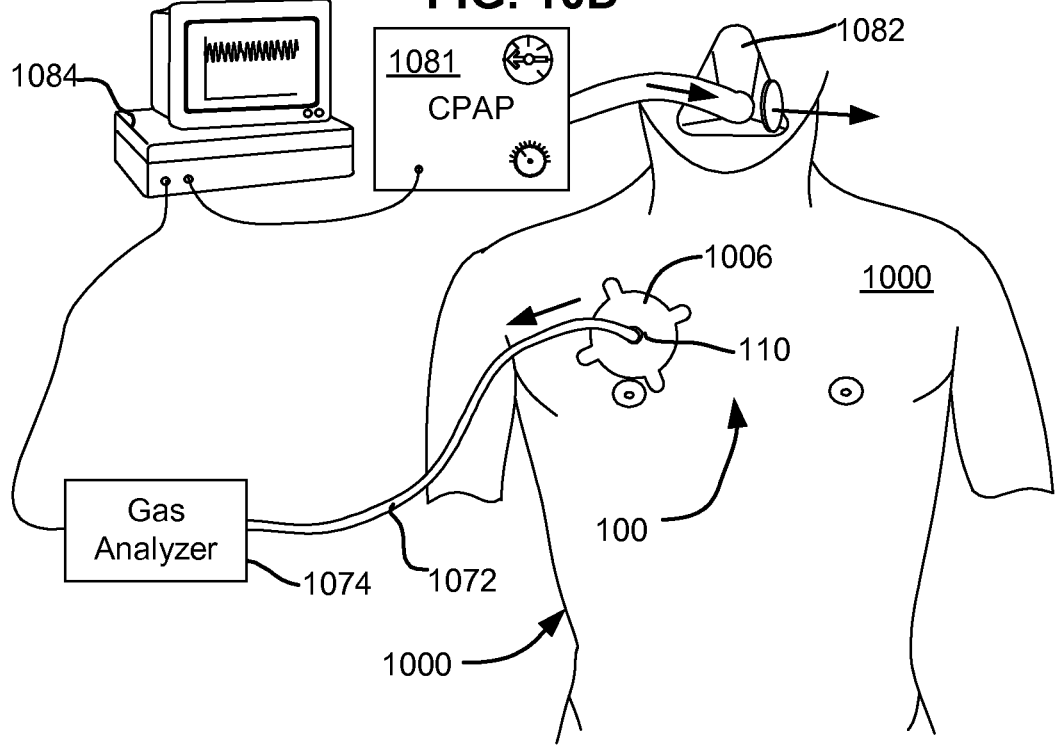
FIG. 10D shows a system combining a diagnostic system and a CPAP machine for elevating the pressure in the lungs and measuring/analyzing gas exhaled through a pneumostoma, according to an embodiment of the present invention.
Figure 10E:
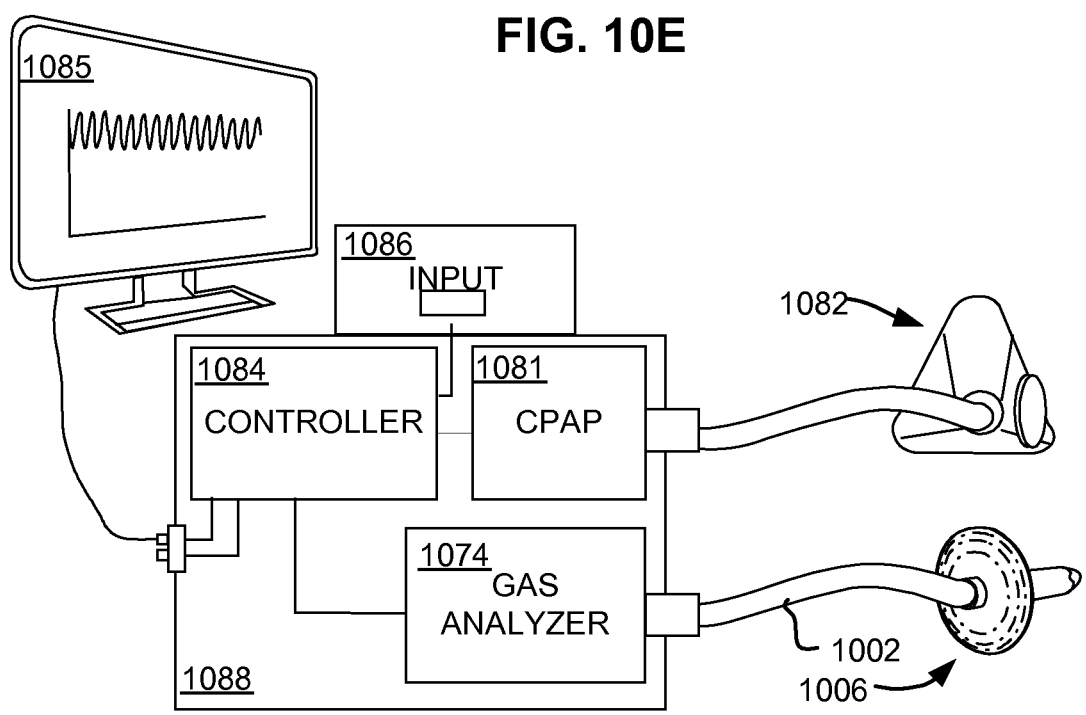
FIG. 10E shows an integrated pneumostoma diagnostic system which elevates the pressure in the lungs and measures/analyzes gas exhaled through a pneumostoma according to an embodiment of the present invention.
Figure 10F:
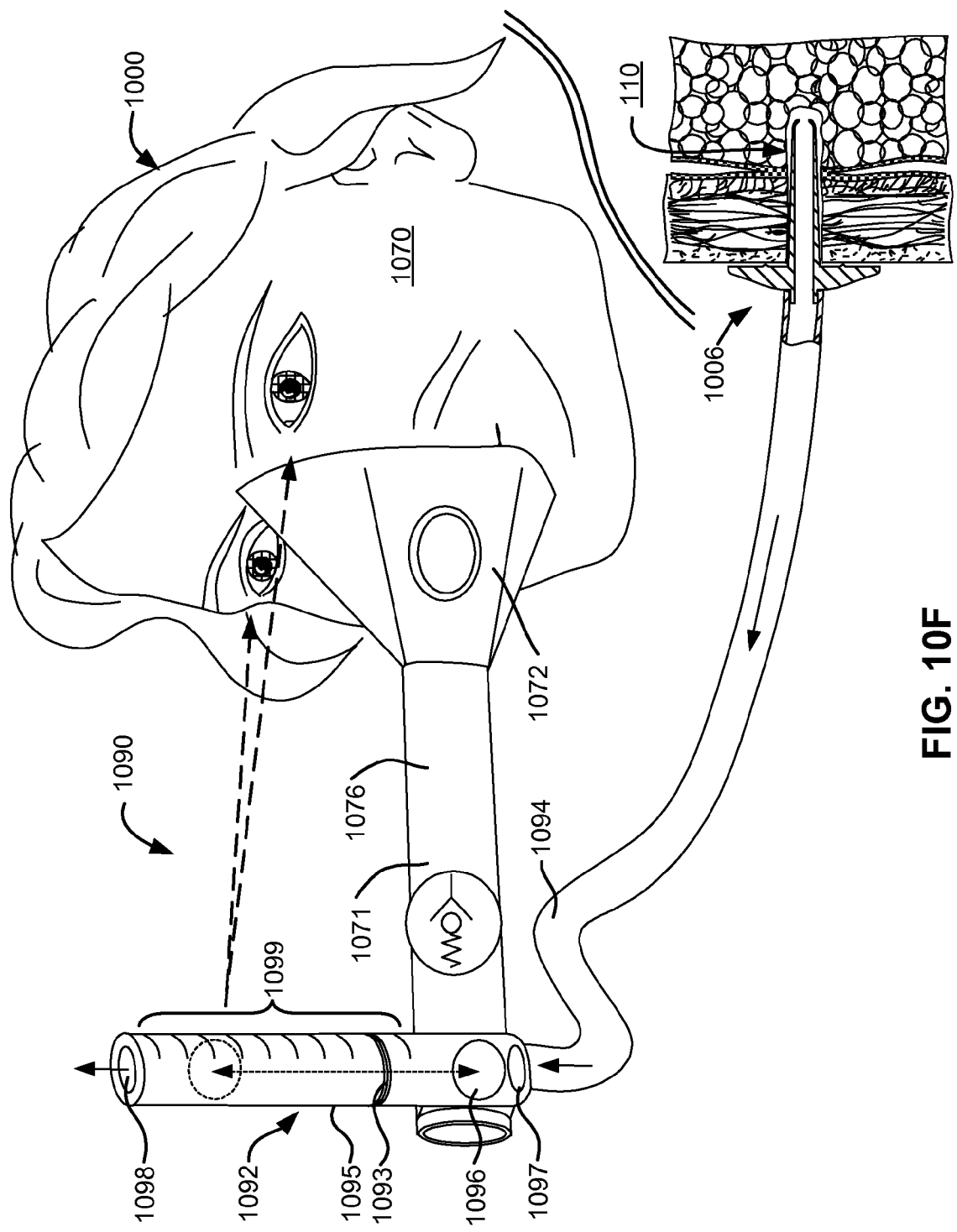
FIG. 10F shows a mechanical pneumostoma diagnostic device, suitable for patient use, which elevates the pressure in the lungs and measures/analyzes gas exhaled through a pneumostoma according to an embodiment of the present invention.

FIG. 10A shows a pneumostoma diagnostic system for elevating the pressure in the lungs and measuring/analyzing gas exhaled through a pneumostoma. FIG. 10B shows a portable pneumostoma diagnostic system for measuring/analyzing gas exhaled through a pneumostoma. FIG. 10C shows a method for using a pneumostoma diagnostic system. FIG. 10D shows a system combining a diagnostic system and a CPAP machine for elevating the pressure in the lungs and measuring/analyzing gas exhaled through a pneumostoma. FIG. 10E shows an integrated pneumostoma diagnostic system including a positive pressure generator and gas analyzer. FIG. 10F shows an all-mechanical pneumostoma diagnostic device, suitable for patient use. Although particular combinations of elements are illustrated, alternative embodiments include different combinations of positive-pressure systems and gas analysis systems.

Referring first to FIG. 10A which illustrates a device useful for enabling a modification of the Valsalva maneuver in which the patient 1000 exhales against a pressure-actuated valve 1071 instead of a closed airway. The valve is in some cases a mechanical pressure-actuated valve. For example the pressure-actuated valve 1071 is in some cases a check valve with a controlled crack pressure (pressure at which valve allows gases to escape). In a preferred embodiment the valve is set to release gas once a predetermined pressure has been achieved by a patient. Thus the patient can exhale at a selected elevated pressure thereby raising the pressure in the parenchymal tissue of the lung. Suitable pressures include pressures between 5 and 30 cm $H_2O$ (492 and 2940 Pa). However, it is preferable to choose, as a standard pressure, a pressure that can be comfortably sustained by all patients. Thus, a standard pressure can be selected from a range of pressures, for example, 5, 10 or 15 cm $H_2O$. (492, 980 or 1470 Pa).

In alternative embodiments, pressure-actuated valve 1071 is electronically-controlled, by means of an electronically-operated valve which opens in response to an electronic pressure sensor, to open at the selected pressure. In some embodiments the valve 1071 interfaces with a controller 1073 which can record the pressure from a sensor and/or control release of air by an electronically-operated valve. Forced exhalation against the pressure-actuated valve 1071 allows the patient to achieve and sustain a selected elevated pressure in the gases of the parenchymal tissue of the lung for a time during a test of pneumostoma function.

As shown in FIG. 10A, an airway interface 1072 connects pressure-actuated 1071 to the patient 1000. Airway interface 1072 is in some case a mask that seals to the face as shown. Where a mask is used an inlet valve is provided to allow entry of air during inhalation. Airway interface is, in alternative embodiments, a simple tube that the patient 1000 blows into while sealing to the tube with his mouth and preventing air from exiting through his nose. Where a tube is used, the patient can inhale through his nose or around the tube or through an inlet valve (one-way). A lung exercise device called the POWERLUNG® available from PowerLung, Inc. (Houston, Tex.) allows control of minimum positive exhale pressure using a check valve with selectable crack pressure and also control of minimum negative pressure for inhale using another check valve with selectable crack pressure. The POWERLUNG® device is described in U.S. Pat. No. 6,726,598 entitled "Pulmonary Exercise Device" to Jarvis et al. which is incorporated herein by reference.

Referring again to FIG. 10A, a pneumostoma interface 1006 such as gas analysis device 400 of FIG. 4D, is inserted into the pneumostoma 110 of a patient 1000. In general terms, pneumostoma interface 1006 is a gas collection device which can be secured into a pneumostoma for sampling gases exiting the pneumostoma. Pneumostoma interface 1006 is connected by flexible inelastic tube 1072 to a gas analyzer 1074. One or more filters and/or isolation devices may be interposed between pneumostoma interface 1006 and gas analyzer 1074 to prevent possible contamination of the sensor and/or cross-contamination between patients.

The gases exiting the parenchymal tissue of the lung through pneumostoma 110 (also referred to as gases exhaled through the pneumostoma) are measured and/or analyzed during a period of elevated pressure in the parenchymal tissue of the lung (for example the elevated pressure during forced exhalation against the pressure-actuated valve). For example, the pressure, volume and/or flow of gas exiting the pneumostoma may be measured by gas analyzer 1074 to provide information regarding the patency/functionality of the pneumostoma. The exhaled gas may be also be analyzed by gas analyzer 1074 to determine oxygen and carbon dioxide concentrations. In some cases, the concentrations are compared to oxygen and carbon dioxide concentrations in the gases exhaled through the natural airways or in the ambient atmosphere. Such evaluation may be useful in determining the effectiveness of a pneumostoma and the location and/or desirability of additional pneumostomas. As one example, gas analyzer 1074, includes, in some embodiments, a gas flow measurement device which measure and records gas data, such as gas volume and gas flow out of the pneumostoma. The SPIRO FLOW-VOLUME MODULE (USB)™ available from VACUMED (Ventura, Calif.) includes gas flow volume measurement technology for use in spirometry for collecting ventilation data of the natural airways.

The output of gas analyzer 1074 is, in some embodiments, provided to a controller 1073 to display the results of the gas analysis. Where controller 1073 is also connected to pressure-actuated valve 1071, controller can, if desired, identify/select data from gas analyzer 1004 from only the period in which the desired exhale pressure is achieved. Controller 1073 is, in some embodiments, a computer system. In some embodiments controller 1073 and gas analyzer 1004 are integrated into a single unit. In a preferred embodiment controller 1073 and gas analyzer 1004 are integrated in to a single portable unit. Controller 1000 preferably records the results of the gas measurement and analysis and allows the physician to compare the results of the gas measurement/analysis with prior results for the same and other patients. In some cases, where the flow of gases through the pneumostoma during the period of elevated pressure is less than a threshold, the computer system and/or physician will recommend an aftercare procedure designed to reopen/improve flow through the pneumostoma 110.

FIG. 10B shows an alternative embodiment in which gas analyzer 1050 and a gas collection device 1061 are integrated into a handheld pneumostoma diagnostic device 1060. In general terms, gas collection device 1061 is a device which can be secured into a pneumostoma for sampling gases exiting the pneumostoma. Gas collection device 1061 forms part of a handheld pneumostoma diagnostic device 1060 which utilizes such gas sampling for assessment of pneumostoma function and/or lung function. A patient can be advised to use pneumostoma diagnostic device 1060 each time the patient removes a pneumostoma management device form the pneumostoma, or once a week, or on some other schedule. Alternatively, pneumostoma diagnostic device 1060 is used by a medical provider or caregivers.

Referring to FIG. 10B, gas collection device 1061 collects gases exhaled from the parenchymal tissue of the lung for analysis by gas analyzer 1050. Gas collection device 1061 is similar to pneumostoma interface 1006 of FIG. 10A and gas analysis device 400 of FIG. 4D. Gas collection device 1061 includes a hollow tube 1063 for insertion into a pneumostoma. Hollow tube 1063 is surrounded at the proximal end by a flange 1062 which prevents over-insertion of hollow tube 1063 into the pneumostoma and also seals to the chest of a patient so that gas does not leak from the pneumostoma around hollow tube 1063. Hollow tube 1063 connects to a coupling 1064 on the proximal side of flange 1062. Coupling 1064 is configured so that it may be readily connected and disconnected from gas analyzer 1050. Hollow tube 1063 has one or more holes 1066 at and/or adjacent the distal end, through which gas may pass out of a pneumostoma into hollow tube 1063. Hollow tube 1063 and flange 1062 also provide a temporary seal which inhibits leakage of gas from around hollow tube 1063. In some embodiments, hollow tube 1063 and flange 1062, because they are in contact with the pneumostoma, are singled-use disposables. In alternative embodiments, hollow tube 1063 and flange 1062 are multi-use sterilizable items.

Referring again to FIG. 10B, gas collection device 1061 is connected by coupling 1064 to coupling 1052 of gas analyzer 1050. Coupling 1052 (or gas collection device 1061) includes one or more isolation devices for preventing contamination of gas analyzer 1050 by material exiting the pneumostoma through the gas collection device 1061 including, for example, replaceable filters, sleeves, tubes etc. This allows gas analyzer 1050 to be reused by the same patient (or used by a physician with different patients) over an extended period while disposable components, for example gas collection device 1060 are periodically (including every time) replaced, cleaned and/or sterilized.

The gases exhaled from the pneumostoma 110 are measured and/or analyzed during a elevated-pressure period in the parenchymal tissue. For example, the pressure, volume and/or flow of gas exhaled may be measured by gas analyzer 1050, using methods known in the art, to provide information regarding the patency/functionality of the pneumostoma. See, e.g. the pocket-size medical spirometer disclosed in U.S. Pat. No. 7,383,740 entitled to "Spirometer" to Krosilchikov et al., which is incorporated herein by reference. In some embodiments, gas analyzer 1050 automatically detects the signal caused by controlled pressure exhalation and records data within a window where the signal is detected. In alternative embodiments, gas analyzer 1050 is provided with a switch 1054 which the patient or physician actuates during the period when controlled pressure exhalation is sustained. The gas analyzer 1050 records data within the window where the switch is actuated. The exhaled gas is, in some embodiments, also analyzed by gas analyzer 1050 to determine oxygen and carbon dioxide concentrations.

Gas analyzer 1050 is battery-operated and includes a display 1056 which displays information regarding the measurements made by gas analyzer 1050 to the physician and/or patient. Such information is useful in determining the effectiveness of a pneumostoma and the location and/or desirability of additional pneumostomas. Gas analyzer 1050 is capable of measuring and displaying a clinically relevant range of measurements—for example 0-0.6 liters per second and/or 0-30 cm $H_2O$. The gas analyzer, in some embodiments, has different modes including, e.g.: analyzing gas output during tidal breathing, analyzing gas during controlled pressure exhalation at 10 cm $H_2O$; analyzing gas during controlled pressure exhalation at 20 cm $H_2O$. The display scale is changed based on the mode to indicate a range clinically relevant to the mode. For example during tidal breathing, the scale might be 0-0.35 liters per second. The display 1056, in some embodiments, also includes information regarding a minimum threshold for gas pressure/flow/volume from the pneumostoma during the controlled pressure exhalation. In FIG. 10B, the threshold is indicated by shaded bars 1057 which are colored differently (e.g. red) than the other bars. Where the gas pressure/flow/volume is indicated to be less than the threshold, the patient is in some embodiments advised to undergo more detailed pneumostoma functionality assessment and/or treatment.

In some embodiments, gas analyzer 1050 is provided with a memory, not shown, which stores data regarding the results obtained by gas analyzer 1050. In some cases, the display is observed during the forced exhale. In other cases the display is observed after one, or a series of forced exhales with information about each exhalation and/or an aggregate analysis of the series exhalations shown on the display at one time or in series. Gas analyzer 1050 is provided with a port 1058, for example a USB port. Port 1058 can be used for charging gas analyzer 1050 and transferring data from gas analyzer 1050 to a computer for interpretation by a physician. In some embodiments the data is transferred to a local computer by a patient and then transmitted over a network to a remote computer for interpretation by a physician. By logging the results of gas analyzer 1050, changes in function of the pneumostoma over time are monitored allowing diagnosis of function and selection of procedures to maintain the function of the pneumostoma over time.

FIG. 10C illustrates an example of a method for determining pneumostoma function using the systems described in FIGS. 10A, 10B. The patient/physician first removes the pneumostoma management device from the pneumostoma (step 1010). The patient/physician next visually inspects the pneumostoma (step 1011) to determine whether there are any contraindications to use of the gas collection device, for example any obstruction of the pneumostoma which must first be removed. If the external inspection reveals no contraindications, the gas collection device is introduced into the pneumostoma and sealed to the chest of the patient (step 1012). The airway interface, e.g., a nasal pillow, nose mask, mouth tube and/or full-face mask is then sealed to the airway of the patient (step 1013).

The patient then exhales into the airway interface against the pressure-actuated valve (step 1014). When the patient achieves sufficient pressure in the lungs to crack the valve, and air escapes through the valve. While the valve is open the pressure of gases in the parenchymal tissue of the lung is sustained at a selected pressure which may be a standard pressure. While the pressure of gases in the parenchymal tissue of the lung is sustained at the selected pressure, the gas analysis device is triggered to gather gas data regarding the gas flow/pressure/volume escaping from the pneumostoma through the gas collection device (step 1015). Steps 1014 and 1015 can be repeated a number of times (step 1016). In alternative embodiments, the gas analysis device sample gas continuously and subsequently the data pertaining to the forced exhalation period is selected from the collected data.

After collecting sufficient data, the patient/physician removes the gas collection device from the pneumostoma (step 1017) (the gas interface is also removed from the patients' airway). The removed PMD or a new PMD is then inserted into the pneumostoma (step 1018). At some point after step 1015, the gas analyzer analyzes the gas data in order to generate a standardized measure of gas flow, volume or pressure (step 1019). Where steps 1014 and 1015 were repeated a number of times, statistical techniques can be used to generate a better measure of gas flow/pressure/volume. The standardized measure of gas flow/pressure/volume can the be compared with predetermined thresholds, the prior results with respect to the patient's pneumostoma and average results achieved by groups of similar patients. From the comparisons, a physician can determine a proposed course of maintenance/treatment for the pneumostoma. This method can be adapted for use of each of the assessment devices disclosed in FIGS. 4A-4E, 10A-10B and 10D-10F and accompanying text.

FIG. 10D shows an alternative system for creating a standard/repeatable pressure differential between the parenchymal tissue of the lung and the ambient atmosphere in order to permit standardized measuring/analyzing of the gases leaving the pneumostoma. As shown in FIG. 10D, patient receives air from a CPAP (Constant Positive Airway Pressure) machine 1081 via an airway interface 1082. For diagnosing patency of a pneumostoma, CPAP machine 1081 is connected to airway interface 1082 and the standard positive pressure is applied. Suitable prescribed/titrated pressures include pressures between 5 and 30 cm $H_2O$ (492 and 2940 Pa). However, it is preferable to choose a standard pressure that can be well tolerated by all patients such as, for example, 5, 10 or 15 or 20 cm $H_2O$. (492, 980, 1470 or 1960 Pa).

CPAP machines are commonly used to diagnose and/or treat sleep apnea. The CPAP machine treats apnea by delivering a stream of compressed air via a hose to airway interface 1082 (including for example a nasal pillow, nose mask and/or full-face mask), splinting the airway (keeping it open under air pressure) so that unobstructed breathing becomes possible. The CPAP machine blows air at a prescribed pressure (also called the titrated pressure). A typical CPAP machine can deliver prescribed/titrated pressures between 4 and 20 cm $H_2O$. More specialized units can deliver prescribed/titrated pressures up to 25 or 30 cm $H_2O$. An example of a CPAP machine is described in U.S. Pat. No. 5,245,995 entitled "Device And Method For Monitoring Breathing During Sleep, Control Of CPAP Treatment, And Preventing Of Apnea" to Sullivan et al. which is incorporated herein by reference. However, a range of CPAP machines and variations thereof are known to those of skill in the art. "CPAP machine" as used herein is a generic terms which includes all CPAP machines and variations thereof suitable for providing controlled positive pressure to the airway and lungs. In some embodiments CPAP machines are designed to determine gas flow in and out of airway interface 1082.

Referring again to FIG. 10D, a pneumostoma interface 1006 is inserted into the pneumostoma 110 of a patient 1000. Pneumostoma interface 1006 is connected by tube 1072 to gas analyzer 1074. One or more isolation devices for preventing contamination of gas analyzer 1074 by material exiting the pneumostoma through the pneumostoma interface 1006 including, for example, replaceable filters, sleeves, tubes etc.

The gases exhaled from the pneumostoma 110 are then measured and/or analyzed during controlled pressure exhalation. The pressure, volume and/or flow of gas exhaled may be measured by gas analyzer 1074 to provide information regarding the patency/functionality of the pneumostoma. The exhaled gas may be also be analyzed by gas analyzer 1074 to determine oxygen and carbon dioxide concentrations. In some cases, the concentrations are compared to oxygen and carbon dioxide concentrations in the gases exhaled through the natural airways or in the ambient atmosphere. Such evaluation may be useful in determining the effectiveness of a pneumostoma and the location and/or desirability of additional pneumostomas.

The output of gas analyzer 1074 may be provided to a controller 1084 to display the results of the gas analysis. Controller 1084 is, in some embodiments, a computer system. Controller 1084 preferably records the results of the gas measurement and analysis and allows the physician to compare the results of the gas measurement/analysis with prior results for the same and other patients. In some cases, where the flow of gases through the pneumostoma during the period a standard pressure is induced by CPAP machine 1081 is less than a threshold, the computer system and/or physician will recommend an aftercare procedure designed to reopen/improve flow through the pneumostoma 110.

Referring to FIG. 10E, in a preferred embodiment, an integrated pneumostoma diagnostic machine 1088 integrates, into a single device: CPAP machine 1081 which provides air, at a standard positive pressure to a patient via airway interface 1082; and includes a gas analyzer 1074 for analyzing gases from a pneumostoma interface 1006, a controller 1084, input interface 1086 and display 1085. The pneumostoma interface 1006 and airway interface 1082 are detachable from the integrated pneumostoma diagnostic machine 1088 for cleaning and/or replacement. One or more isolation devices are provided for preventing contamination of pneumostoma diagnostic machine 1088 by material exiting the pneumostoma or airways of the patient, including, for example, replaceable filters, sleeves, tubes etc. This pneumostoma diagnostic machine 1088 is capable of providing gas at constant positive pressure to the airway interface 1082 and also measuring/analyzing, recording and/or displaying the pressure, volume and/or flow of gas exhaled into pneumostoma interface 1006 through the pneumostoma of a patient. The exhaled gas is also, in some embodiments, analyzed by gas analyzer 1074 to determine oxygen and carbon dioxide concentrations.

The output of gas analyzer 1074 is, in some embodiments, provided to a controller 1084 to display the results of the gas measurement/analysis. Controller 1084, in some embodiments, includes, e.g. a CPU, ASIC, microcontroller, and software/firmware. Controller 1084 preferably records the results of the gas measurement/analysis and allows the physician to compare the results of the gas measurement/analysis with prior results for the same and other patients. Controller can display controls and/or result via display 1085. Controller 1084 can also preferably receive input commands via input controls 1086, which, in some embodiments, include: display 1085 (if provided with a touch screen), buttons, switches, knobs, keyboards and/or mice. Display 1085 and input controls 1086 are, in some embodiments, external to pneumostoma diagnostic machine 1088 and, in other embodiments, are integrated into single portable unit. In some cases, where the flow of gases through the pneumostoma during the period a standard positive pressure is less than a threshold, the pneumostoma diagnostic machine 1088 and/or physician will recommend an aftercare procedure designed to reopen/improve flow through the pneumostoma 110.

FIG. 10F illustrates an alternative preferred embodiment of a mechanical pneumostoma diagnostic device 1090. Pneumostoma diagnostic device 1090 includes: pneumostoma interface 1006; airway interface 1072 (as described above); pressure-actuated valve 1071 (as described above); and a mechanical indicator device 1092. In a preferred embodiment, airway interface 1072 includes a stiff tube 1076 to which pressure-actuated valve 1071 is mounted. Pressure-actuated valve 1071 is preferably a spring-loaded check valve having a predetermined crack pressure. The predetermined crack pressure can be, for example a pressure selected from 5, 10 or 15 cm $H_2O$. (492, 980 or 1470 Pa). Forced exhalation against the pressure-actuated valve 1071 allows the patient to achieve and sustain a selected elevated pressure in the gases of the parenchymal tissue of the lung for a time during a test of pneumostoma function.

Mechanical indicator device 1092 is, in some embodiments, mounted to (but not in fluid communication with) stiff tube 1076 at a position which allows a patient to comfortably observe the mechanical indicator device 1092. Mechanical indicator device 1092 is connected by a flexible inelastic tube 1094 to pneumostoma interface 1006. Mechanical indicator device 1092 can, in some embodiments, provide an indication of gas pressure in the pneumostoma and/or gas flow through the pneumostoma.

Referring again to FIG. 10F, mechanical indicator device 1092, in some embodiments, includes an indicator tube 1095 in which is disposed a ball 1096. Flexible inelastic tube 1094 is connected to an entry aperture 1097 at the bottom end of indicator tube 1095. Entry aperture 1097 is too small to allow ball 1096 to exit indicator tube 1095. An exit aperture 1098 at the top end of exit indicator tube 1095. When gas flows into the entry aperture 1097 and exits via the exit aperture 1098 the flow of gas through indicator tube 1095 in proportion to the gas flow rate. A scale 1099 is provided on the outside of indicator tube 1095 so that the patient can determine flow of gas exiting the pneumostoma by observing the position of ball 1096 relative to scale 1099. Indicator tube can, in some embodiments, also be provided with a minimum threshold line 1093. The weight and diameter of the ball and the internal diameter of the indicator tube 1095 are selected such that the ball rises from the bottom of scale 1099 to the top of scale 1099 over a clinically relevant range of gas flow rates. For example the scale 1099 can in some embodiments cover the range from 0 to 0.5 liters per second. The gradations of scale 1099 include, in preferred embodiments, arbitrary unit indicators (not shown) (e.g. 0-10) which corresponds to gas flow rates. Thus for example "10" corresponds to 0.5 liters per second and "0" to 0 liters per second. Threshold 1093 can, for example be set to indicate 0.1 liters per second. The arbitrary unit indicators (not shown) of scale 1099 and threshold 1093 are provided in a positions where they can be comfortably observed by the patient.

In an alternative embodiment, mechanical indicator device 1092 is a low pressure manometer. The low pressure monitor indicates pressure in the pneumostoma during high pressure exhalation. A suitable low-pressure manometer preferably covers a clinically-relevant range of pressures, such as, for example, a range of 0 cm $H_2O$ to 30 cm $H_2O$.

To use pneumostoma diagnostic device 1090, a patient first removes a pneumostoma management device from the pneumostoma and then inserts and seals pneumostoma interface 1006 of pneumostoma diagnostic device 1090 to the pneumostoma. The patient next seals airway interface 1072 of pneumostoma diagnostic device 1090 to the mouth and/or nose. The patient next exhales into airway interface 1072 and develops a predetermined pressure sufficient to cause pressure-actuated valve 1071 to release gases. During the period in which pressure-actuated valve 1071 is releasing gas, the patient observes mechanical indicator device 1092 of pneumostoma diagnostic device 1090 to determine the indicated gas pressure in the pneumostoma and/or gas flow through the pneumostoma. The patient can repeat the assessment a number of times to determine the indicated gas pressure in the pneumostoma and/or gas flow through the pneumostoma. The patient next removes pneumostoma diagnostic device 1090 and replaces a pneumostoma management device into the pneumostoma. The patient optionally records in a log the maximum indicated gas pressure in the pneumostoma and/or gas flow through the pneumostoma. In some cases, where the pressure/flow of gases through the pneumostoma, during the period standard positive pressure is achieved, is consistently less than the threshold 1093 indicated on mechanical indicator device 1092 of pneumostoma diagnostic device 1090, the patient is advised to call their physician for a more accurate check-up and assessment of pneumostoma patency. If indeed the patency of the pneumostoma is less than a desired minimum the physician will recommend an aftercare treatment designed to reopen/improve flow through the pneumostoma 110.

Pneumostoma diagnostic device 1090 or similar devices can be used as part of a pulmonary rehabilitation program for patients with a pneumostoma. By providing direct visual feedback of the pneumostoma function, the pneumostoma diagnostic device 1090 promotes healthy maintenance of the pneumostoma by the patient. Direct feedback provides patient motivation which improves patient compliance with pulmonary rehabilitation and other pneumostoma care protocols. In some situations, regular exhalation at an elevated pressure differential relative to ambient atmosphere and/or regular use of CPAP can be utilized to help maintain the patency of the pneumostoma. The increased pressure can be achieved by for example by forced exhalation through pursed lips, forced exhalation against a pressure-actuated valve as described above, and/or use of a positive pressure ventilation machine such as the CPAP machine described above.

In one example, using the pneumostoma diagnostic device 1090 of FIG. 10F, a patient can exhale against pressure-actuated valve 1071 and assess pneumostoma function on a selected periodic basis. Alternatively, the patient can use the pneumostoma diagnostic device 1090 of FIG. 10F on a first schedule, for example daily, without inserting pneumostoma interface 1006 into the pneumostoma, thereby treating the pneumostoma without assessing pneumostoma function. The patient can then use the pneumostoma diagnostic device 1090 of FIG. 10F on a separate schedule, for example weekly, including inserting pneumostoma interface 1006 into the pneumostoma, thereby treating the pneumostoma and assessing pneumostoma function.

The foregoing description of preferred embodiments of the present invention has been provided for the purposes of illustration and description. It is not intended to be exhaustive or to limit the invention to the precise forms disclosed. Many embodiments were chosen and described in order to best explain the principles of the invention and its practical application, thereby enabling others skilled in the art to understand the invention for various embodiments and with various modifications that are suited to the particular use contemplated. Embodiments of the present invention may use some or all of the features shown in the various disclosed embodiments where such features are not structurally or functionally incompatible. It is intended that the scope of the invention be defined by the claims and their equivalents.

What is claimed is:

1. A method for assessing function of a pneumostoma in a chest of a patient, the method including:
   (a) receiving an elevated-exhalation-pressure control device into the patient's mouth;
   (b) inserting a gas collection device into the pneumostoma;
   (c) assessing qualities of gas in the pneumostoma during a time period in which a patient is exhaling at an elevated pressure through the elevated-exhalation-pressure control device; and
   (d) removing the gas collection device from the pneumostoma.

2. The method of claim 1, wherein step (a) comprises: (a1) inserting a pneumostoma management device into the pneumostoma, (a2) receiving an elevated-exhalation-pressure control device into the patient's mouth; step (b) comprises: (b1) removing a pneumostoma management device from the pneumostoma; and then (b2) inserting a gas collection device into the pneumostoma.

3. The method of claim 1, wherein step (d) comprises: (d1) removing the gas collection device from the pneumostoma; and then (d2) inserting a pneumostoma management device into the pneumostoma.

4. The method of claim 1, wherein step (c) comprises:
   assessing qualities of gas in the pneumostoma during a time period in which a patient is exhaling at elevated pressure through the elevated-exhalation-pressure control device, said assessing including measuring the amount of gas flowing from the pneumostoma.

5. The method of claim 1, wherein step (c) comprises:
   assessing qualities of gas in the pneumostoma during a time period in which a patient is exhaling at elevated pressure through the elevated-exhalation-pressure control device, said assessing including measuring the pressure of gas in the pneumostoma.

6. The method of claim 1, further comprising:
   (e) comparing the qualities of gas assessed in step (d) with qualities of gas assessed in the patient on different days and determining a trend with respect to function of the pneumostoma.

7. The method of claim 1, further comprising:
   (e) comparing the qualities of gas assessed in step (d) with predetermined qualities of gas and taking a further treatment action in response.

8. The method of claim 1, wherein steps (a) through (d) are performed by the patient and wherein the method performed by the patient further comprises:
   (e) comparing the qualities of gas assessed in step (d) with a threshold and contacting a physician if the qualities of gas assessed in step (d) compare unfavorably with the threshold.

9. The method of claim 1, wherein steps (a) through (d) are performed by a medical provider and wherein the method performed by the medical provider further comprises:
   (e) comparing the qualities of gas assessed in step (d) with a threshold and making a treatment decision if the qualities of gas assessed in step (d) compare unfavorably with the threshold.

10. A system for assessing pneumostoma function of a pneumostoma of a patient, the system comprising:
    an airway interface adapted to make a seal with a natural airway of a patient;
    a pressure elevating system coupled to the airway interface which elevates a pressure of gas in the airway interface;
    a pneumostoma interface having a seal and a gas collection tube;
    a gas analyzer coupled to the pneumostoma interface wherein the gas analyzer measures at least one quality of gas in the pneumostoma during a period of time when the patient is exhaling and the a pressure of gas in the airway interface is elevated; and
    a display for displaying an assessed quality of gas measured by the gas analyzer.

11. The system of claim 10, wherein the airway interface is one of a nasal pillow, a nose mask, a mouth tube and a full-face mask.

12. The system of claim 10, wherein the pressure elevating system includes a check valve coupled to the airway interface which prevents the patient from exhaling until the pressure in the airway interface reaches a selected elevated pressure.

13. The system of claim 10, wherein the pressure elevating system includes a positive pressure ventilator.

14. The system of claim 10, wherein the pneumostoma interface comprises:
    a tube sized to fit within the pneumostoma and adapted to collect gas from the pneumostoma; and
    a flange adapted to seal to the patient and prevent escape of gas from the pneumostoma except through said tube.

15. The system of claim 10, wherein:
    the gas analyzer is secured to the airway interface at a position where the display can be observed by the patient during exhalation.

16. The system of claim 10, wherein:
    the display is an electronic display and the system further comprises a memory for recording the assessed quality of gas measured by the gas analyzer at different times.

17. The system of claim 10, wherein:
    the system comprises a memory for recording the assessed quality of gas measured by the gas analyzer at different times; and
    an interface adapted to transmit, to a computer system, data regarding the assessed quality of gas measured by the gas analyzer at different times.

18. The system of claim 10, wherein:
    the system comprises a memory for recording the assessed quality of gas measured by the gas analyzer at different times; and
    an interface adapted to transmit, to a remote computer system, data regarding the assessed quality of gas measured by the gas analyzer at different times.

19. The system of claim 10, wherein the pressure elevating system, gas analyzer; and display are integrated into a single portable unit.

20. A method for assessing function of a pneumostoma in a chest of a patient, the method including:
    (a) receiving an elevated-exhalation-pressure control device into the pneumostoma;
    (b) inserting a gas collection device into the patient's mouth;
    (c) assessing qualities of gas in the patient's mouth during a time period in which a patient is exhaling at an elevated pressure through the elevated-exhalation-pressure control device; and
    (d) removing the gas collection device from the patient's mouth.

* * * * *